United States Patent [19]  [11] 3,931,279
Nelson  [45] Jan. 6, 1976

[54] 5-OXA PROSTAGLANDIN $F_{2\alpha}$ ANALOGS
[75] Inventor: Norman A. Nelson, Galesburg, Mich.
[73] Assignee: The Upjohn Company, Kalamazoo, Mich.
[22] Filed: May 21, 1973
[21] Appl. No.: 361,991

[52] U.S. Cl. ...... 260/468 D; 260/211 R; 260/240 R; 260/247.2 R; 260/268 R; 260/243.6 S; 260/243.8; 260/243.83; 260/326.2; 260/326.47; 260/345.8; 260/345.9; 260/349.4; 260/347.8; 260/429.9; 260/439 R; 260/448 R; 260/448.8 R; 260/473 A; 260/501.1; 260/501.15; 260/501.17; 260/501.2; 260/514 D; 260/520; 260/615 R; 424/305; 424/308; 424/317
[51] Int. Cl.² ............... C07C 61/38; C07C 69/74; C07C 63/592; C07C 63/60
[58] Field of Search ...... 260/468 D, 514 D, 514 UA

[56] References Cited
FOREIGN PATENTS OR APPLICATIONS
2,036,471  2/1971  Germany ............... 260/468

OTHER PUBLICATIONS
Corey et al., JACS, 91(56752), (1969).
Fried, et al., Annals of the N. Y. Academy of Sciences, 180, 38, (1971).

Primary Examiner—Robert Gerstl
Attorney, Agent, or Firm—Morris L. Nielsen

[57] ABSTRACT
5-Oxa prostaglandin-type compounds and processes for making them. These compounds are useful for a variety of pharmacological purposes, including anti-ulcer, inhibition of platelet aggregation, increase of nasal patency, labor inducement at term, and wound healing.

44 Claims, No Drawings

5-OXA PROSTAGLANDIN F$_{2\alpha}$ ANALOGS

BACKGROUND OF THE INVENTION

This invention relates to novel compositions of matter, to novel methods for producing those, and to novel chemical intermediates useful in those processes. Particularly, this invention relates to certain novel analogs of prostaglandins E$_1$, F$_{1\alpha}$, F$_{1\beta}$, A$_1$, and B$_1$ in which the C-5 methylene (—CH$_2$) in the prostanoic acid structure is replaced by oxygen (—O—).

The known prostaglandins include, for example, prostaglandin E$_1$ (PGE$_1$), prostaglandin F$_1$ alpha and beta (PGF$_{1\alpha}$ and PGF$_{1\beta}$), prostaglandin A$_1$ (PGA$_1$), and prostaglandin B$_1$ (PGB$_1$). Each of the above-mentioned known prostaglandins is a derivative of prostanoic acid which has the following structure and atom numbering:

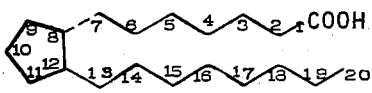

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_1$ has the following structure:

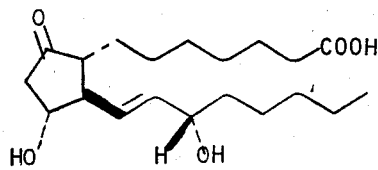

PGF$_{1\alpha}$ has the following structure:

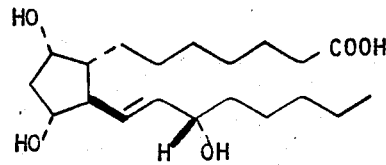

PGF$_{1\beta}$ has the following structure:

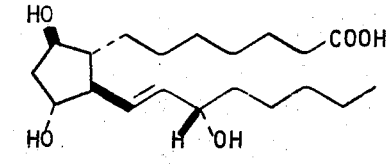

PGA$_1$ has the following structure:

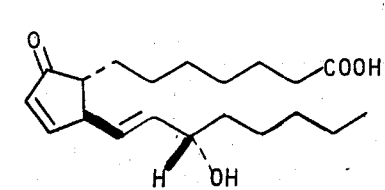

PGB$_1$ has the following structure:

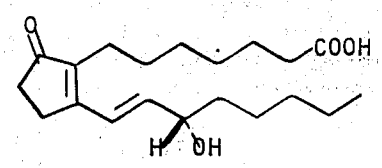

In formulas II to VI, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

The side-chain hydroxy at C-15 in formulas II to VI is in S configuration. See Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II to VI each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VI represents the other enantiomer of that prostaglandin. The racemic form of a prostaglandin contains equal numbers of both enantiomeric molecules, and one of formulas II to VI and the mirror image of that formula is needed to represent correctly the corresponding racemic prostaglandin. For convenience hereinafter, use of the terms, PGE$_1$, PGF$_{1\alpha}$, PGF$_{1\beta}$, and the like, will mean the optically active form of that prostaglandin with the same absolute configuration as PGE$_1$ obtained from mammalian tissues. When reference to the racemic form of one of those prostaglandins is intended, the word "racemic" or "dl" will preceed the prostaglandin name, thus, "racemic PGE$_2$" or "dl-PGF$_{2\alpha}$."

PGE$_1$, PGF$_{1\alpha}$, PGF$_{1\beta}$, PGA, and PGB$_1$ and their esters, acylates, and pharmacologically acceptable salts, are extremely potent in causing various biological responses. For that reason, these compounds are useful for pharmacological purposes. See, for example, Bergstrom et al., cited above. A few of those biological responses are systemic arterial blood pressure lowering in the case of the PGE and PGA compounds as measured, for example, in anesthetized (pentobarbital sodium) pentolinium-treated rats with indwelling aortic and right heart cannulas; pressor activity, similarly measured, for the PGF compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE and PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 $\mu$g. to about 10 mg. per ml. of a pharmacologically suitable liquid vehicle or as an aerosol spray, both for topical application.

The PGE, PGF$\alpha$, PGF$\beta$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other anti-asthmatic agents, such as sympathomimetics (isoproterenol, phenylephrine, ephedrine, etc.); xanthine derivatives (theophylline and aminophyllin); and corticosteroids (ACTH and prednisolone). Regarding use of these compounds see South African Pat. No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 $\mu$g. to about 500 $\mu$g. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, PGF$\alpha$, and PGF$\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, PGF$\alpha$, and PGF$\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, PGE$_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 $\mu$g. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGE or PGA compounds are useful as hypotensive agents to reduce blood pressure in mammals, including man. For this purpose, the compounds are administrered by intravenous infusion at the rate of about 0.01 to about 50 $\mu$g. per kg. of body weight per minute, or in single or multiple doses of about 25 to 500 $\mu$g. per kg. of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephric states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered by intravenous injection at a dose in the range 10 to 1000 $\mu$g. per kg. of body weight or by intraveneous infusion at a dose in the range 0.1 to 20 $\mu$g per kg. of body weight per minute until the desired effect is obtained. Subsequent doses are given by intravenous, intramuscular, or subcutaneous injection or infusion in the range 0.05 to 2 mg. per kg. of body weight per day.

The PGE, PGF$\alpha$, and PGF$\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 $\mu$g. per kg. of body weight per minute until or near the termination of the second stage of labor, i.e., expulsion of the fetus. These compounds are especially useful when the female is one or more weeks post-mature and natural labor has not started, or 12 to 60 hours after the membranes have ruptured and natural labor has not yet started. An alternative route of administration is oral.

The PGF$\alpha$ and PGF$\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose, PGF$_{1\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

The PGE and PGF compounds are useful in causing cervical dilation in pregnant and nonpregnant female mammals for purposes of gynecology and obstetrics. In labor induction and in clinical abortion produced by these compounds, cervical dilation is also observed. In cases of infertility cervical dilation produced by PGE and PGF compounds is useful in assisting sperm movement to the uterus. Cervical dilation by prostaglandins is also useful in operative gynecology such as D and C (Cervical Dilation and Uterine Curettage) where mechanical dilation may cause perforation of the uterus, cervical tears, or infections. It is also useful in diagnostic procedures where dilation is necessary for tissue examination. For these purposes, the PGE and PGF compounds are administered intramuscularly or subcutaneously at doses of about one to 25 mg. per treatment. The exact dosages for these purposes depend on the age, weight, and condition of the patient or animal.

As mentioned above, the PGE compounds are potent antagonists of epinephrine-induced mobilization of free fatty acids. For this reason, these compounds are useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGB compounds promote and accelerate the growth of epidermal cells nd keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separately or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. Especially for topical use, these prostaglandins are useful in combination with antibiotics, for example, gentamycin, neomycin, polymyxin B, bacitracin, spectinomycin, and oxytetracyline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

Several related compounds have been reported in the literature. dl-3-Oxa-PGE$_1$, dl-3-oxa-PGF$_{1\alpha}$, and dl-3-oxa-PGA$_1$, all as ethyl esters, were described by G. Bundy et al., Ann. N.Y. Acad. Sci. 180, 76 (1971). See also German Offenlegungsschrift No. P 2,036,471, February 11, 1971, reference in Derwent No. 10,044S-B. 15-Deoxy-7-oxa-PGE$_1$ and 7-oxa-15$\alpha$ /$\beta$ -PGE$_1$ were reported by J. Fried et al., Tetrahedron Lett. 2695 (1970).

SUMMARY OF THE INVENTION

It is a purpose of this invention to provide novel 5-oxa prostagalandin E, F, A, and B analogs, It is a further purpose to provide novel 5-oxa prostaglandin analogs with a variety of substituents and degrees of saturation in the side chains. It is a further purpose to provide 5-oxa prostaglandin analogs having the 11- deoxy ring-structure in which the 11-hydroxy is replaced by hydrogen. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The novel prostaglandin analogs of this invention each have an oxygen (—O—) in place of the methylene (—CH$_2$—) moiety at the 5-position of the prostanoic acid formula. They are represented by the generic formula

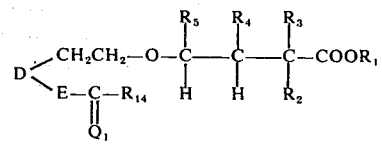

VII wherein D is one of the six carbocyclic moieties:

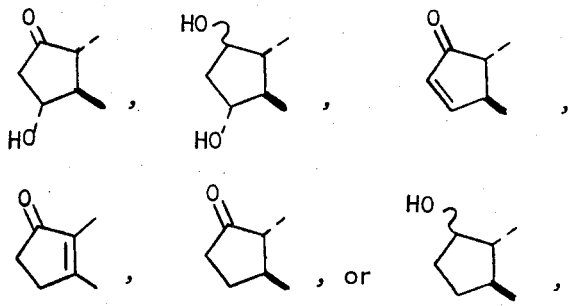

wherein ~ indicates alpha or beta attachment of hydroxyl to the cyclopentane ring; wherein E is —CH$_2$CH$_2$— or

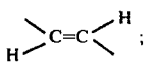

wherein Q$_1$ is

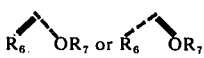

wherein R$_6$ and R$_7$ are hydrogen or alkyl of one to 4 carbon atoms, inclusive, being the same or different, wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein R$_3$ is hydrogen, alkyl of one to 4 carbon atoms, inclusive, or fluoro; wherein R$_2$ is hydrogen or fluoro, with the proviso that R$_2$ is fluoro only when R$_3$ is hydrogen or fluoro; wherein R$_4$ and R$_5$ are hydrogen or alkyl of one to 4 carbon atoms, inclusive, being the same or different with the proviso that no more than one of R$_3$, R$_4$, and R$_5$ is alkyl; and wherein R$_{14}$ is

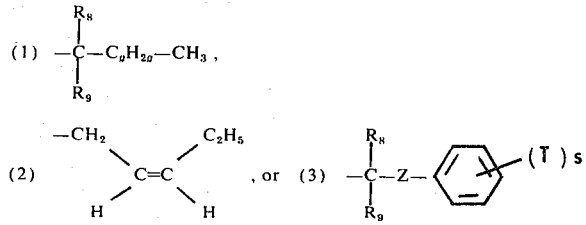

with the proviso that R$_{14}$ is

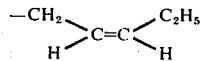

only when E is $$\underset{H}{\overset{\diagdown}{}}C=C\underset{\diagdown}{\overset{H}{}};$$

wherein C$_g$H$_{2g}$ is alkylene of one to 9 carbon atoms, inclusive, with one to 5 carbon atoms, inclusive, in the chain between —CR$_8$R$_9$— and terminal methyl; wherein R$_8$ and R$_9$ are hydrogen, alkyl of one to 4 carbon atoms, inclusive, or fluoro, being the same or different, with the proviso that R$_9$ is fluoro only when R$_8$ is hydrogen or fluoro; wherein T is alkyl of one to 4 carbon atoms, inclusive, fluoro, chloro, trifluoromethyl, or —OR$_{10}$, wherein R$_{10}$ is hydrogen or alkyl of one to 4 carbon atoms, inclusive, and s is zero, one, 2, or 3, with the proviso that not more than two T's are other than alkyl; and wherein Z represents an oxa atom (—O—) or C$_j$H$_{2j}$, wherein C$_j$H$_{2j}$ is a valence bond or alkylene of one to 9 carbon atoms, inclusive, substituted with zero, one, or 2 fluoro, with one to 6 carbon atoms, inclusive, between —CR$_8$R$_9$— and the ring.

For example, 5-oxa-PGE$_1$, one of the novel compounds of this invention, is represented by the formula:

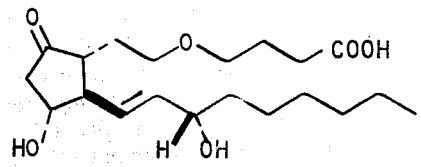

VIII

Some of the novel prostaglandin analogs of this invention have longer or shorter alkyl-terminated side chains than 5-oxa-PGE$_1$. For example, 5-oxa-20-methyl-PGE$_1$, in which the alkyl-terminated side chain has nine carbon atoms, is represented by the formula:

IX

5-Oxa-19,20-dinor-PGE$_1$, in which the alkyl-terminated side chain has only six carbon atoms, is represented by the formula:

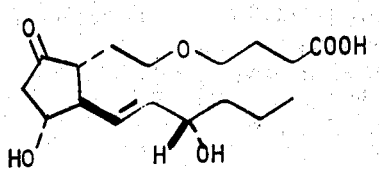 X

Some of the novel prostaglandin analogs of this invention have alkyl-terminated side chains which are more or less saturated than 5-oxa-PGE$_1$. For example, 5-oxa-17,18-dehydro-PGE$_1$, in which the C$_{17}$ and C$_{18}$ carbon atoms are connected by a double bond, is represented by the formula:

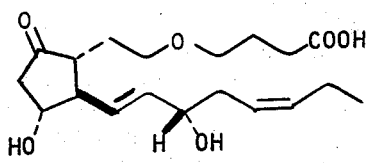 XI

5-Oxa-13,14-dihydro-PGE$_1$, in which the normal C$_{13}$–C$_{14}$ —CH=CH— moiety is replaced by —CH$_2$—CH$_2$—, is represented by the formula:

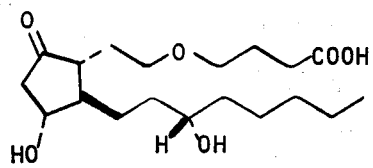 XII

Some of the novel prostaglandin analogs of this invention have alkyl or fluoro substituents on the side chains. Others of the novel prostaglandin analogs of this invention have phenyl and substituted-phenyl substitution. For example, 16,16-dimethyl-5-oxa-PGE$_1$ is represented by the formula:

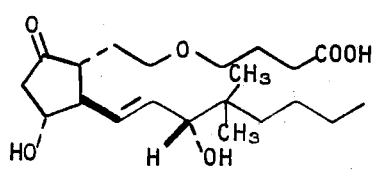 XIII

5-Oxa-17-phenyl-18,19,20-trinor-PGE$_1$ is represented by the formula:

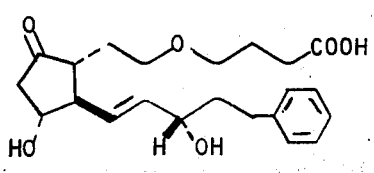 XIV

Also included among the novel prostaglandin analogs of this invention are 15-alkoxy and 16-phenoxy ethers.

5-oxa-PGE$_1$, 15-methyl ether is represented by the formula

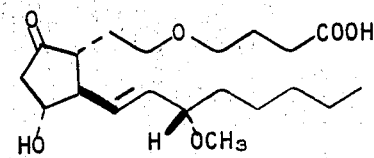 XV

16-Methyl-5-oxa-16-phenoxy-18,19,20-trinor-PGE$_1$, is represented by the formula

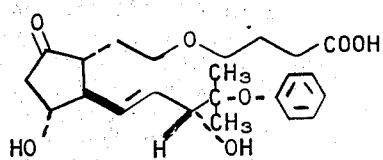 XVI

Also included within the novel prostaglandin analogs of this invention are the corresponding PGF, PGA, PGB, 11-deoxy-PGE, and 11-deoxy-PGF compounds. For example, 5-oxa-PGF$_{1\alpha}$ is represented by the formula

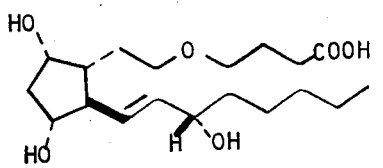 XVII

5-Oxa-PGA$_1$ is represented by the formula

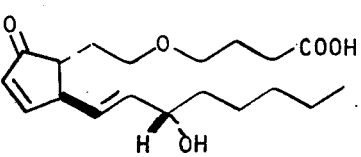 XVIII

5-Oxa-11-deoxy-PGE$_1$ is represented by the formula

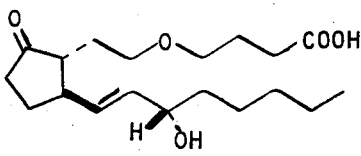 XIX

5-Oxa-11-deoxy-PGF$_{1\beta}$ is represented by the formula

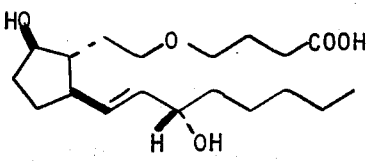 XX

The names of these examples of formulas VII to XX are typical of the names used hereinafter for the novel compounds of this invention. These names can better be understood by reference to the structure and numbering system of prostanoic acid (Formula I, above). That formula has seven carbon atoms in the carboxy-terminated chain and eight carbon atoms in the methyl-terminated chain. In these names, "5-oxa" indicates an oxa oxygen (—O—) in place of the C-5 methylene of the prostaglandin compound.

The use of "nor", "dinor", or "trinor" in the names of the novel compounds of this invention indicates the absence of one, two, or three of the chain carbon atoms and the attached hydrogen atoms. The number or numbers in front of "nor", "dinor", or "trinor" indicate which of the original prostanoic acid carbon atoms are missing in the named compound. It is understood that the terminal carbon atom in a chain carries its normal complement of hydrogen atoms. Formulas X, XIV, and XVI, above, illustrate this system of nomenclature.

In the name of the formula-IX example, "20-methyl" indicates that a methyl group replaces a hydrogen on C-20 so that the chain is extended by one carbon atom.

Where there is substitution in the side chains, for instance alkyl, fluoro, or phenyl, the points of attachment to the side chains are indicated in the conventional manner, following the atomic numbering of the prostanoic acid skeleton. Formulas XIII and XIV, above, are illustrative.

In the names of these compounds, "17,18-dehydro-PGE$_1$" indicates that there is one less hydrogen on each of the C-17 and C-18 carbon atoms than in the PGE$_1$ structure, so that the normal —CH$_2$CH$_2$— moiety is replaced with —CH=CH—. "13,14-Dihydro-PGE$_1$" in the name indicates one more hydrogen on each of the C-13 and C-14 carbon atoms than in the PGE$_1$ structure, so that the —CH=CH— moiety is replaced with —CH$_2$CH$_2$—. In these names, "11'-deoxy" indicates that the hydroxyl at C-11 is replaced with hydrogen. Formulas X, XII, XIX, and XX, above, are illustrative.

Included in the novel compounds of this invention are the 15-epimers. Where the C-15 configuration is the same as that of the natural prostaglandin PGE$_1$, identified as S-configuration, the name will not identify the configuration at C-15. If the 15-epimer is intended, the name will include "15-beta" or "15(R)".

The presently described acids and esters of the 5-oxa-prostaglandin analogs include compounds of the following formulas which are intended to represent the same optically form as of the naturally occurring prostaglandins. There are also included the racemic compounds represented by each respective formula and the mirror image thereof. There are also included the alkanoates of two to 8 carbon atoms, inclusive and also the pharmacologically acceptable salts thereof when R$_1$ is hydrogen.

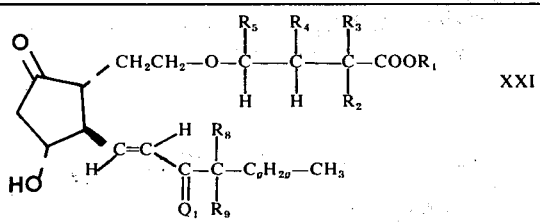

XXI

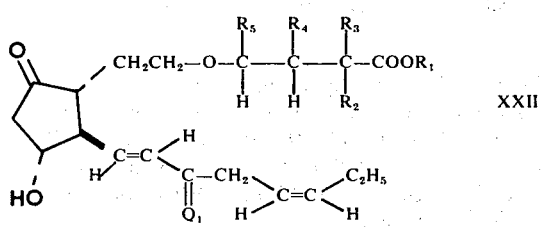

XXII

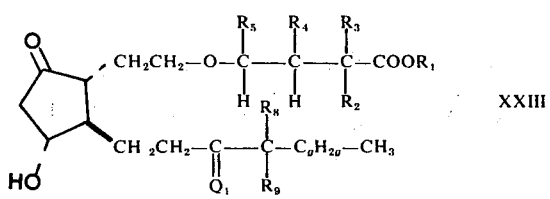

XXIII

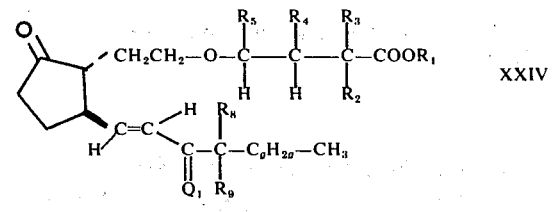

XXIV

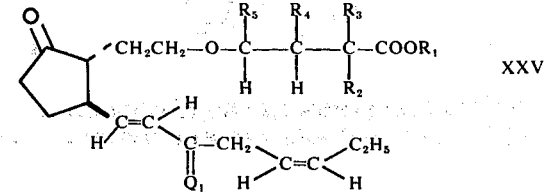

XXV

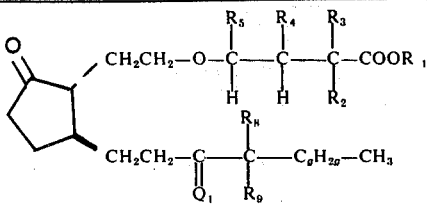 XXVI
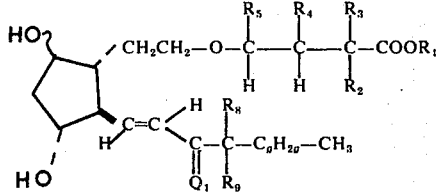 XXVII
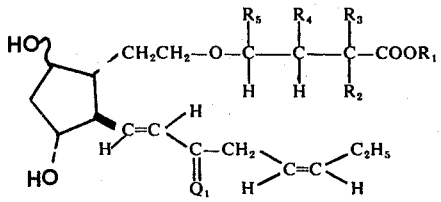 XXVIII
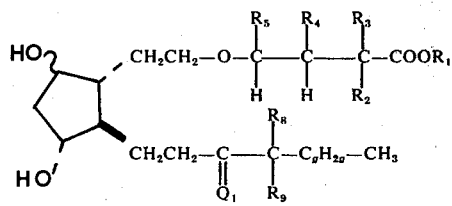 XXIX
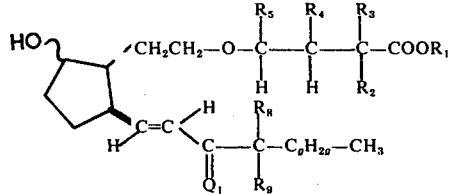 XXX
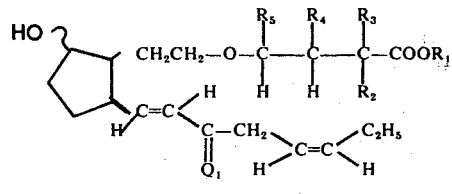 XXXI
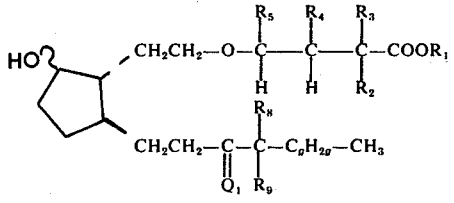 XXXII
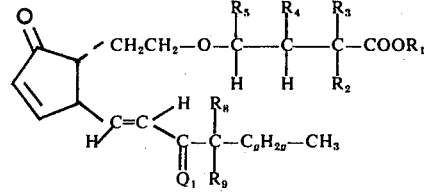 XXXIII
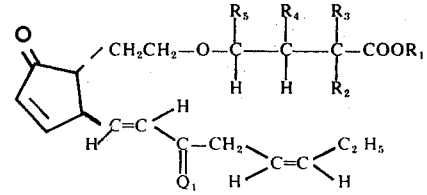 XXXIV

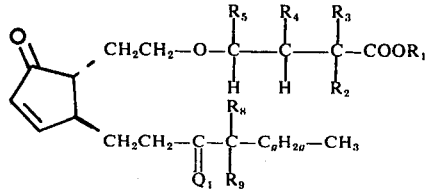 XXXV
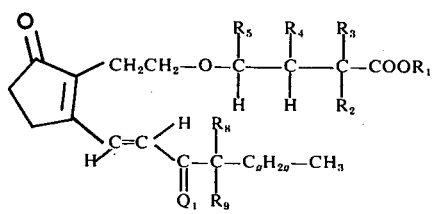 XXXVI
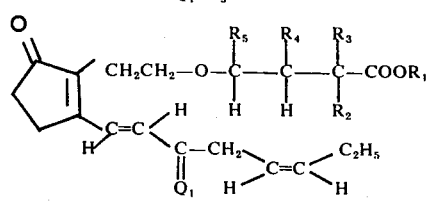 XXXVII
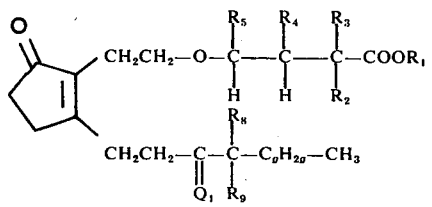 XXXVIII
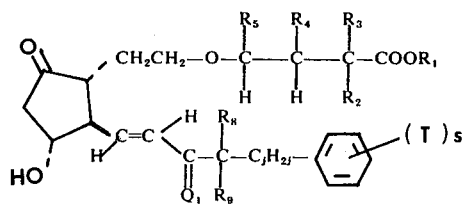 XXXIX
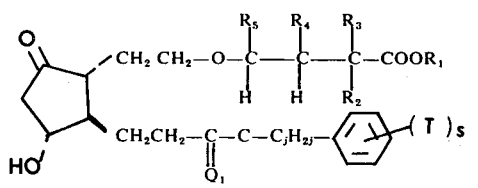 XL
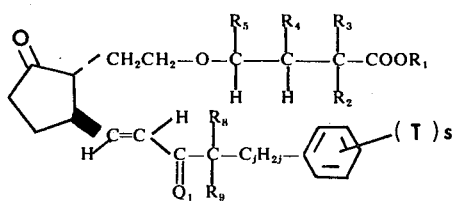 XLI
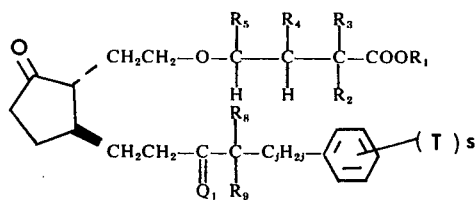 XLII
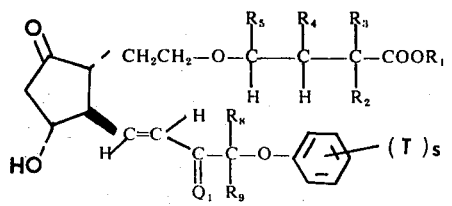 XLIII

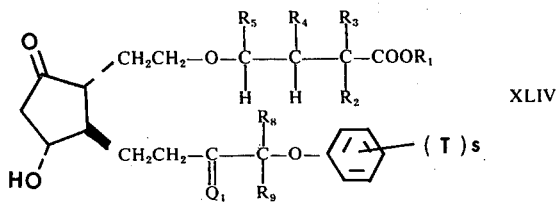 XLIV
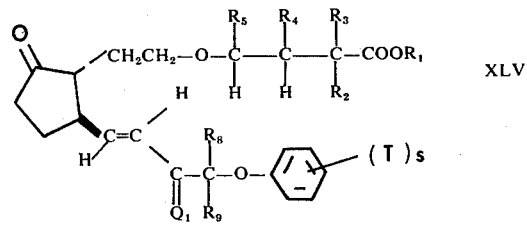 XLV
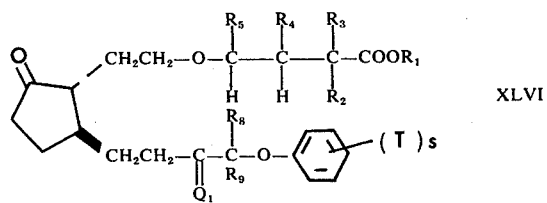 XLVI
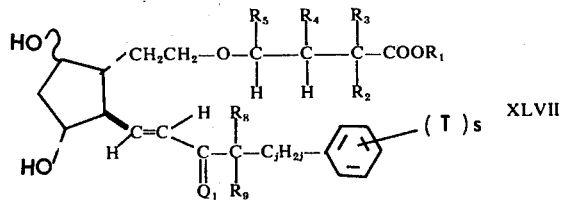 XLVII
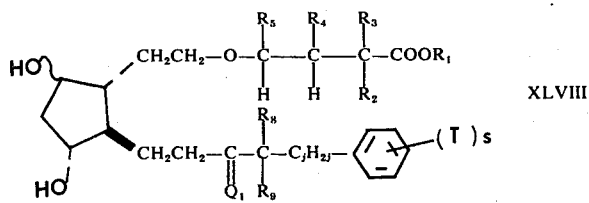 XLVIII
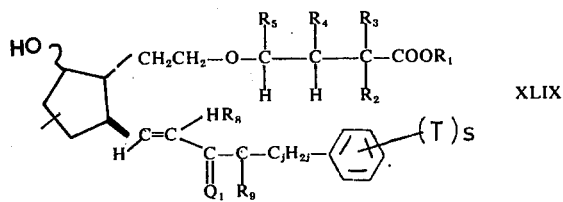 XLIX
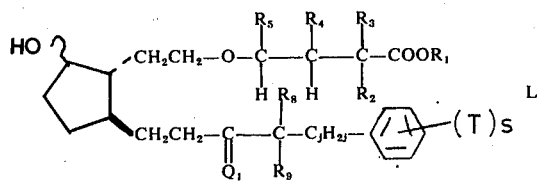 L
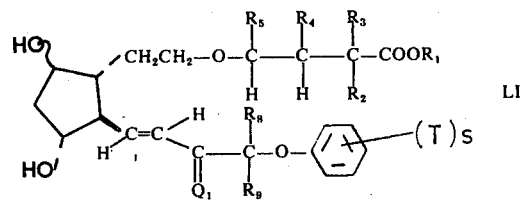 LI

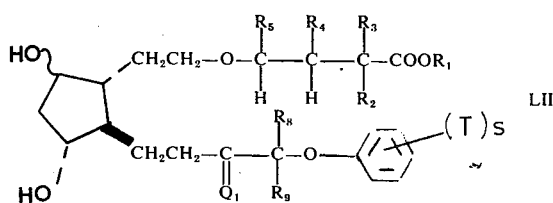 LII
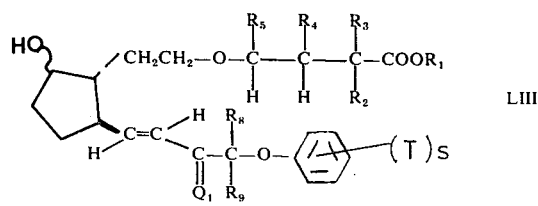 LIII
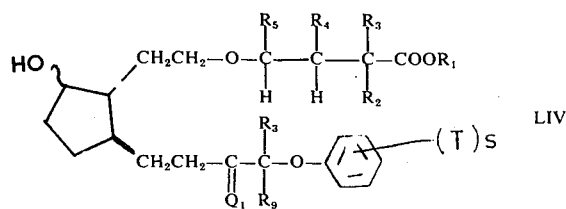 LIV
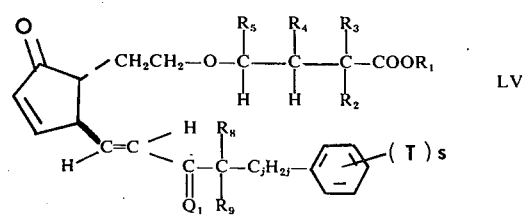 LV
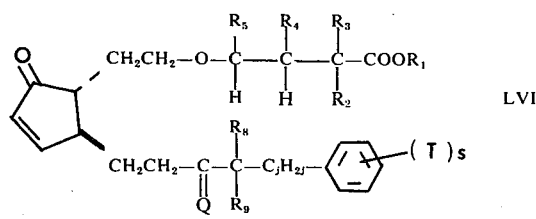 LVI
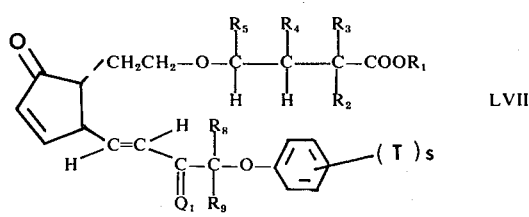 LVII
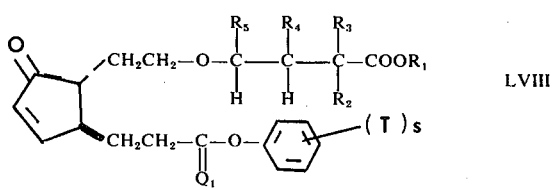 LVIII
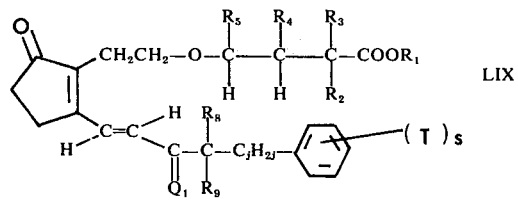 LIX

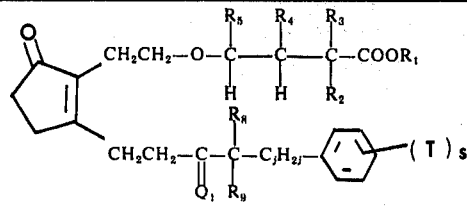

LX

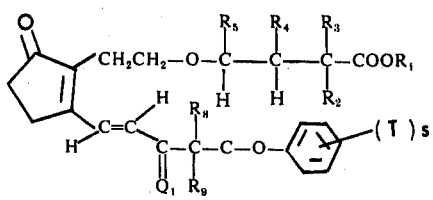

LXI

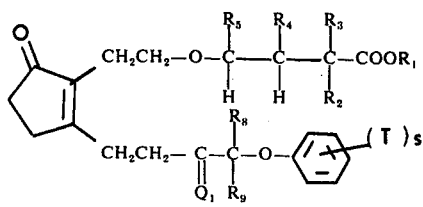

LXII

Formulas XXI to XXVI represent 5-oxa compounds of the PGE and 11-deoxy-PGE types. Formulas XXVII to XXXII represent 5-oxa compounds of the PGF and 11-deoxy-PGF types. Formulas XXXIII to XXXV represent 5-oxa compounds of the PGA type. Formulas XXXVI to XXXVIII represent 5-oxa compounds of the PGB type.

Formulas XXXIX to LXII represent 5-oxa compounds in which there is a benzene or aromatic nucleus. Formulas XXXIX to XLVI represent 5-oxa compounds of the PGE and 11-deoxy-PGE types. Formulas XLVII to LIV represent 5-oxa compounds of the PGF and 11-deoxy-PGF types. Formulas LV to LVIII represent 5-oxa compounds of the PGA type. Formulas LIX to LXII represent 5-oxa compounds of the PGB type.

In formulas XXI to LXII, inclusive, $C_gH_{2g}$ is alkylene of one to 9 carbon atoms, inclusive, with one to 5 carbon atoms, inclusive, in the chain between $-CR_8R_9-$ and terminal methyl. $C_jH_{2j}$ is a valence bond or alkylene of one to 9 carbon atoms, inclusive, substituted with zero, one, or 2 fluoro, with one to 6 carbon atoms, inclusive, between $-CR_8R_9-$ and the ring. $Q_1$ is

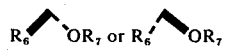

wherein $R_6$ and $R_7$ are hydrogen or alkyl of one to 4 carbon atoms, inclusive, being the same or different. $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive. $R_3$, $R_8$, and $R_9$ are hydrogen, alkyl of one to 4 carbon atoms, inclusive, or fluoro, being the same or different, with the proviso that $R_9$ is fluoro only when $R_8$ is hydrogen or fluoro and with the further proviso that neither $R_8$ nor $R_9$ are fluoro in the compounds containing the

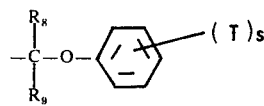

moiety represented by formulas XLIII-XLVI, LI-LIV, LVII, LVIII, LXI, and LXII above. $R_2$ is hydrogen or fluoro, with the proviso that $R_2$ is fluoro only when $R_3$ is hydrogen or fluoro. $R_4$ and $R_5$ are hydrogen or alkyl of one to 4 carbon atoms, inclusive, being the same or different, with the proviso that no more than one of $R_3$, $R_4$, and $R_5$ is alkyl. T is alkyl of one to 4 carbon atoms, inclusive, fluoro, chloro, trifluoromethyl, or $-OR_{10}$, wherein $R_{10}$ is hydrogen or alkyl of one to 4 carbon atoms, inclusive, and s is zero, one, 2, or 3, with the proviso that not more than two T's are other than alkyl. The ~ indicates attachment of hydroxyl to the ring in alpha or beta configuration.

In formulas XXI to LXII wherein there is a $C_{13}-C_{14}$ ethylenic group, for example formulas XXI and XXII, that ethylenic group is in trans configuration. In formulas XXI to LXII wherein there is a $C_{17}-C_{18}$ ethylenic group, for example formulas XXII and XXV, that ethylenic group is in cis configuration.

Those PGF-type compounds represented by formulas XXVII-XXXII and XLVII-LIV wherein the C-9 hydroxyl is attached to the cyclopentane ring with a wavy line ~ include both $PGF_\alpha$ - and $PGF_\beta$ -type compounds.

In all of the compounds represented by formulas XXI-XXXV and XXXIX-LVIII, the carboxyl-terminated side chain is attached to the cyclopentane ring in alpha configuration and the other side chain is attached in beta configuration.

As in the case of formulas II to VI, formulas XXI to LXII wherein $Q_1$ is

, i.e.

wherein the C-15 hydroxyl or ether group is attached to the side chain in alpha configuration, are each intended to represent optically active prostanoic acid derivatives with the same absolute configuration as $PGE_1$ obtained from mammalian tissues.

Also included within this invention are the 15-epimer compounds of formulas XXI to LXII wherein $Q_1$ is

These are identified hereinafter as "15-epi", "15β", or "15(R)" compounds by the appropriate prefix in the name. For example, "15-epi-5-oxa-PGE$_1$" identifies the 15-epimeric compound corresponding to the formula-VIII example above except that it has the beta configuration at C-15 instead of the natural alpha configuration of 5-oxa-PGE$_1$. As is known in the art "R" and "S" designation depends on the neighboring substituents. See R. S. Cahn, J. Chem. Ed. 41, 116 (1964).

Included with this invention are both optically active enantiomorphs i.e. not only that isomer having the natural configuration, as represented by the formula herein, but also its enantiomer as represented by the mirror image of that formula, and also the racemic compound, comprising both isomers. The racemic compound is properly represented by two formulas, one as drawn herein and the other as its mirror image. Such a racemic compound is designated herein by the prefix "racemic" ("rac-" or "dl-") before its name; when that prefix is absent, the intent is to designate an optically active compound represented by the appropriate formula XXI to LXII. For convenience in the charts herein, only a single structural formula is used, for example in Chart B, to define not only the optically active form but also the racemic compound which generally undergoes the same reactions.

With regard to formulas XXI to LXII, examples of alkyl of one to 4 carbon atoms, inclusive, are methyl, ethyl, propyl, butyl, and isomeric forms thereof. Examples of alkyl of one to 12 carbon atoms, inclusive, are those given above, and pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butyl-cyclopropyl, cyclobutyl, 2-methylcyclobutyl, 3-propyl-cyclobutyl, 2,3,4-triethylcyclobutyl, cyclopentyl, 2,2-dimethylcyclopentyl, 2-pentylcyclopentyl, 3-tert-butyl-cyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are (o-, m-, or p-)chlorophenyl, 2,4-dichlorophenyl, 2,4,6-trichlorophenyl, (o-, m-, or p-)tolyl, p-ethylphenyl, p-tert-butylphenyl, 2,5-dimethylphenyl, 4-chloro-2-methylphenyl, and 2,4-dichloro-3-methylphenyl.

Examples of alkylene of one to 9 carbon atoms, inclusive, with one to 5 carbon atoms inclusive, in the chain, within the scope of C$_g$H$_{2g}$ as defined above, are methylene, ethylene, trimethylene, tetramethylene, and pentamethylene, and those alkylene with one or more alkyl substituents on one or more carbon atoms thereof, e.g. —CH(CH$_3$)—, —C(CH$_3$)$_2$—, —CH(CH$_2$CH$_3$)—, —CH$_2$-CH(CH$_3$)—, —CH(CH$_3$)—CH(CH$_3$)—, —CH$_2$—C(CH$_3$)$_2$—, —CH$_2$—CH(CH$_3$)—CH$_3$—, —CH$_2$—CH$_2$—CH(CH$_2$CH$_2$CH$_3$)—, —CH(CH$_3$)—CH(CH$_3$)—CH$_2$—CH$_2$—, —CH$_2$—CH$_2$—CH$_2$—C(CH$_3$)$_2$—CH$_2$, and —CH$_2$—CH$_2$—CH$_2$—CH(CH$_3$)—. Examples of alkylene of one to 9 carbon atoms, inclusive, substituted with zero, one, or 2 fluoro, with one to 6 carbon atoms in the chain, within the scope of C$_j$H$_{2j}$ as defined above, are those given above for C$_g$H$_{2g}$ and hexamethylene, including hexamethylene with one or more alkyl substituents on one or more carbon atoms thereof, and including those alkylene groups with one or 2 fluoro substituents on one or 2 carbon atoms thereof, e.g. —CHF—CH$_2$—, —CHF—CHF—, —CH$_2$—CH$_2$—CF$_2$—, —CH$_2$—CHF—CH$_2$—, —CH$_2$—CH$_2$—CF(CH$_3$)—, —CH$_2$—CH$_2$—CF$_2$—CH$_2$—, —CH(CH$_3$)—CH$_2$—CH$_2$—CHF—, —CH$_2$—CH$_2$—CH$_2$—CH$_2$—CF$_2$—, —CHF—CH$_2$—CH$_2$—CH$_2$—CH$_2$—CHF—, —CF$_2$—CH$_2$—CH$_2$—CH$_2$—CH$_2$—CH$_2$—, —CH$_2$—CH $_2$—CH$_2$—CF$_2$—CH$_2$—CH$_2$—, and —CH$_2$—CH$_2$—CH$_2$—CH$_2$—CH$_2$—CF$_2$.

Examples of

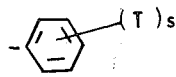

as defined above are phenyl, (o-, m-, or p-)tolyl, (o-, m-, or p-)ethylphenyl, (o-, m-, or p-) propylphenyl, (o-, m-, or p-)butylphenyl, (o-, m-, or p-)isobutylphenyl, (o-, m-, or p-)tert-butylphenyl, 2,3-xylyl, 2,4-xylyl, 2,5-xylyl, 2,6-xylyl, 3,4-xylyl, 2,6-diethylphenyl, 2-ethyl-p-tolyl, 4-ethyl-o-tolyl, 5-ethyl-m-tolyl, 2-propyl-(o-, m-, or p-)tolyl, 4-butyl-m-tolyl, 6-tert-butyl-m-tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, α,α,α-trifluoro-(o-, m-, or p-)tolyl, (o-, m-, or p-)methoxyphenyl, (o-, m-, or p-)ethoxyphenyl, (4- or 5-)chloro-2-methoxyphenyl, and 2,4-dichloro-(5- or 6-)methoxyphenyl.

The novel formula XXI-to-LXII compounds and the racemic compounds of this invention each cause the biological responses described above for the PGE, PGF$_α$, PGF$_β$, and PGA compounds, respectively, and each of these novel compounds is accordingly useful for the above-described corresponding purposes, and is used for those purposes in the same manner as described above.

The known PGE, PGF$_α$, PGF$_β$, PGA and PGB compounds are all potent in causing multiple biological responses even at low doses. For example, PGE$_1$ and PGE$_2$ both cause vasodepression and smooth muscle stimulation at the same time they exert antilipolytic activity. Moreover, for many applications, these known prostaglandins have an inconveniently short duration of biological activity. In striking contrast, the novel prostaglandin analogs of formulas XXI-to-LXII and the corresponding racemic compounds are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

Because of their unique chemical structure, the novel 11-deoxy-PGE and 11-deoxy-PGF analogs of this invention of formulas XXIV-XXVI, XXX-XXXII, XLI, XLII, XLV, XLVI, XLIX, L, LIII, and LIV are less sensitive to chemical change than the prostaglandins and enjoy increased chemical stability and longer shelf life.

To obtain the optimum combination of biological response specificity, potency, and duration of activity, certain compounds within the scope of formulas XXI-to-LXII are preferred. With reference to the definitions given above, it is preferred that $C_gH_{2g}$ be straight chain of one to 5 carbon atoms, inclusive. It is especially preferred that $C_gH_{2g}$ be trimethylene. It is further preferred that $Q_1$ be

It is also preferred that the sum of the carbon atoms in $R_6$ and $R_7$, when alkyl, be not greater than 7, and that the sum of the carbon atoms in $R_6$, $R_7$, $R_8$, and $R_9$ taken together is not greater than 7. Another preference is that if one or more of $R_3$, $R_4$, $R_5$, $R_8$, or $R_9$ is alkyl, that it be methyl or ethyl. It is especially preferred that if $R_4$ or $R_5$ is alkyl that it be methyl.

In compounds XXXIX-to-LXII, it is preferred that $C_jH_{2j}$ be straight chain of one to 4 carbon atoms, inclusive. It is especially preferred that $C_jH_{2j}$ be methylene. It is further preferred that if T is alkyl that it be methyl, and that if T is $-OR_{10}$ that $R_{10}$ be methyl. It is also preferred that, if s is not zero, the phenyl ring be substituted at least at the para position.

Another advantage of the novel compounds of this invention, especially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 5-oxa prostaglandin analogs encompassed by formulas XXI-to-LXII including their alkanoates, are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these formula XXI-to-LXII compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)-diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds encompassed by formulas XXI-to-LXII are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of formulas XXI-to-LXII are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that $R_1$ in the formula XXI-to-LXII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers, are used for oral sublingual administration. For rectal or vaginal administration, suppositories prepared as known in the art are used. For tissue implants, a sterile tablet or silicone rubber capsule or other object containing or impregnated with the substance is used.

The 5-oxa prostaglandin analogs encompassed by formulas XXI through LXII are produced by the reactions and procedures described and exemplified hereinafter.

Reference to Charts A and B herein will make clear the process steps starting in Chart A with the iodolactone of formula LXIII to provide the lactol of formula LXXII, and in Chart B, the transformation of the more general lactone of formula LXXIII to yield the 5-oxa PGF-type compounds of formula LXXVI.

CHART A

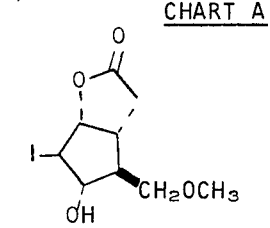 LXIII

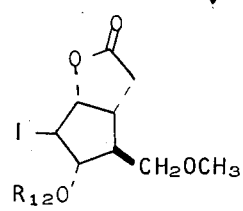 LXIV

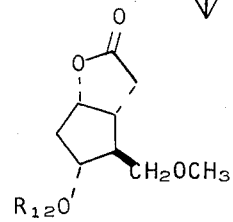 LXV

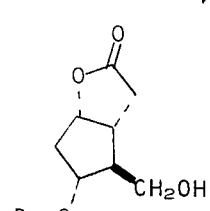 LXVI

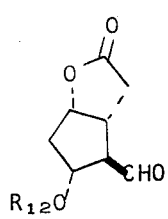 LXVII

CHART A -continued

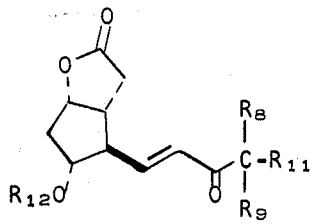 LXVIII

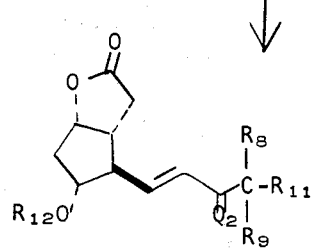 LXIX

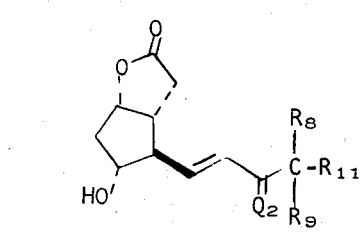 LXX

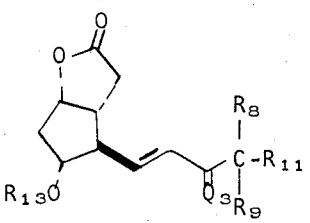 LXXI

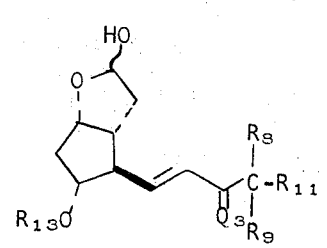 LXXII

CHART B

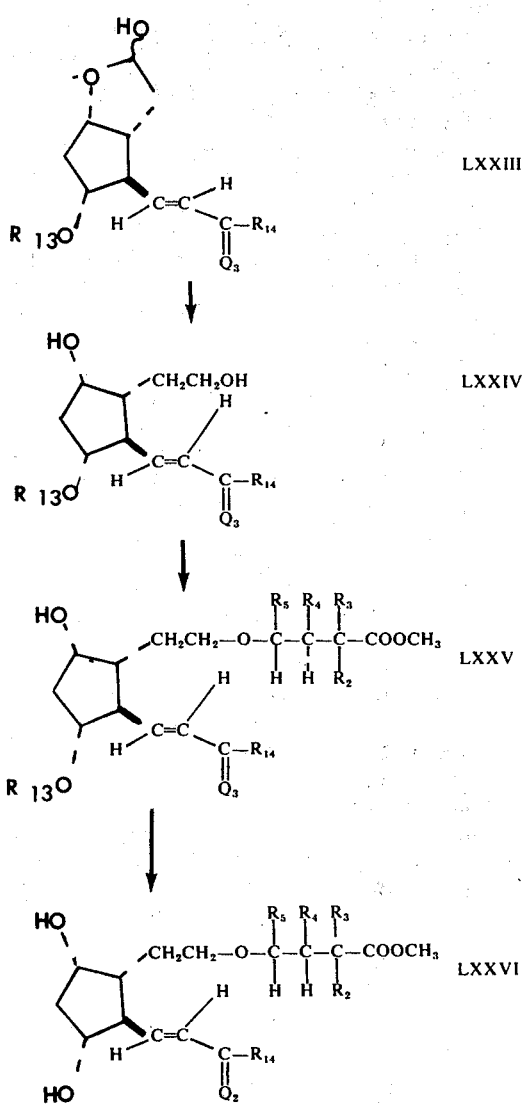

In Chart A, $R_8$ and $R_9$ have the same meaning as above, i.e. $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro. $R_{11}$ is (1)  (2)

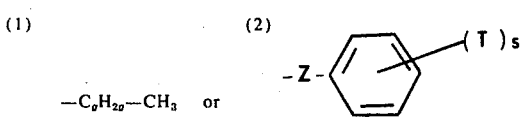

—$C_gH_{2g}$—$CH_3$   or wherein $C_gH_{2g}$ is alkylene of one to 9 carbon atoms, inclusive, with one to 5 carbon atoms, inclusive, in the chain between —$CR_8R_9$— and terminal methyl; wherein $R_8$ and $R_9$ are as defined above; wherein T is alkyl of one to 4 carbon atoms, inclusive, fluoro, chloro, trifluoromethyl, or —$OR_{10}$, wherein $R_{10}$ is hydrogen or alkyl of one to 4 carbon atoms, inclusive, and s is zero, one, 2, or 3, with the proviso that not more than two T's are other than alkyl; and wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive between —$CR_8R_9$— and the ring. $R_{12}$ is (1)

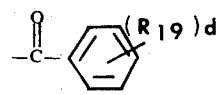

wherein $R_{19}$ is alkyl of one to 4 carbon atoms, inclusive, phenylalkyl of 7 to 10 carbon atoms, inclusive, or nitro, and d is zero to 5, inclusive, provided that not more than two $R_{19}$'s are other than alkyl, and that the total number of carbon atoms in the $R_{19}$'s does not exceed 10 carbon atoms;

(2)

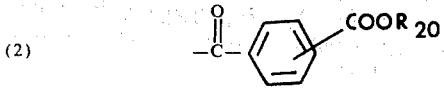

wherein $R_{20}$ is alkyl of one to 4 carbon atoms, inclusive;

(3) 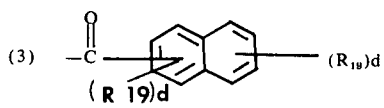

wherein $R_{19}$ and d are as defined above; or (4) acetyl. Use of acetyl or p-phenylbenzoyl is known in the art. See Corey et al., J. Am. Chem. Soc. 93, 1491 (1971).

Likewise in Chart A, $R_{13}$ is a "blocking group", which is defined as any group which replaces hydrogen of the hydroxyl groups, which is not attacked by nor is reactive to the reagents used in the respective transformations to the extent that the hydroxyl group is, and which is subsequently replaceable by hydrogen at a later stage in the preparation of the prostaglandin-like products. Several blocking groups are known in the art, e.g. tetrahydropyranyl and substituted tetrahydropyranyl (see Corey, Proceedings of the Robert A. Welch Foundation Conferences on Chemical Research. XII, Organic Synthesis, pp. 51–79 (1969)). Those blocking groups which have been found useful include (a) tetrahydropyranyl; (b) tetrahydrofuranyl; or (c) a group of the formula

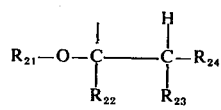

wherein $R_{21}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{22}$ and $R_{23}$ are the same or different, being hydrogen, alkyl of one to 4 carbon atoms, inclusive, phenyl or phenyl substituted with one, 2, or 3 alkyl of one to 4 carbon atoms, inclusive, or, when $R_{22}$ and $R_{23}$ are taken together, $-(CH_2)a-$ or $-(CH_2)b-O-(CH_2)c-$ wherein $a$ is 3, 4, or 5, $b$ is one, 2, or 3, and $c$ is one, 2, or 3 with the proviso that $b$ plus $c$ is 2, 3, or 4, and wherein $R_{24}$ is hydrogen or phenyl.

Further in Chart A, $Q_2$ is either

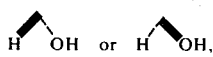

$Q_3$ is

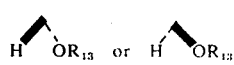

wherein $R_{13}$ is a blocking group as defined above, and ~ indicates attachment of hydroxyl to the ring in alpha or beta configuration.

The iodolactone of formula LXIII is known in the art. See for example E.J. Corey et al., J. Am. Chem. Soc. 91, 5675 (1969) and 92, 397 (1970). It is available in either racemic or optically active (+ or −) form. For racemic products, the racemic form is used. For optically active products having the same configuration as the naturally occurring prostaglandins, the laevorotatory (−) form is used.

In preparing the formula-LXIV compound by replacing the hydrogen of the hydroxyl group in the 4-position with the acyl group $R_{12}$, methods known in the art are used. Thus, an aromatic acid of the formula $R_{12}OH$, wherein $R_{12}$ is as defined above, for example benzoic acid, is reacted with the formula-LXIII compound in the presence of a dehydrating agent, e.g. sulfuric acid, zinc chloride, or phosphoryl chloride; or an anhydride of the aromatic acid of the formula $(R_{12})_2O$, for example benzoic anhydride, is used.

Preferably, however, an acyl halide, e.g. $R_{12}Cl$, for example benzoyl chloride, is reacted with the formula-LXIII compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°–60° C., contacting the reactants in a liquid medium, e.g. excess pyridine or an inert solvent such as benzene, toluene or chloroform. The acylating agent is used either in stoichiometric amount or in excess.

As examples of reagents providing $R_{12}$ for the purposes of this invention, the following are available as acids ($R_{12}OH$), anhydrides (($R_{12})_2O$), or acyl chlorides ($R_{12}Cl$): benzoyl; substituted benzoyl, e.g. (2-, 3-, or 4-)methylbenzoyl, (2-, 3-, or 4-)ethylbenzoyl, (2-, 3-, or 4-)isopropylbenzoyl, (2-, 3-, or 4-)tere-butylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-,3-, or 4-)toluyl, 2-,3-, or 4-phenethylbenzoyl, 2-, 3-, or 4-nitrobenzoyl, (2,4-, 2,5-, or 3,5-)dinitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

isophthaloyl, e.g.

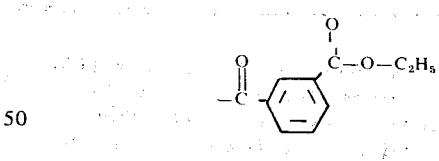

or terephthaloyl, e.g.

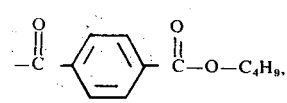

(1- or 2-)naphthoyl; and substituted naphthoyl, e.g. (2-, 3-, 4-, 4-, 6-, or 7-)-methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)-nitro-1-naphthoyl, 4,5-dinitro-1-naphthoyl, (3-, 4-, 6-, 7- or 8-)methyl-1-naphthoyl, 4-ethyl-2-naphthoyl, and (5 -or 8-)nitro-2-naphthoyl. There may be employed, therefore, benzoyl chloride, 4-nitrobenzoyl chloride, 3,5- dinitrobenzoyl chloride, and the like, i.e. $R_{12}Cl$ compounds corresponding to the above $R_{12}$ groups. If the acyl chloride is not available, it is made from the corresponding acid and phosphorus pentachloride as is known in the art. It is preferred that the $R_{12}OH$, $(R_{12})_2O$, or $R_{12}Cl$ reactant does not have bulky, hindering substituents, e.g. tert-butyl, on both of the ring carbon atoms adjacent to the carbonyl attaching-site.

The formula-LXV compound is next obtained by deiodination of LXIV using a reagent which does not react with the lactone ring or the $OR_{12}$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis-(2-methylpropionitrile) as initiator.

The formula-LXVI compound is obtained by demethylation of LXV with a reagent that does not attack the $OR_{12}$ moiety, for example boron tribromide or trichloride. The reaction is carried out preferably in an inert solvent at about 0°–5° C.

The formula-LXVII compound is obtained by oxidation of the —$CH_2OH$ of LXVI to —CHO, avoiding decomposition of the lactone ring. Useful for this purpose are dichromatesulfuric acid, Jones reagent, lead tetraacetate, and the like. Especially preferred is Collins' reagent (pyridine-$CrO_3$) at about 0°–10° C.

The formula-LXVIII compound is obtained by Wittig alkylation of LXVII, using the sodio derivative of an appropriate dimethyl 2-oxoalkylphosphonate within the scope of

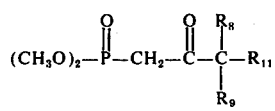

wherein $R_8$, $R_9$, and $R_{11}$ are as defined above. The trans enone lactone is obtained stereospecifically (see D.H. Wadsworth et al, J. Org. Chem. Vol 30, p. 680 (1965)).

The formula-LXIX compound is obtained as a mixture of alpha and beta hydroxy isomers by reduction of LXVIII. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy) aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane (bis-3-methyl-2-butylborane). For production of natural-configuration prostaglandins, the alpha form of the formula-LXIX compound is separated from the beta isomer by silica gel chromatography using methods known in the art.

The formula-LXX compound is then obtained by deacylation of LXIX with an alkali metal carbonate, for example potassium carbonate in methanol at about 25° C.

The formula-LXXI lactone is obtained by replacing the hydrogen atoms of the hydroxyl groups of LXX with a blocking group. When the blocking group is tetrahydropyranyl or tetrahydrofuranyl, the appropriate reagent, e.g. 2,3-dihydropyran or 2,3-dihydrofuran, is used in an inert solvent such as dichloromethane, in the presence of an acid condensing agent such as p-toluenesulfonic acid or pyridine hydrochloride. The reagent is used in slight excess, preferably 1.0 to 1.2 times theory. The reaction is carried out at about 20°–50° C.

When the blocking group is of the formula

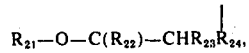

as defined above, the appropriate reagent is a vinyl ether, e.g. isobutyl vinyl ether or any vinyl ether of the formula $R_{21}$—O—$C(R_{22})$=$CR_{23}R_{24}$ wherein $R_{21}$, $R_{22}$, $R_{23}$, and $R_{24}$ are as defined above; or an unsaturated cyclic or heterocyclic compound, e.g. 1-cyclohex-1-yl methyl ether

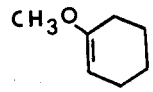

or 5,6-dihydro-4-methoxy-2H-pyran

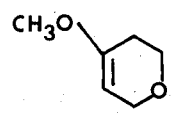

See C.B. Reese et al., J. Am. Chem. Soc. 89, 3366 (1967). The reaction conditions for such vinyl ethers and unsaturates are similar to those for dihydropyran above.

The formula-LXXII lactol is obtained on reduction of lactone LXXI without reducing the ethylenic group. For this purpose, diisobutylaluminum hydride is used as known in the art. The reduction is preferably done at −60° to −70° C.

The stereochemistry of the side chain is preserved in transforming LXIX to LXX to LXXI to LXXII. For example a 3-alpha compound LXIX yields a 3-alpha compound LXXII.

The preparation of lactol LXXII with specific embodiments of $R_8$, $R_9$, $R_{11}$, and $R_{13}$ was reported by E. J. Corey et al., first in racemic form in J. Am. Chem. Soc. 91, 5675 (1969) and later in optically active form in J. Am. Chem. Soc. 92, 397 (1970).

Referring to Chart B, there are shown the novel steps of this invention whereby lactol LXXIII is transformed to a 5-oxa $PGF_\alpha$ -type product LXXVI.

In Chart B, the terms $R_2$, $R_3$, $R_4$, $R_5$, $R_{13}$, $Q_2$, $Q_3$, and ~ have the same meaning as in Chart A. $R_{14}$ includes

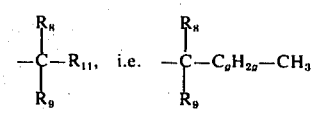

and

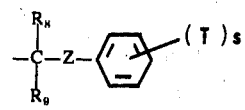

as defined above and also the group

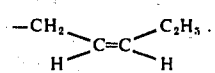

Intermediate lactol LXXIII includes lactol LXXII of Chart A and also lactols of the formula

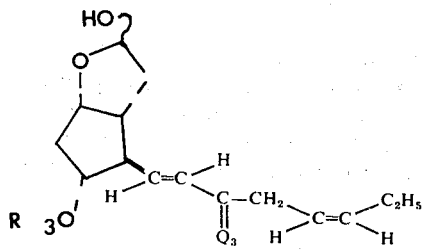

CXI

For the compound wherein $R_{13}$ is tetrahydropyranyl, see Corey et al., J. Am. Chem. Soc. 93, 1490 (1971). Preparation of similar formula-LXXIII compounds is by known methods.

Alcohol LXXIV is obtained on reduction of lactol LXXIII, for example with aqueous methanolic or ethanolic sodium borohydride. Alternatively and preferably, alcohol LXXIV is obtained by one-step reduction of a formula-LXXI lactone, for example with lithium aluminum hydride or diisobutylaluminum hydride at 0°–35° C.

For preparing the formula-LXXV compound, a Williamson synthesis is employed. For example, the formula-LXXIV alcohol is condensed with a halobutyrate or appropriate haloester within the scope of Hal

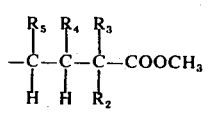

wherein Hal is chloro, bromo, or iodo and $R_2$, $R_3$, $R_4$, and $R_5$ are as defined above. Normally the reaction is done in the presence of a base such as n-butyllithium, phenyllithium, triphenylmethyllithium, sodium hydride, or potassium t-butoxide. Alternatively and preferably, an ortho-4-bromobutyrate within the scope of

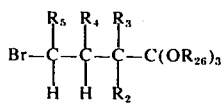

wherein $R_{26}$ is alkyl of one to 3 carbon atoms, inclusive, and $R_2$, $R_3$, $R_4$, and $R_5$ are as defined above, is employed. Such reagents are available or prepared by methods known in the art, for example from the appropriate halonitrile by way of the corresponding imino ester hydrohalide as illustrated hereinafter. The condensation is conveniently run in a solvent such as tetrahydrofuran or dimethyl sulfoxide, or especially if an organolithium compound is employed, preferably in dimethyl formamide or hexamethylphosphoramide. The reaction proceeds smoothly at −20° to 50° C., but is preferably done at about 25° C. for convenience. Following the condensation, the formula-LXXV compound is obtained by methods known in the art, for example by hydrolysis in cold dilute mineral acid.

The 5 oxa $PGF_\alpha$ -type product LXXVI is obtained from the LXXV intermediate by hydrolysis of the blocking groups for example in dilute acetic acid, aqueous citric acid, or aqueous phosphoric acid-tetrahydrofuran.

Referring to Chart C, there is shown the transformation of the LXXV intermediates of Chart B to the formula-LXXVII PGE-type products or the formula-LXXVIII $PGF_\alpha$ and -LXXIX $PGF_\beta$ type products. In Chart C, the terms $R_2$, $R_3$, $R_4$, $R_5$, $R_{13}$, $R_{14}$, $Q_2$, and $Q_3$ are as defined above; $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive. The steps by which LXXV is transformed to LXXVII depends on whether $R_1$ is methyl or other group or hydrogen. If $R_1$ is methyl, the procedure is simply to oxidize the C-9 position and then replace the blocking groups with hydrogen.

CHART C

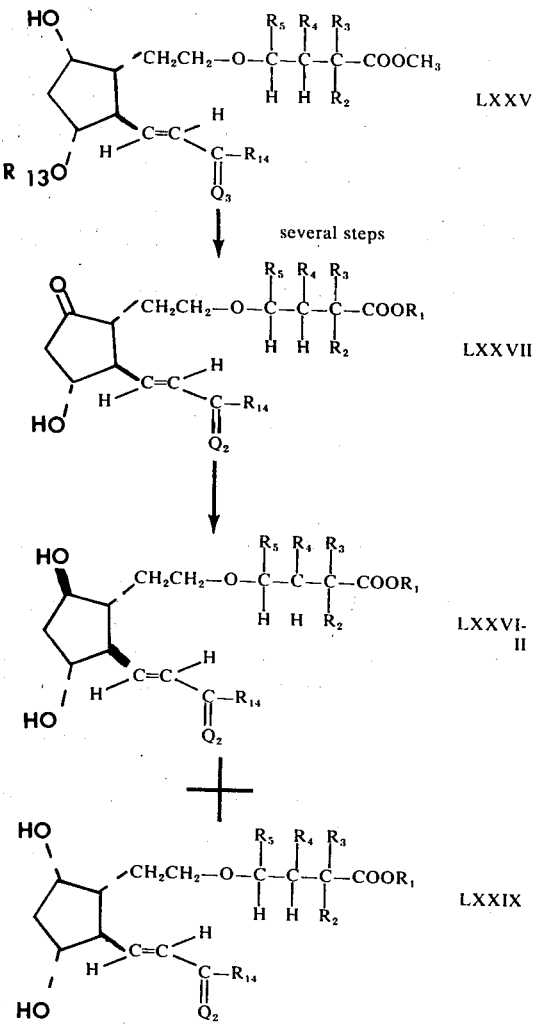

Oxidation reagents useful for this transformation are known in the art. A useful reagent for this purpose is the Jones reagent, i.e., acidified chromic acid. See J. Chem. Soc. 39 (1946). A slight excess beyond the amount necessary to oxidize the C-9 secondary hydroxy groups of the formula-LXXV reactant is used. Acetone is a suitable diluent for this purpose. Reaction temperatures at least as low as about 0° C. should be used. Preferred reaction temperatures are in the range 0° to −50° C. An especially useful reagent for this purpose is the Collins reagent, i.e. chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

Examples of other oxidation reagents useful for this transformation are silver carbonate on Celite (Chem. Commun. 1102 (1969)), mixtures of chromium trioxide and pyridine J. Am. Chem. Soc. 75, 422 (1953), and Tetrahedron, 18, 1351 (1962)), t-butylchromate in pyridine (Biochem. J., 84, 195 (1962)), mixtures of sulfur trioxide in pyridine and dimethylsulfoxide (J. Am. Chem. Soc. 89, 5505 (1967)), and mixtures of dicyclohexylcarbodiimide and dimethyl sulfoxide (J. Am. Chem. Soc. 87, 5661 (1965)).

The formula-LXXVII 5-oxa PGE-type compound is then obtained by hydrolysis of the blocking groups, for example in dilute acetic acid.

If $R_1$ in the desired formula-LXXVII product is to be hydrogen or a different group than methyl, the formula-LXXV intermediate is hydrolyzed or saponified under alkaline conditions by the usual known procedures and recovered in the free acid form. This acid intermediate is either subjected to the oxidation and hydrolysis steps above to yield LXXVII in acid form ($R_1$ is hydrogen) or it is converted to the desired ester, for example with a diazoalkane or by other methods described herein, and then transformed by oxidation and hydrolysis to product LXXVII.

Continuing with Chart C, the formula-LXXVIII PGF$_\beta$-type products are obtained by carbonyl reduction of the corresponding formula-LXXVII PGE$_2$-type compounds. There are obtained in the same reaction the corresponding formula-LXXIX PGF$_\alpha$-type compounds. For example, carbonyl reduction of 5-oxa-PGE$_1$ gives a mixture of 5-oxa-PGF$_{1\alpha}$ and 5-oxa-PGF$_{1\beta}$.

These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16,969 (1962), and British Specification No. 1,097,533. Any reducing agent is used which does not react with carbon-carbon double bonds or ester groups. Preferred reagents are lithium (tri-tert-butoxy)aluminum hydride, the metal borohydrides, especially sodium, potassium and zinc borohydrides, and the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are column chromatography, partition chromatographic procedures, both normal and reversed phase, preparative thin layer chromatography, and countercurrent distribution procedures.

Referring to Chart D, there is shown the transformation of lactone LXXX to 5-oxa 15-alkyl ether PGF-type products of formula LXXXIII. In Chart D, $R_2$, $R_3$, $R_4$, $R_5$, $R_{13}$, $R_{14}$, $Q_2$, and ~ have the same meanings as above. $Q_4$ is either

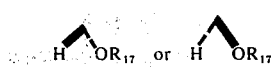

wherein $R_{17}$ is alkyl of one to 4 carbon atoms, inclusive. The starting materials are available from the steps of Chart A above or are readily available by methods known in the art.

The formula-LXXXI compound is prepared by alkylation of the side-chain hydroxy of the formula-LXXX compound thereby replacing hydroxy with the —$OR_{17}$ moiety. For this purpose, diazoalkanes may be employed, preferably in the presence of a Lewis acid, e.g. boron trifluoride etherate, aluminum chloride, or fluoboric acid. When $R_{17}$ is methyl, diazomethane is used. See Fieser et al., "Reagents for Organic Synthesis", John Wiley and Sons, Inc., N.Y. (1967), p. 191. Other —$OR_{17}$ groups are formed by using the corresponding diazoalkane. For example diazoethane and diazobutane yield —$OC_2H_5$ and —$OC_4H_9$ respectively. The reaction is carried out by mixing a solution of the diazoalkane in a suitable inert solvent, preferably ethyl ether, with the formula-LXXX compound.

CHART D

LXXX

LXXXI

LXXXII several steps

CHART D-continued

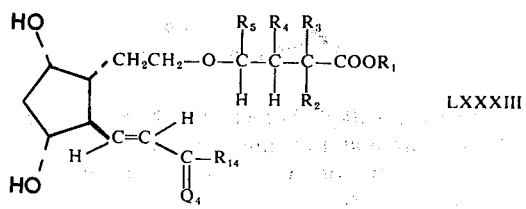

LXXXIII

Generally the reaction proceeds at about 25° C. Diazoalkanes are known in the art or can be prepared by methods known in the art. See, for example, Organic Reactions, John wiley and Sons, Inc., N.Y. Vol. 8, pp. 389–394 (1954).

Another method for the alkylation of the side chain hydroxy is by reaction with an alcohol in the presence of boron trifluoride etherate. Thus, methanol and boron trifluoride etherate yield the methyl ether wherein $R_{17}$ is methyl. The reaction is done at about 25° C. and is conveniently followed with thin layer chromatography (TLC).

Another method for the alkylation of the side-chain hydroxy is by the reaction of an alkyl halide, e.g. methyl iodide, in the presence of a metal oxide or hydroxide, e.g. barium oxide, silver oxide, or barium hydroxide. An inert solvent may be beneficial, for example benzene or dimethylformamide. The reactants are preferably stirred together and maintained at temperatures of 25°–75° C.

Still another method is by first converting the hydroxy to mesyloxy (i.e. methanesulfonate) or tosyloxy (i.e. toluenesulfonate) and thence transforming the mesyloxy or tosyloxy to the $-OR_{17}$ moiety by reaction with a metal alkoxide, e.g. potassium tert-butoxide. The mesylate or tosylate is prepared by reaction of the formula-LXXX intermediate with either methanesulfonyl chloride or toluenesulfonyl chloride in pyridine. Thereafter, the mesylate or tosylate is mixed with the appropriate potassium or sodium alkoxide in pyridine, the reaction proceeding smoothly at about 25° C. An equivalent amount of the alkoxide based on the mesylate is preferred to avoid side reactions. In this manner, the formula-LXXXI intermediate is prepared wherein $R_{17}$ is normal alkyl, secondary alkyl, or tertiary alkyl of one to 5 carbon atoms. The method is especially useful for tertiary alkyl substitutions for hydrogen, e.g. where $R_{17}$ is tert-butyl or tert-pentyl.

The formula-LXXXII compound is then obtained in the conventional manner, for example by low temperature reduction with disobutylaluminum hydride as discussed above for Chart A. The final 5-oxa 15-alkyl ether PGF$_\alpha$ product LXXXIII is obtained from either LXXXI or LXXXII by the same reactions and conditions discussed above for the steps of Chart B.

Referring to Chart E, there is shown the transformation of lactone LXVIII to lactol LXXXVII useful for preparing 5-oxa-15-alkyl-PG-type products. In Chart E, $R_8$, $R_9$, $R_{11}$, $R_{12}$, $R_{13}$ and ~ are as defined above for Chart A. $Q_5$ is either

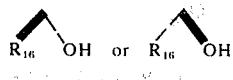

wherein $R_{16}$ is alkyl of one to 4 carbon atoms, inclusive. $Q_6$ is either

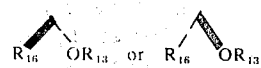

wherein $R_{13}$ and $R_{16}$ are as defined above.

For the starting material LXVIII refer to Chart A and the discussion pertaining thereto. Intermediate LXXXIV is obtained by replacing the side-chain oxo with $Q_5$ by a conventional Grignard reaction, employing $R_{16}$MgHal. Next, the acyl group $R_{12}$ is removed by hydrolysis and the hydrogen atoms of the hydroxyl groups are replaced with blocking groups $R_{13}$ following the procedures of Chart A. Finally lactol LXXXVII is obtained by reduction of lactone LXXXVI in the same manner discussed above for Charts A and D.

The 15-alkyl products of this invention are obtained from lactone LXXXVI either with or without isolating the formula-LXXXVII lactol, following the procedures discussed above for chart B.

CHART E

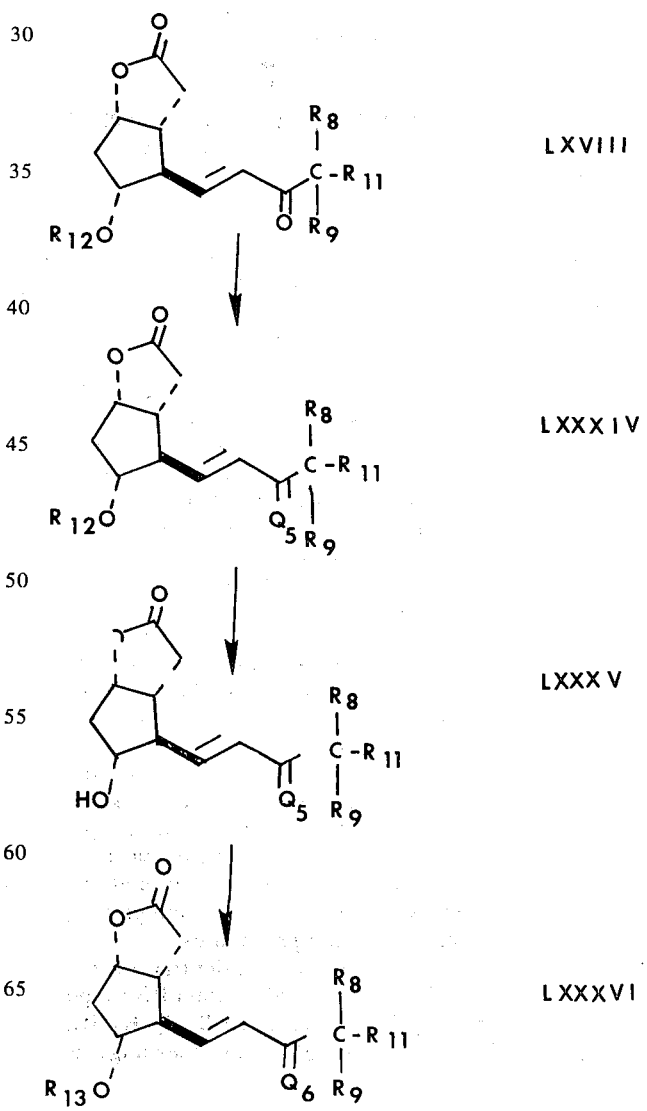

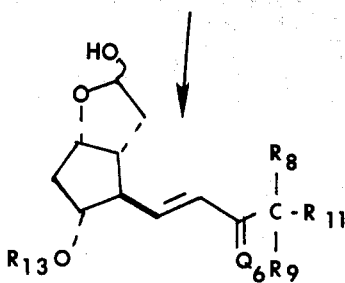

LXXXVII

The 15-R and 15-S isomers are separated by conventional means, for example silica gel chromatography at either the lactol or the final product stages.

Referring to Chart F, there is shown a convenient method for obtaining the 5-oxa 15-alkyl products from corresponding 5-oxa PGF-type compounds shown broadly by formula LXXXVIII. In Chart F, $R_1$, $R_2$, $R_3$, $R_4$, $R_5$, $R_{14}$, $R_{16}$, $Q_2$, and $\sim$ are as defined above. G is alkyl of one to 4 carbon atoms, inclusive, aralkyl of 7 to 12 carbon atoms, inclusive, phenyl, or phenyl substituted with one or 2 fluoro, chloro, or alkyl of one to 4 carbon atoms, inclusive, and $R_{15}$ is $R_1$ as defined above or silyl of the formula-Si-$(G)_3$ wherein G is as defined above. The various G's of a -Si$(G)_3$ moiety are alike or different. For example, a -Si$(G)_3$ can be trimethylsilyl, dimethyl(t-butyl)silyl, dimethylphenylsilyl, or methylphenylbenzylsilyl. Examples of alkyl of one to 4 carbon atoms, inclusive, are methyl, ethyl, propyl, isopropyl, butyl, isobutyl, sec-butyl, and tert-butyl. Examples of aralkyl of 7 to 12 carbon atoms, inclusive, are benzyl, phenethyl, α-phenylethyl, 3-phenylpropyl, α-naphthylmethyl, and 2-(β-naphthyl)ethyl. Examples of phenyl substituted with one or 2 fluoro, chloro, or alkyl of one to 4 carbon atoms, inclusive, are p-chlorophenyl, m-fluorophenyl, o-tolyl, 2,4-dichlorophenyl, p-tert-butylphenyl, 4-chloro-2-methyl-phenyl, and 2,4-dichloro-3-methylphenyl.

This method is well-known for preparing 15-alkyl prostaglandins.

CHART F

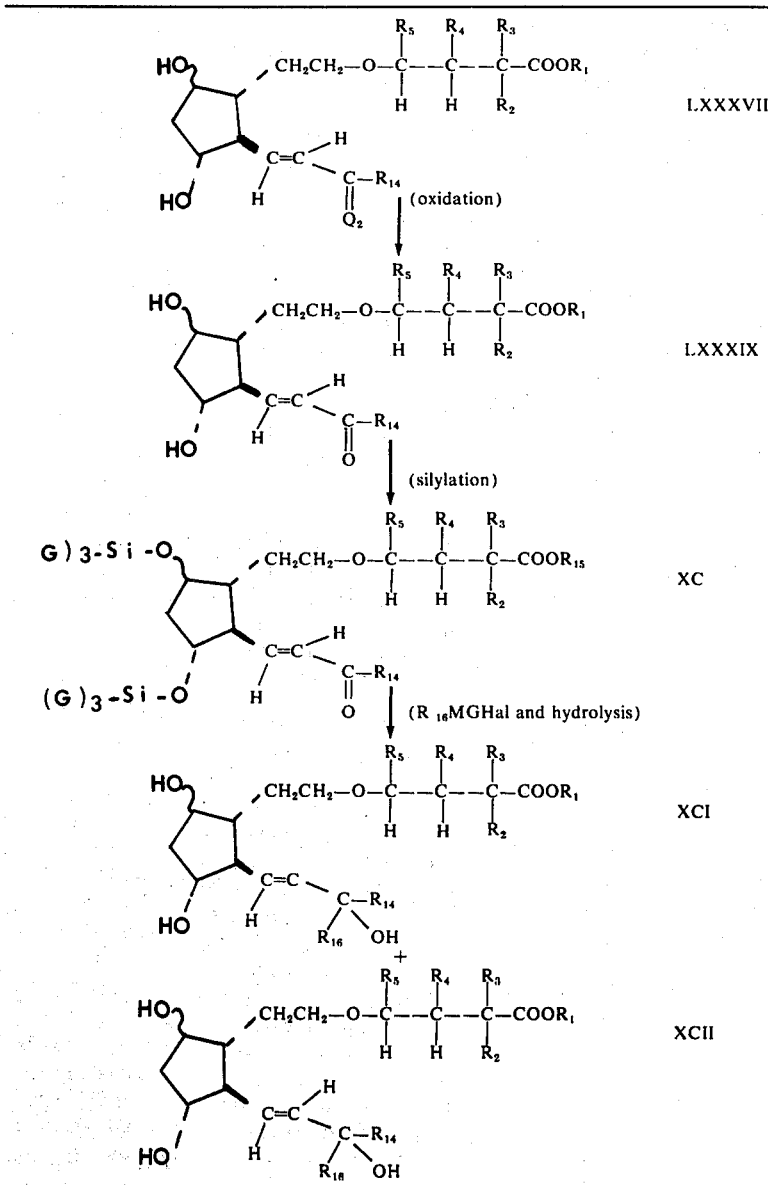

See South African Pat. No. 2482, May 3, 1972, or Belgian Pat. No. 766,682, Derwent No. 72109S.

The acids and esters of formula LXXXVIII, available herein by the processes of Charts B and C, are transformed to the corresponding intermediate 15-oxo acids and esters of formula LXXXIX, respectively, by oxidation with reagents such as 2,3-dichloro-5,6-dicyano-1,4-benzoquinone, activated manganese dioxide, or nickel peroxide (see Fieser et al., "Reagents for Organic Synthesis," John Wiley & Sons, Inc., New York, N.Y., pp. 215, 637 and 731).

Continuing with Chart F, intermediate LXXXIX is transformed to a silyl derivative of formula XC by procedures known in the art. See, for example, Pierce, "Silylation of Organic Compounds," Pierce Chemical Co., Rockford Illinois (1968). Both hydroxy groups of the formula-LXXXIX reactant are thereby transformed to —O—Si—(G)$_3$ moieties wherein G is as defined above, and sufficient of the silylating agent is used for that purpose according to known procedures. When R$_1$ in the formula-LXXXIX intermediate is hydrogen, the —COOH moiety thereby defined is usually transformed to —COO—Si—(G)$_3$, additional silylating agent being used for this purpose. This latter transformation is aided by excess silylating agent and prolonged treatment. When R$_1$ in formula LXXXIX is alkyl, then R$_{15}$ in Formula XC will also be alkyl. The necessary silylating agents for these transformations are known in the art or are prepared by methods known in the art. See, for example, Post, "Silicones and Other Organic Silicon Compounds," Reinhold Publishing Corp., New York, N.Y. (1949).

The intermediate silyl compound of formula XC is transformed to the final compounds of formula XCI + XCII by first reacting the silyl compound with a Grignard reagent of the formula R$_{16}$MgHal wherein R$_{16}$ is methyl or ethyl, and Hal is chloro, bromo, or iodo. For this purpose, it is preferred that Hal be bromo. This reaction is carried out by the usual procedure for Grignard reactions, using diethyl ether as a reaction solvent and saturated aqueous ammonium chloride solution to hydrolyze the Grignard complex. The resulting disilyl or trisilyl tertiary alcohol is then hydrolyzed with water to remove the silyl groups. For this purpose, it is advantageous to use a mixture of water and sufficient of a water-miscible solvent, e.g., ethanol to give a homogenous reaction mixture. The hydrolysis is usually complete in 2 to 6 hours at 25° C., and is preferably carried out in an atmosphere of an inert gas, e.g., nitrogen or argon.

The mixture of 15-S and 15-R isomers obtained by this Grignard reaction and hydrolysis is separated by procedures known in the art for separating mixtures of prostanoic acid derivatives, for example, by chromatography on neutral silica gel. In some instances, the lower alkyl esters, especially the methyl esters of a pair of 15-S and 15-R isomers are more readily separated by silica gel chromatography than are the corresponding acids. In those cases, it is advantageous to esterify the mixture of acids as described below, separate the two esters, and then, if desired, saponify the esters by procedures known in the art for saponification of prostaglandins F.

Referring to Chart G, there is shown a preferred method of obtaining the 5-oxa-15-alkyl-PGF-type compounds as 15-alkyl ethers.

CHART G

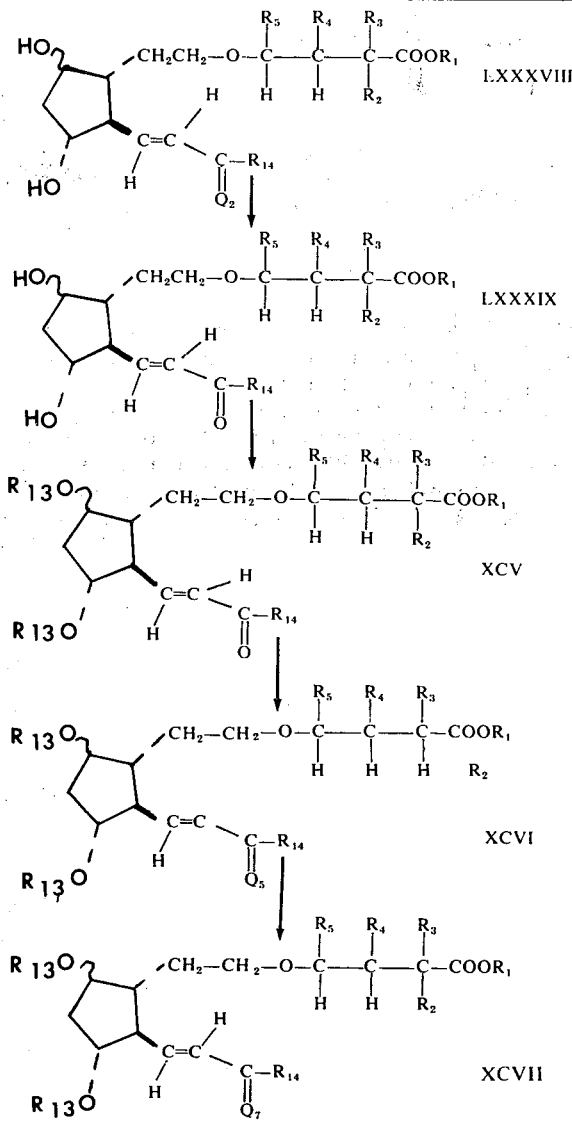

In Chart G, R$_1$, R$_2$, R$_3$, R$_4$, R$_5$, R$_{13}$, R$_{14}$, Q$_2$, Q$_5$, and ~ are as defined above. Q$_7$ is either

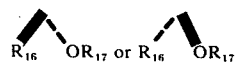

wherein R$_{16}$ and R$_{17}$ are as defined above, i.e. alkyl of one to 4 carbon atoms, inclusive, being the same or different. Starting material LXXXVIII and intermediate LXXXIX are identical with those of Chart F. Compound XCV is obtained by replacing the hydrogen atoms of the C-9 and C-11 hydroxyls with blocking groups R$_{13}$ by the methods discussed above for Chart A. Compound XCVI is then obtained by replacing the C-15 oxo with Q$_5$ by a Grignard reaction, employing R$_{16}$MgHal. Thereafter, compound XCVII is obtained by alkylation of the C-15 hydroxy using the methods and reagents discussed above for Chart D, for example diazoalkanes. Finally, the formula-XCVII compound is readily transformed to the PGF-type products by hydrolysis of the R$_{13}$ blocking groups. The 15-R and 15-S isomers are separated by conventional means, for example silica gel chromatography.

Referring to Chart H, there are shown the transformations from the various 5-oxa PGE-type compounds of formula XCVIII to the corresponding PGF, PGA, and PGB compounds. In Chart H, $R_1$, $R_2$, $R_3$, $R_4$, $R_5$, $R_{14}$, $Q_1$, and $\sim$ are as defined above.

The various 5-oxa PGF-type compounds of formula CI are obtained by carbonyl reduction of the PGE-type compounds using the methods and reagents discussed above for Chart C.

The various 5-oxa PGA-type compounds of formula XCIX are obtained by acidic dehydration of the PGE-type compounds. For example, acidic dehydration of 5-oxa-PGE$_1$ gives 5-oxa-PGA$_1$.

CHART H

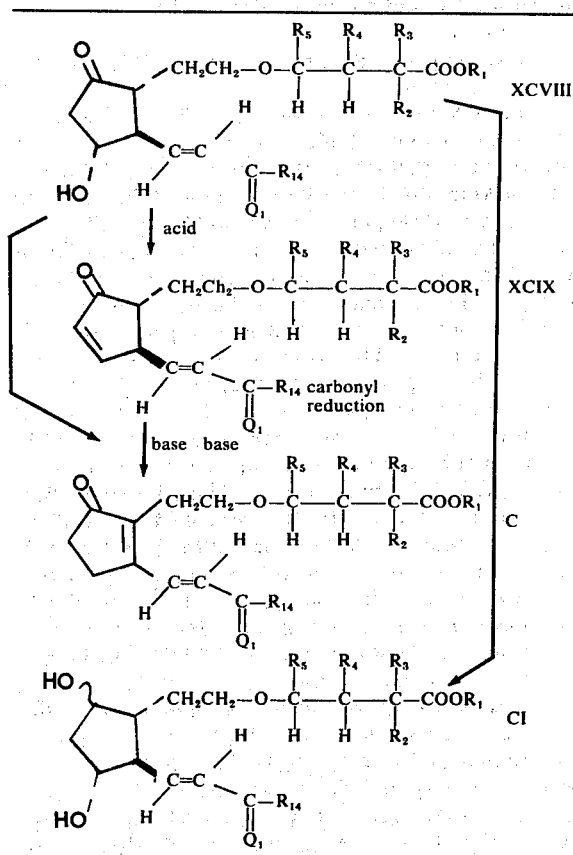

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162-163 (1967); and British Specification No. 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various 5-oxa PGB-type compounds encompassed by formula C are prepared by basic dehydration of the PGE-type compounds or by contacting the PGA compounds of formula XCIX with base. For example, both 5-oxa PGE$_1$ and 5-oxa PGA$_1$ give 5-oxa PGB$_1$ on treatment with base. These basic dehydrations and double bond migrations are carried out by methods known in the art for similar reactions of known prostanoic acid derivatives. See, for example, Bergstrom et al., J. Biol. Chem. 238,3555 (1963). The base is any whose aqueous solution has pH greater than 10. Preferred bases are the alkali metal hydroxides. A mixture of water and sufficient of a water-miscible alkanol to give a homogenous reaction mixture is suitable as a reaction medium. The PGE-type or PGA-type compound is maintainted in such a reaction medium until no further PGB-type compound is formed, as shown by the characteristic ultraviolet light absorption near 278 nm for the PGB type compound.

Referring to Charts I and J, there is shown a general method for preparing 5-oxa 11-deoxy PGF analogs. In Charts I and J, $R_2$, $R_3$, $R_4$, $R_5$, $R_8$, $R_9$, $R_{11}$, $R_{14}$, $Q_2$, $Q_3$, and $\sim$ have the same meaning ascribed to them above for Charts A and B.

Referring to Chart I, there are shown the steps by which the formula-CII aldehyde is transformed to lactol CVI. Thereafter, product CX is obtained by the steps of Chart J. Starting material CII of Chart J is known in the art in racemic form. See Corey et al., Tetrahedron Lett. No. 49,4753 (1971) and Crabbe' et al., ibid No. 2,115 (1972). When a formula-CIII compound is prepared by reacting a racemic compound corresponding to formula CII with a racemic Wittig reagent, there are obtained two pairs of racemates which are separable into pairs of racemic compounds by methods known in the art, e.g. silica gel chromatography. When a racemic compound corresponding to formula CII is reacted with an optically active isomer of the Wittig reagent, there are obtained two diastereomers corresponding to the formula-CIII compound which are separated by conventional methods, e.g. by silica gel chromatography.

It is preferred that the formula-CII compound be used in the optically active form which will lead to an 11-deoxy prostaglandin analog of the natural configuration. For this purpose, a process is used for resolving a racemic mixture of an oxo compound of the formula

CHART I

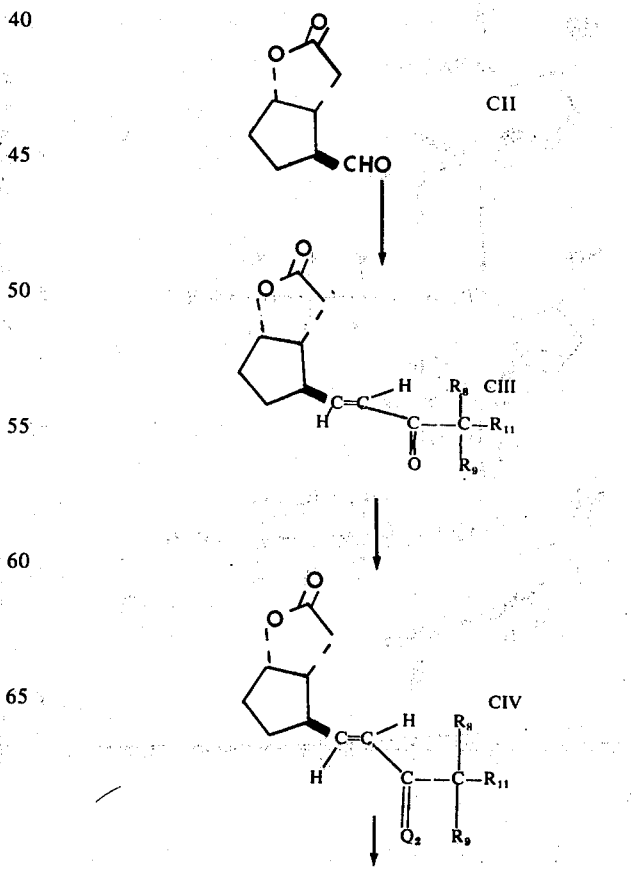

CHART I-continued

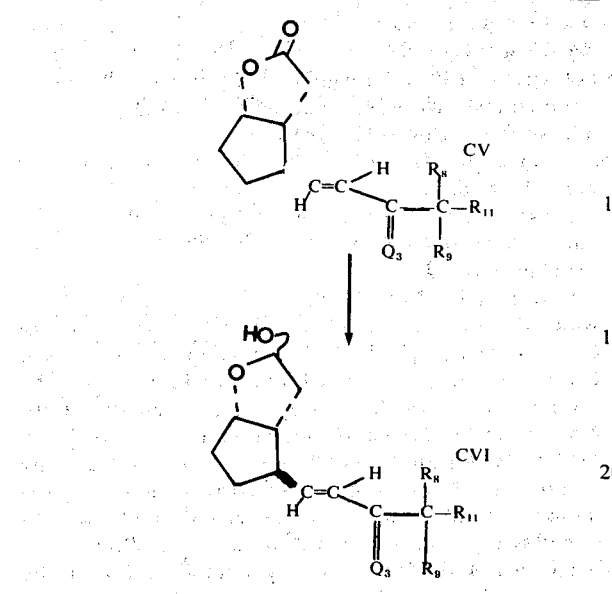

CHART J

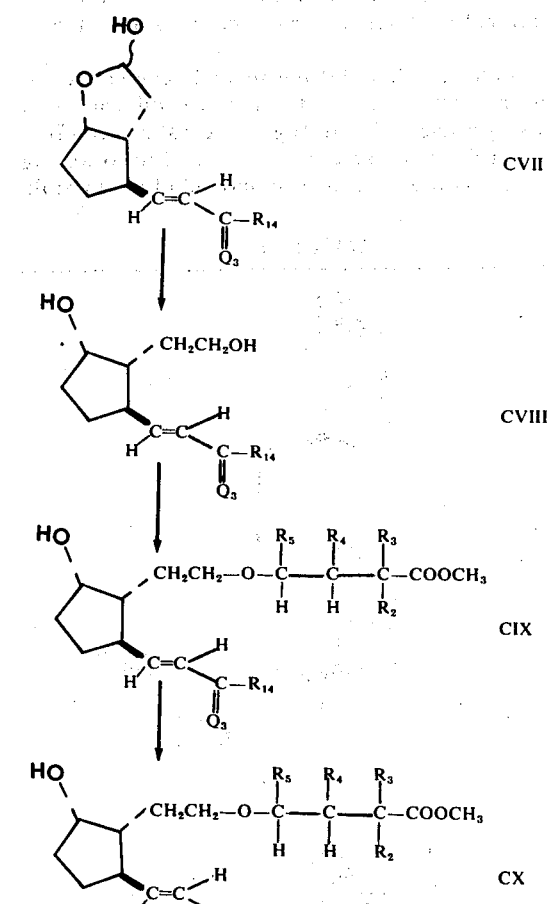

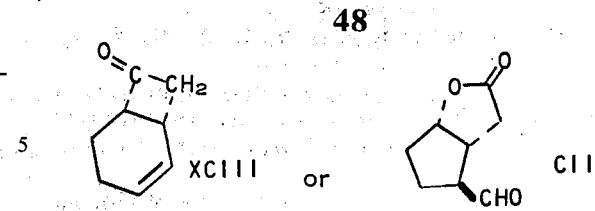

and of the mirror image thereof, which comprises the steps of a. converting the oxo compound by reaction with an optically active ephedrine to a mixture of oxazolidine diastereomers, b. separating at least one oxazolidine diastereomer from said mixture, c. hydrolyzing said oxazolidine to free the optically active oxo compound, and d. recovering said optically active oxo compound.

In carrying out the resolution of the formula-XCIII ketone, there is prepared an oxazolidine by reaction of the ketone with an optically active ephedrine, e.g. d- or l-ephedrine, or d- or l-pseudoephedrine. Approximately equimolar quantities of the reactants are employed in a solvent such as benzene, isopropyl ether, or dichloromethane. The reaction proceeds smoothly over a wide range in temperature, for example 10° to 80° C., although for some reactants the range 20° to 30° C. is preferred for convenience. The reaction occurs quickly, within minutes, whereupon the solvent is removed, preferably under vacuum. The product consists of the diastereomers of the ketone-ephedrine product, i.e. the oxazolidines. At least one of the diastereomers is separated by methods known in the art, including crystallization and chromatography. In this instance, crystallization is used as the preferred method. Repeated recrystallization of the thus-obtained solid oxazolidine from a suitable solvent, e.g., isopropyl ether, yields one of the diastereomers in substantially pure form. The oxazolidine is then hydrolyzed by procedures known in the art to release the ketone.

The mother liquor from the recrystallized diastereomer contains the optical isomer having opposite configuration. A preferred method for isolating this second diastereomer, however, is to prepare the oxazolidine of the racemic ketone using ephedrine of the opposite configuration to that first employed above, and thereafter recrystallizing as above. Finally, hydrolysis and recovery yield the resolved formula-XCIII ketone in opposite configuration to that first obtained above.

Each optically active ketone can be converted to an aldehyde of the formula

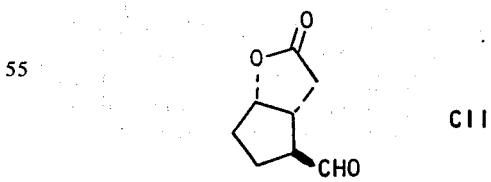

or the mirror image thereof, using the procedures of Corey et al., Tetrahedron Lett. No. 49, 4753 (1971).

Likewise, the above process of resolution applied to the racemate containing the formula-CII aldehyde yields the optically active formula-CII aldehyde which produces the 11-deoxy prostaglandin analogs having the natural configuration.

Referring to Chart I, the formula-CIII compound is obtained by Wittig alkylation of CII, using the sodio derivative of the appropriate 2-oxoalkylphosphonate. The trans enone lactone is obtained stereospecifically. See D.H. Wadsworth et al., J. Org. Chem. 30, 680 (1965). For the Wittig reaction certain phosphonates are employed having the general formula

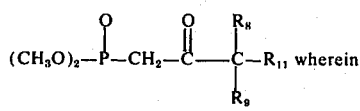 wherein $R_8$, $R_9$, and $R_{11}$ are as defined above. The phosphonates are prepared and used by methods known in the art. See Wadsworth et al., Corey et al., and Crabbe' et al., references cited above. For this purpose as well as for the process of Chart A above, the phosphonates are conveniently obtained by condensing the appropriate aliphatic acid ester with dimethyl methylphosphonate in the presence of n-butyllithium. For this purpose, acids of the general formula $R_{11}$—$C(R_8R_9)$—COOH are used in the form of their lower alkyl esters, preferably methyl or ethyl. For example methyl esters are formed from the acids by reaction with diazomethane. These aliphatic acids of various chain length, with or without branching within the scope of $R_{11}$ as defined above are known in the art or can be prepared by methods known in the art.

Aliphatic acids without branching are propionic, butyric, valeric, heptanoic, octanoic, nonanoic, decanoic, or undecanoic acids.

In the case of acids with branching, many are readily available, e.g. 2-methylpropionic, 2-methylbutyric, 2-ethylbutyric, 3-methylbutyric, 2,2-dimethylbutyric, 2-ethyl-2-methylbutyric, 2,2-diethylbutyric, 2,3-dimethylbutyric, 3,3-dimethylbutyric, 2-methyvaleric, 2-propylvaleric, 3-methylvaleric, 2,2-dimethylvaleric, 3,3-diethylvaleric, 2-methyl-2-propylvaleric, 2-ethyl-3-methylvaleric, 2-methylhexanoic, 2-ethylhexanoic, 2-butylhexanoic, 2,2-dimethylhexanoic, 2,3-dimethylhexanoic, 2-butyl-2-methylhexanoic, 2-methylheptanoic, 2-propylheptanoic, 2-butylheptanoic, 2,2-diethylheptanoic, 2-methyl-2-propylheptanoic, 2-ethyloctanoic, 2-propyloctanoic, 3-methyloctanoic, 2-ethyl-2-methyloctanoic, 2-ethylnonanoic, 2,2-dimethylnonanoic, and 2-methyldecanoic acid. Other acids are available by methods known in the art, for example reaction of a branched alkyl halide with sodium cyanide to form a nitrile and subsequent hydrolysis to the acid.

Continuing with Chart I, the formula-CIV compound is obtained as a mixture of alpha and beta isomers by reduction of CIII. For this reduction, use is made of any of the known ketonic carbonyl reducing agents which do not reduce ester or acid groups or carbon-carbon double bonds when the latter is undesirable. Examples of those are the metal borohydrides, especially sodium potassium, and zinc borohydrides, lithium (tri-tert-butoxy)aluminum hydride, metal trialkoxy borohydrides, e.g., sodium trimethoxyborohydride, lithium borohydride, and when carbon-carbon double bond reduction is not a problem, the boranes, e.g., disiamylborane.

For production of natural-configuration PG-type compounds, the desired alpha (S) form of the formula-CIV compound is separated from the beta isomer by silica gel chromatography.

The formula-CV intermediate, wherein the hydrogen atoms of the hydroxyls are replaced with a blocking group $R_{13}$, is prepared by methods known in the art, for example using the conditions set forth above for dihydropyran, dihydrofuran, or substituted vinyl ethers. Especially preferred for $R_{13}$ are tetrahydropyranyl or ($\alpha$-ethoxy)ethyl.

The lactol CVI is obtained on reduction of the formula-CV lactone, using, for example, diisobutylaluminum hydride. The reduction is preferably done at $-60°$ to $70°$ C.

Referring to Chart J, there are shown the steps by which lactol CVII is transformed to 5-oxa 11-deoxy PGF-type products. Lactol CVII includes lactol CVI of Chart I within its scope, and also lactols of the formula

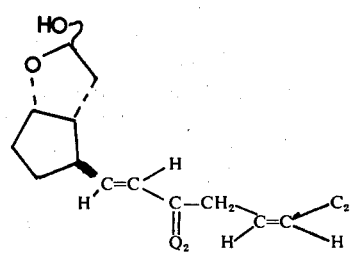

The lactol of formula XCIV is obtained from aldehyde CII by a Wittig reaction employing a phosphonium salt, for example $(C_6H_5)_3P^+CH_2CH(OH)CH_2CH=CHC_2H_5$ $I^-$. See Corey et al., J. Am. Chem. Soc. 93, 1490 (1971).

The steps of Chart J by which lactol CVII is transformed to alcohol CVIII and thence to ether CIX and finally product CX utilize substantially the same reactions as those described above for the steps of Chart B. At each stage the products are isolated by methods known in the art, for example silica gel chromatography.

Optically active compounds are obtained from optically active intermediates according to the process steps of Charts A, B, C, D, E, F, G, H, I, and J. When racemic intermediates are used in reactions corresponding to the processes of Charts A-J, inclusive, and racemic products are obtained, these racemic products may be used in their racemic form or, if preferred, they may be resolved as optically active isomers by procedures known in the art.

For example, when final compound XXI to LXII is a free acid, the dl (racemic) form thereof is resolved into the d and l forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula XXI to LXII is then obtained by treatment of the salt with an acid by known general procedures.

Another procedure for obtaining optically active 5-oxa PGF-type compounds is by stereoselective microbiological reduction of the racemic 5-oxa PGE-type compounds. For this purpose actively fermenting baker's yeast is employed. The PGE-type compound is contacted with a yeast-sugar-water mixture at about 25° C. for 24-48 hours. There is produced by reduction a mixture of the PGF$\alpha$ compound and the enantiomeric PGF$\beta$ compound, which are separable by silica gel chromatography for example. Accompanying this transformation, carboxylic ester groups are removed by hydrolysis. Accordingly, from dl-5-oxa PGE$_1$ methyl ester, there are obtained natural configuration 5-oxa-PGF$_{1\alpha}$ and enantiomeric 5-oxa-PGF$_{1\beta}$.

When the processes of Charts A-J yield an ester, such as where R$_1$ is methyl, the free acid products are obtained by methods known in the art. For example, the 5-oxa PGF$_2$ analogs are subjected to saponification in an aqueous alkaline medium to form an alkaline salt, which is then acidified to yield the free acid. A preferred method for the 5-oxa PGE$_2$ analogs, and useful for the 5-oxa PGF$_2$ analogs as well, is by enzymatic hydrolysis using an esterase enzyme composition obtained from the marine invertebrate Plexaura homomalla (Esper), 1792. Plexaura homomalla is a member of the subclass Octocorallia, order Gorgonacea, suborder Holaxonia, family Plexauridae, genus Plexaura. See, for example, Bayer, "The Shallow-Water Octocorallia of the West Indian Region", Martinus Nijhoff, The Hague (1961). Colonies of these Plexaura homomalla are abundant on the ocean reefs in the zone from the low-tide line to about 25 fathoms in the tropical and subtropical regions of the western part of the Atlantic Ocean, from Bermuda to the reefs of Brazil, including the eastern shore reefs of Florida, the Caribbean island and mainland reefs, and the Gulf of Mexico island and mainland reefs. These colonies are bush-like or small tree-like in habit and are readily identified for collection as Plexaura homomalla (Esper), 1792, by those of ordinary skill in this art. Two forms exist, the R-form and the S-form See W. P. Schneider et al., J. Am. Chem. Soc. 94, 2122 (1972).

The esterase enzyme composition is produced by the steps: (1) extracting colonies or colony pieces of the marine invertebrate Plexaura homomalla (Esper), 1792, forma R or forma S, with liquid acetone for a sufficient time to remove substantially all soluble lipids, and (2) recovering the acetone-insoluble matter as said composition.

The colonies of Plexaura homomalla are used either in their as-harvested form or in broken or chopped pieces. It is immaterial whether they are used fresh from their natural environment, or after freezing and thawing, or even after drying under ambient conditions.

The extraction with acetone may be done batch-wise, as by stirring in a container, or by percolation, or by continuous methods of extraction known in the art. If stirring is used, it is advantageous to first chop the Plexaura homomalla into small pieces, for example less than 3 mm. in greatest dimension. The product is accordingly then a powder consisting of pieces smaller than 3 mm. Contact with acetone is continued until substantially all of the soluble lipids are removed. Normally one hour is sufficient, although a longer time is required for whole colonies and a shorter time is sufficient for chopped colonies with efficient extraction. The end-point can be determined simply by examination of the acetone, as by evaporation and by physical measurements on any residue thus obtained. The extraction temperature is kept below 50° C. to avoid denaturation of the enzyme, and is preferably in the range 20° to 30° C. Lower temperatures may be used but the extraction then proceeds more slowly. The extraction is generally done at atmospheric pressure, but it may be carried out at higher or lower pressures provided the acetone is in a liquid state when contacting the Plexaura homomalla.

The acetone-insoluble enzyme composition is recovered from the acetone by decantation, filtration, centrifugation, or other convenient method for separating solids and liquids. A small amount of adherent acetone, for example, 10% of the weight of the composition, may be left on the product but it is preferred that the amount be lowered to less than 1%, for example by drying under ambient conditions or under reduced pressure. The product can then be stored without deterioration, preferably at about −20° C.

In utilizing the above esterase enzyme composition for the purposes of this invention, the 5-oxa prostaglandin ester is contacted with a mixture of the enzyme composition and water. The ester is conveniently added as a solution, for example in ethanol or benzene, to about 50-100 times its weight of water. The enzyme composition is added in an amount about 1-15 times the weight of ester. The mixture is stirred until the ester is hydrolyzed, generally about 18-24 hours at 25° C. Temperatures of about 0°-50° C. may be employed, although about 25° C. is preferred. The progress of hydrolysis is readily followed by analysis, for example by thin-layer chromatography by methods known in the art. See, for example, Hamberg et al., J. Biol. Chem. 241, 257 (1966). Finally, several volumes of acetone are added and the soluble acid products are recovered by filtration, concentration, and extraction using methods known in the art.

As discussed above, the processes of Charts A-J, inclusive, lead variously to acids (R$_1$ is hydrogen) or to esters (R$_1$ is alkyl, cycloalkyl, aralkyl, phenyl or substituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389-394 (1954).

An alternative method for esterification of the carboxyl moiety of the acid compounds comprises transformation of the free acid to the corresponding silver salt, followed by interaction of that salt with alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final formula XXI-to-LXII compounds prepared by the processes of this invention, in free acid form, are transformed to pharmacologically acceptable salts by neutralization with appropriate amounts of the corresponding iorganic or organic base, examples of which correspond to the cations and amines listed above. These transformations are carried out by a variety of procedures known in the art to be generally useful for the preparation of inorganic, i.e., metal or ammonium salts, amine acid addition salts, and quaternary ammonium salts. The choice of procedure depends in part upon the solubility characteristics of the particular salt to be prepared. In the case of the inorganic salts, it is usually suitable to dissolve the formula XXI-to LXII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula XXI-to-LXII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula XXI-to-LXII acid with the stoichiometric amount of the corresponding quaternary ammonium hydroxide in water solution, followed by evaporation of the water.

The final formula XXI-to-LXII acids or esters prepared by the processes of this invention are transformed to lower alkanoates by interaction of the formula XXI-to-LXII hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction oil diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography or crystallization.

By this procedure, the formula XXI-XXIII, XXXIX, XL, XLIII, and XLIV 5-oxa PGE-type compounds are transformed to dialkanoates; the formula XXIV-XXVI, XLI, XLII, XLV, and XLVI 5-oxa 11-deoxy PGE-type compounds are transformed to monoalkanoates; the formula XXVII-XXIX, XLVII, XLVIII, LI, and LII 5-oxa PGF-type compounds are transformed to trialkanoates; the formula XXX-XXXII, XLIX, L, LIII, and LIV 5-oxa 11-deoxy PGF-type compounds are transformed to dialkanoates; the formula XXXIII-XXXV and LV-LVIII 5-oxa PGA-type compounds and the formula XXXVI-XXXVIII and LIX-LXII 5-oxa PGB-type compounds are transformed to monoalkanoates.

When a PGE-type mono- or dialkanoate is transformed to a PGF-type compound by carbonyl reduction as shown in Chart H, a corresponding PGF-type mono- or dialkanoate is formed. The product is used as such or is transformed to a di- or trialkanoate by the above-described procedure. The additional alkanoyloxy group can be the same or different than the alkanoyloxy group or groups present before the carbonyl reduction.

DESCRIPTION OF THE PREFERRED EMBODIMENTS

The invention can be more fully understood by the following examples and preparations:

All temperatures are in degrees centigrade.

Infrared absorption spectra are recorded on a Perkin-Elmer Model 421 infrared spectrophotometer. Except when specified otherwise, undiluted (neat) samples are used.

Ultraviolet spectra are recorded on a Cary Model 15 spectrophotometer.

NMR spectra are recorded on a Varian A-60 spectrophotometer on deuterochloroform solutions with tetramethylsilane as an internal standard (downfield).

Mass spectra are recorded on an Atlas CH-4 mass spectrometer with a TO-4 source (ionization voltage 70 ev).

The collection of chromatographic eluate fractions starts when the eluant front reaches the bottom of the column.

"Brine", herein, refers to an aqueous saturated sodium chloride solution.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 257 (1966).

"Skellysolve-B" refers to mixed isomeric hexanes.

Silica gel chromatography, as used herein, is understood to include elution, collection of fractions, and combination of those fractions shown by TLC (thin layer chromatography) to contain the desired product free of starting material and impurities.

| Preparation 1 | Trimethyl Ortho-4-bromobutyrate, $Br-CH_2CH_2CH_2-C-(OCH_3)_3$. |
|---|---|

Refer to S. M. McElvain et al., J. Am. Chem. Soc. 64, 1825 (1942). A mixture of 4-bromobutyronitrile (74 g.), 21 ml. of methanol, and 250 ml. of diethyl ether is treated at 0° C., while stirring, with hydrogen bromide (40 g.) over a 30-min. period. The mixture is stirred for an additional 4 hr. at 0° C. and then 100 ml. of hexane is added. The precipitated imino ester hydrobromide is separated from the liquid by filtration and washed with 400 ml. of diethyl ether-hexane (1:1). The imino ester salt is treated in 250 ml. diethyl ether with 150 ml. of methanol and 25 ml. of methyl orthoformate, while stirring at about 25° C. for 24 hr. The mixture is cooled to about −10° C. and the organic solution separated from the formed ammonium bromide, together with 100 ml. of diethyl ether rinse. The solution is immediately and quickly washed with an ice-cold solution prepared from potassium carbonate (20 g.) and 300 ml. of brine. The organic phase is washed with brine, treated with 3 drops of pyridine, and dried over anhydrous magnesium sulfate. The solution is concentrated under reduced pressure, diluted with 150 ml. of benzene, and again concentrated. The residue is distilled to yield the title compound 66.0 g., b.p. 60°–62° C./0.5 mm., having NMR peaks at 3.35–3.64, 3.22, 2.05–2.6, and 1.82–1.97 δ.

Following the procedure of Preparation 1, there are prepared other substituted ortho-4-bromobutyrates within the scope of

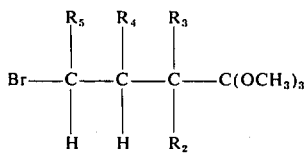

wherein $R_2$, $R_3$, $R_4$, and $R_5$ are as defined above, namely $R_3$ is hydrogen, alkyl of one to 4 carbon atoms, inclusive, or fluoro; $R_2$ is hydrogen or fluoro, with the proviso that $R_2$ is fluoro only when $R_3$ is hydrogen or fluoro; and $R_4$ and $R_5$ are hydrogen or alkyl of one to 4 carbon atoms, inclusive, being the same or different, with the proviso that no more than one of $R_3$, $R_4$, and $R_5$ is alkyl. The appropriate halonitrile is converted to the corresponding imino ester hydrohalide and thence to the ortho ester. Chloronitriles are readily converted to bromonitriles by methods known in the art, for example contacting with lithium bromide in acetone.

In this way there are obtained the following substituted ortho-4-bromo-butyrates:

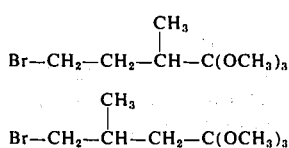

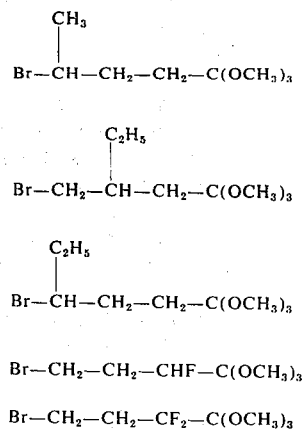

| Preparation 2 | 3α-Benzoyloxy-2β-carboxaldehyde-5α-hydroxy-1α-cyclopentaneacetic Acid γ-Lactone (Formula LXVII: $R_{12}$ is benzoyl). |
|---|---|

Refer to Chart A. a. To a mixture of formula-LXIII laevorotatory (−) 3α-hydroxy-5α-hydroxy-4-iodo-2β-methoxymethyl-1α-cyclopentaneacetic acid γ-lactone (E. J. Corey et al., J. Am. Chem. Soc. 92, 297 (1970), 75 g.) in 135 ml. of dry pyridine under a nitrogen atmosphere is added 30.4 ml. of benzoyl chloride with cooling to maintain the temperature at about 20°–40° C. Stirring is continued for an additional 30 min. About 250 ml. of toluene is added and the mixture concentrated under reduced pressure. The residue is dissolved in one liter of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the corresponding formula-LXIV 3α-benzoyloxy compound, m.p. 84°–86° C.; $[\alpha]_D$ +7° ($CHCl_3$); infrared spectral absorptions at 1768, 1722, 1600, 1570, 1490, 1275, 1265, 1180, 1125, 1090, 1060, 1030, and 710 $cm^{-1}$; and NMR (nuclear magnetic resonance) peaks at 2.1–3.45, 3.3, 3.58, 4.38, 5.12, 5.51, 7.18–7.58, and 7.83–8.05 δ.

b. The iodo group is removed as follows. To a solution of the above benzoyloxy compound (60 g.) in 240 ml. of dry benzene is added 2,2'-azobis-(2-methylpropionitrile) (approximately 60 mg.). The mixture is cooled to 15° C. and to it is added to a solution of 75 g. tributyltin hydride in 600 ml. of ether, with stirring, at such a rate as to maintain continuous reaction at about 25° C. When the reaction is complete as shown by TLC (thin layer chromatography) the mixture is concentrated under reduced pressure to an oil. The oil is mixed with 600 ml. of Skellysolve B (mixed isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced presssure to an oil, 39 g. of the formula-LXV iodine-free compound. An analytical sample gives $[\alpha]_D$ −99° (CHCl$_3$); infrared spectral absorptions at 1775, 1715, 1600, 1585, 1490, 1315, 1275, 1180, 1110, 1070, 1055, 1015, and 715 cm$^{-1}$; NMR peaks at 2.5–3.0, 3.25, 3.34, 4.84–5.17, 5.17–5.4, 7.1–7.5, and 7.8–8.05 δ; and mass spectral peaks at 290, 168, 105, and 77.

c. The 2β-methoxymethyl compound is changed to the formula-LXVI hydroxymethyl compound as follows. To a cold (0.5° C.) solution of the above iodine-free methoxymethyl lactone (20 g.) in 320 ml. of dichloromethane under nitrogen is added a solution of 24.8 ml. of boron tribromide in 320 ml. of dichloromethane, dropwise with vigorous stirring over a period of 50 min. at 0°–5° C. Stirring and cooling are continued for 1 hr. When the reaction is complete, as shown by TLC, there is cautiously added a solution of sodium carbonate (78 g.) monohydrate in 200 ml. of water. The mixture is stirred at 0°–5° C. for 10–15 min., saturated with sodium chloride, and the dichloromethane layer separated. Additional dichloromethane extractions of the water layer are combined with the main dichloromethane solution. The combined solutions are rinsed with brine, dried over sodium sulfate and concentrated under reduced pressure to an oil, 18.1 g. of the formula-LXVI 2β-hydroxymethyl compound. An analytical sample has m.p. 116°–118° C.; $[\alpha]_D$ −80° (CHCl$_3$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 δ.

d. The title 2β-carboxaldehyde compound is prepared as follows. To a mixture of 250 ml. of dichloromethane and Collins' reagent prepared from chromium trioxide (10.5 g.) and 16.5 ml. of pyridine, cooled to 0° C., a cold solution of the hydroxymethyl compound of step c (5.0 g.) in 50 ml. of dichloromethane is added, with stirring. After 7 min. of additional stirring, the formula-LXVII title intermediate is obtained and is used directly without isolation (see Preparation 3).

Following the procedures of Preparation 2, but replacing that optically active formula-LXIII iodolactone with the racemic compound of that formula and the mirror image thereof (see E. J. Corey et al., J. Am. Chem. Soc. 91, 5675 (1969)) there is obtained the racemic compound corresponding to formula LXVII.

| Preparation 3 | 2β-[(3S)-3[(Tetrahydropyran-2-yl)oxy]-trans-1-octenyl]-5α-hydroxy-3α-[(tetrahydropyran-2-yl)oxy]-1α-cyclopentane-acetaldehyde, γ-Lactol (Formula LXXII: Q$_3$ is H OTHP, R$_8$ and R$_9$ are hydrogen, R$_{11}$ is n-butyl, and R$_{13}$ is THP). |
|---|---|

Refer to Chart A. a. Compound LXVIII is prepared as follows. There is first prepared a solution of the anion of dimethyl 2-oxoheptyl phosphonate (E. J. Corey et al., J. Am. Chem. Soc. 90, 3247 (1968)). The phosphonate (8.0 g.) is added in portions over a 2–3 min. period to a stirred mixture of sodium hydride (1.75 g. of 50%) in 250 ml. of dry tetrahydrofuran under nitrogen previously cooled to 5° C. Stirring is continued at about 25° C. for at least 1 hr. and the mixture is cooled to 0° C. There is then added a benzene solution of the formula-LXVII aldehyde and stirring is continued for 1.5 hr. at about 25° C. Then about 3 ml. of acetic acid is added dropwise and the mixture is concentrated under reduced pressure. The residue is taken up in 400 ml. of ethyl acetate, washed with water and brine, dried over sodium sulfate, and concentrated under reduced pressure. The residue is dissolved in 50 ml. of dichloromethane and chromatographed on silica gel (500 g.) by elution gradient with 25–30% ethyl acetate in Skellysolve B. Those fractions shown by TLC (R$_f$=0.58 in the A-IX system) to be free of starting material (R$_f$=0.31) are combined and concentrated to an oil of the formula-LXVIII compound, 4.0 g. The oil yields crystals, m.p. 63–65 C., $[\alpha]_D$ = −84° (CHCl$_3$); infrared spectral absorptions at 1775, 1720, 1670, 1630, 1600, 1585, 1490, 1315, 1275, 1175, 1115, 1070, 1050, 1025, 980, and 715 cm$^{-1}$., NMR peaks at 0.7–1.9, 2.2–3.1, 4.9–5.45, 6.17, 6.71, 7.2–7.6, and 7.8–8.1 δ; and mass spectral peaks at 370, 314, 248, 192, and 177.

b. To a mixture of zinc borohydride prepared from zinc chloride (anhydrous, 19 g.) and sodium borohydride (4.3 g.) in 120 ml. of dry 1,2-dimethoxyethane under nitrogen stirred for 20 hr. and then cooled to −20° C., is added the formula-LXVIII ketone above (10.5 g.) in 55 ml. of 1,2-dimethoxyethane. The mixture is stirred at −20° C. for 17 hr., warmed to room temperature and stirred until reaction is complete as shown by TLC. The mixture is cooled to 0°–5° C., and 30 ml. of water added dropwise. After hydrolysis is complete, the mixture is shaken with 200 ml. of ethyl acetate and separated. The ethyl acetate layer is washed with brine, dried over sodium sulfate, and concentrated under reduced pressure to 11.6 g. product. The α and β isomers are separated by chromatography on a silica gel column by gradient elution with 35–60% ethyl acetate in Skellysolve B. Fractions containing the α or β isomers, as shown by TLC, are combined and concentrated to yield, respectively, 5.1 g. of formula-LXIX product where Q$_2$ is

and 4.15 g. of formula-LXIX product where Q$_2$ is

The LXIX-α product has m.p. 71°–72° C., $[\alpha]_D$ −68° (CHCl$_3$); infrared spectral absorption at 3480, 1720, 1600, 1585, 1490, 1315, 1275, 1175, 1115, 1070, 1050, 1025, 970, and 715; NMR peaks at 0.6–1.6, 1.9–3.0, 3.85–4.17, 4.85–5.35, 5.45–5.68, 7.2–7.55, and 7.8–8.05 δ; and mass spectral peaks at 301, 250, 179, and 105. The LXIX-α product has m.p. 77°–78° C., $[\alpha]_D$ −86° (CHCl$_3$); and infrared and NMR spectra essentially identical with the LXIX-α product.

c. To a solution of the formula-LXIX benzoyloxy α-hydroxyoctenyl compound above (18 g.) in 210 ml. of methanol under nitrogen is added potassium carbonate (6.75 g.) and the mixture is stirred vigorously for 1 hr. About 210 ml. of chloroform is added and the mixture is filtered. The filtrate is concentrated under reduced pressure to a volume of about 50 ml., then made up to a volume of about 230 ml. with chloroform, washed with brine, dried over sodium sulfate, filtered and concentrated under reduced pressure to an oil 10.7 g. The oil is triturated with Skellysolve B, then concentrated to the formula-LXX compound wherein $Q_2$ is

An analytical sample has $[\alpha]_D$ −7° ($CHCl_3$); infrared spectral absorption at 3390, 1760, 1175, 1085, 1035, 970, and 905 $cm^{-1}$; and NMR peaks at 0.9, 1.0–1.7, 1.8–2.9, 3.8–4.2, 4.7–5.0, and 5.4–5.6 δ.

d. There is next prepared the formula-LXXI bis(tetrahydropyranyl ether). The formula-LXX compound above (10.0 g.) is treated with 20 ml. of dihydropyran in 120 ml. of dichloromethane in the presence of pyridine hydrochloride (0.12 g.). After about 2.5 hr. the mixture is filtered, washed with dilute aqueous potassium bicarbonate, dried and concentrated to give the formula-LXXI compound wherein $Q_3$ is

(see Corey et al., op. cit.).

e. To a solution of above lactone LXXI in 250 ml. of toluene at −78° C. is added dropwise, while stirring, diisobutylaluminum hydride (12.5 ml. in 60 ml. of toluene). Stirring is continued at −78° C. for 1 hr., whereupon a solution of 3 ml. of tetrahydrofuran and 1 ml. of water is added cautiously. After the mixture is stirred an additional 0.5 hr. at about 25° C., it is diluted with benzene and filtered. The filtrate is washed with brine, dried, and concentrated to the formula-LXXII title compound (18 g.). See Corey et al., op. cit.

Following the procedures of steps c, d, and e above, but employing the formula-LXIX benzoyloxy β-hydroxyoctenyl compound from step b, there are obtained the corresponding formula-LXX, LXXI, and LXII compounds wherein $Q_2$ is

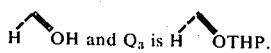

Likewise following the procedures of Preparation 3, but replacing the dimethyl 2-oxoheptylphosphonate of that preparation with the various phosphonates within the scope of

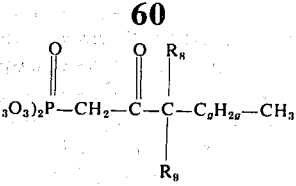

wherein $C_gH_{2g}$ is alkylene of one to 9 carbon atoms, inclusive, with one to 5 carbon atoms, inclusive, in the chain between —$CR_8R_9$— and terminal methyl, and wherein $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro, there are obtained the corresponding formula-LXXII optically active γ-lactols and their racemic compounds wherein $Q_3$ is either

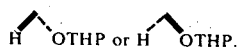

Those phosphonates are prepared by methods described herein or known in the art, utilizing for example the following aliphatic acid esters within the scope of

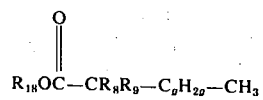

wherein $C_gH_{2g}$, $R_8$, and $R_9$ are as defined above, $R_{18}$ is methyl or ethyl:

methyl butyrate
ethyl 2-methylbutyrate
methyl valerate
methyl 2-ethylvalerate
ethyl 3-methylhexanoate
methyl 2,3-diethylhexanoate
ethyl 4-ethylhexanoate
methyl heptanoate
methyl 3-methylheptanoate
methyl 6-methylheptanoate
ethyl octanoate
methyl nonanoate
methyl 3-propylnonanoate
methyl 2-fluorobutyrate
ethyl 2,2-difluorobutyrate
methyl 2-fluoro-3-methylbutyrate
ethyl 2-fluorovalerate
methyl 2,2-difluorohexanoate
methyl 2-fluoro-3-methylhexanoate
ethyl 4-ethyl-2-fluorohexanoate
methyl 2-fluoroheptanoate
methyl 2-fluoro-6-methylheptanoate
methyl 2,2-difluoro-3-methylheptanoate
ethyl 2-fluorooctanoate
methyl 2,2-difluorononanoate and
methyl 2-fluoro-3-propylnonanoate.

For example, methyl heptanoate yields dimethyl 2-oxooctylphosphonate and, thence, the formula-LXXII[2β- 3(S) or (R)-3-[(tetrahydropyran-2-yl)oxy]-trans-1-nonenyl]-5α-hydroxy-3α-[(tetrahydropyran-2-yl)oxy]-1α-cyclopentaneacetaldehyde, γ-lactol. Likewise, methyl 2,2-difluorohexanoate yields dimethyl 2-oxo-3,3-difluoro-heptylphosphonate and, thence, the formula-LXXII 2β-[3(S) or (R)-3-[(tetrahydropyran-2-yl)oxy]-4,4-difluoro-trans-1-octenyl]-5α-hydroxy-3α-[(tetrahydropyran-2-yl)oxyl]-1α-cyclopentaneacetaldehyde, γ-lactol.

When the phosphonate contains an asymmetric carbon atom, e.g. when the methylene between the carbonyl and $C_gH_{2g}$ is substituted with only one methyl or ethyl group, the phosphonate exists in either of two optically active forms (+ or −) or their racemic (dl) mixture. An optically active phosphonate is obtained by starting with an appropriate optically active isomer of the aliphatic acid. Methods of resolving these acids are known in the art, for example by forming salts with an optically active base such as brucine, separating the resulting diastereomers, and recovering the acids.

Following the procedure of Preparation 3 employing the optically active aldehyde LXVII of that example, each optically active phosphonate obtained from the list of aliphatic acid esters above in the second paragraph following Preparation 3 yields a corresponding optically active formula-LXXII γ-lactol.

Likewise following the procedure of Preparation 3, employing the optically active aldehyde LXVII of that example, each racemic phosphonate obtained from the above-mentioned list of aliphatic acid esters yields a pair of diastereomers, differing in their stereochemistry at the fourth carbon of the alkyl-terminated side-chain. These diastereomers are separated by conventional methods, e.g. by silica gel chromatography.

Again following the procedure of Preparation 3, employing the optically active aldehyde LXVII of that example, each of the optically inactive phosphonates obtained from the list of aliphatic acid esters above wherein there is no asymmetric carbon atom, i.e. $R_8$ and $R_9$ are the same, yields a corresponding optically active formula-LXXII γ-lactol.

Replacing the optically active aldehyde LXVII with the racemic aldehyde obtained after Preparation 2, and following the procedure of Preparation 3 using each of the optically active phosphonates described above, there is obtained in each case a pair of diastereomers which are separated by chromatography.

Likewise following the procedure of Preparation 3, employing the racemic aldehyde with each of the racemic phosphonates described above, there are obtained in each case two pairs of 3-oxo racemates which are separated into pairs of racemic compounds by methods known in the art, e.g. silica gel chromatography.

Again following the procedure of Preparation 3, employing the racemic aldehyde with each of the optically inactive phosphonates described above, there are obtained in each case a racemic product corresponding to formula LXXII.

Preparation 4 2β-[(3S)-4-Methyl-3-[(tetrahydropyran-2-yl)-oxy]-trans-1-octenyl]-5α-hydroxy-3α-[(tetrahydropyran-2-yl)oxy]1α-cyclopentaneacetaldehyde, γ-Lactol (Formula LXXII: Q₃ is H⌒OTHP, R₈ is methyl, R₉ is hydrogen, R₁₁ is n-butyl, and R₁₃ is THP).

Refer to Chart A. a. There is first prepared racemic dimethyl 2-oxo-3-methylheptylphosphonate,

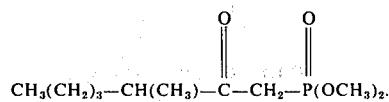

n-Butyllithium (150 ml.) is slowly added to a solution of dimethyl methylphosphonate (25.6 g.) in 475 ml. of tetrahydrofuran (THF) at about −65° C. To the mixture is added a solution of racemic ethyl 2-methylhexanoate (18.4 g.) in 50 ml. of THF, and the resulting mixture is stirred at −70° C. for 2 hr. Then 16 ml. of acetic acid is added and the mixture is concentrated under reduced pressure. The residue is mixed with dichloromethane (about 400 ml.) and water (about 50 ml.) shaken, and separated. The organic phase is dried over magnesium sulfate and concentrated. Distillation yields the desired phosphonate, 16.7 g., b.p. 126–129° C./1 mm.

b. Following the procedures of Preparation 3, but replacing the dimethyl 2-oxoheptylphosphonate of that preparation with the above racemic dimethyl 2-oxo-3-methylheptylphosphonate, there are obtained the corresponding formula-LXVIII, LXIX, LXX, LXXI, and LXXII compounds wherein $R_8$ is methyl and $R_9$ is hydrogen. See German Offenlegungsschrift 2217044, Derwent Reference No. 71483T-B.

Likewise following the procedures of Preparation 4 but replacing racemic ethyl 2-methylhexanoate with the ethyl esters of the (+) and (−) isomers of 2-methylhexanoic acid (see P.A. Levene et al., J. Biol. Chem. 70, 211 (1926) and 84, 571 (1929)) there are obtained the corresponding optically active (+) and (−) phosphonates and thence the optically active title compounds. Alternatively, the phosphonate is prepared by reaction of a mixed anhydride instead of an ester. See Fieser et al., "Reagents for Organic Synthesis", Vol. I, John Wiley and Sons, Inc, New York, 1967, p. 86. Thus, the (+) and (−) isomers of

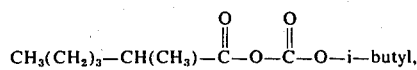

with butyllithium and dimethyl methylphosphonate yield the respective (+) and (−) phosphonates.

Likewise following the procedures of Preparation 4 but replacing ethyl 2-methylhexanoate with optically active or racemic ethyl 2-ethylhexanoate, there are obtained the corresponding optically active or racemic phosphonates and thence the corresponding formula-LXXII compounds wherein $R_8$ is ethyl and $R_9$ is hydrogen.

Preparation 5 2β-[(3S)-4,4-Dimethyl-3-[(tetrahydropyran-2-yl)oxy]-trans-1-octenyl]-5α-hydroxy-3α-[(tetrahydropyran-2-yl)oxy]-1α-cyclopentaneacetaldehyde, γ-Lactol (Formula LXXII: Q₃ is H⌒OTHP, R₈ and R₉ are methyl, R₁₁ is n-butyl, and R₁₃ is THP).

Refer to Chart A. a. There is first prepared dimethyl 2-oxo-3,3-dimethylheptylphosphonate

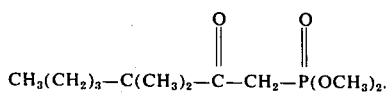

n-Butyllithium (400 ml.) is slowly added to a solution of dimethyl methylphosphonate (73.7 g) in 1.3 l. of tetrahydrofuran (THF) at about −66° C. To the mixture is added a solution of ethyl 2,2-dimethylhexanoate (53 g.) in 150 ml. of THF, and the resulting mixture is stirred at −70° C. for 2 hr. Then 46 ml. of acetic acid is added and the mixture is concentrated under reduced pressure. The residue is mixed with portions of dichloromethane (about 1.1 l.) and water (about 150 ml.), shaken, and separated. The organic phase is dried over magnesium sulfate and concentrated. Distillation yields the desired phosphonate, 41.6 g., b.p. 117°–120°C./1 mm.

b. Following the procedures of Preparation 3, but replacing the dimethyl 2-oxoheptylphosphonate of that preparation with the above dimethyl 2-oxo-3,3-dimethylheptylphosphonate, there are obtained the corresponding formula-LXVIII, LXIX, LXX, LXXI, and LXXII compounds wherein $R_8$ and $R_9$ are methyl. See German Offenlegungsschrift No. 2217044, Derwent Reference No. 71483T-B.

Preparation 6  2β-[(3S)-3[(Tetrahydropyran-2-yl)oxy]-trans-1-cis-5-octadienyl]-5α-hydroxy-3α-[(tetrahydropyran-2-yl)oxy]-1α-cyclopentaneacetaldehyde, γ-Lactol (Formula LXXIII of Chart B: $Q_3$ is 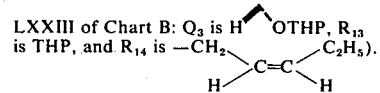 $R_{13}$ is THP, and $R_{14}$ is —CH₂\\_C=C\\_C₂H₅)

Refer to E. J. Corey et al., J. Am. Chem. Soc. 93, 1490 (1971). A solution of the hydroxy (S) - (+) phosphonium salt

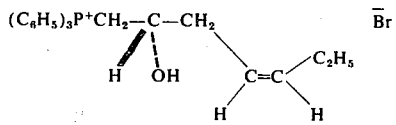

(6.6 g.) in 20 ml. of tetrahydrofuran is stirred under nitrogen with 2 equivalents of methyllithium first at about −70° C., then at −25° C. for about 30 min. The mixture is cooled to −78° C. and to it is added a solution of the 2β-carboxaldehyde-3α-[(tetrahydropyran-2-yl)-oxy]-5α-hydroxy-1α-cyclopentaneacetic acid, γ-lactone (2.5 g.) in 20 ml. of tetrahydrofuran. The mixture is stirred at about −78° C. for 5 min., then at 0° C. for 30 min. The product is separated by extraction into benzene, washing the benzene solution with dilute hydrochloric acid and water, drying over sodium sulfate, and concentrating. The residue is chromatographed on silica gel to yield the lactone. The bis(tetrahydropyranyl ether) is obtained in the conventional way using dihydropyran and pyridine hydrochloride. Treatment of the product with 2 equivalents of diisobutylaluminum hydride in toluene at −60° C. for 20 min., followed by separation, yields the title compound.

Preparation 7  2β-[(3S)-3-Methoxy-trans-1-octenyl]-5α-hydroxy-3α-[(tetrahydropyran-2-yl)oxy]-1α-cyclopentaneacetaldehyde, γ-Lactol (Formula LXXXII: $Q_4$ is 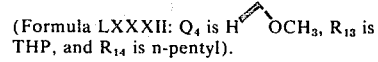 $R_{13}$ is THP, and $R_{14}$ is n-pentyl).

Refer to Chart D. A mixture of the formula-LXXX alpha hydroxy compound wherein $Q_2$ is

$R_{13}$ is THP, and $R_{14}$ is n-pentyl (2.0 g.), silver oxide (4.0 g.) and 50 ml. of methyl iodide is stirred and heated at reflux for 68 hr. The mixture is cooled and filtered, and the filtrate concentrated to a residue, 2.0 g. The residue is subjected to silica gel chromatography to yield the formula-LXXXI compound.

Thereafter following the procedures of Preparation 3 step e there is obtained the formula-LXXXII title compound γ-lactol.

Preparation 8  2β-[(3S)-3-[(Tetrahydropyran-2-yl)oxy]-3-methyl-trans-1-octenyl]-5α-hydroxy-3α-[(tetrahydropyran-2-yl)oxy]-1α-cyclopentaneacetaldehyde, γ-Lactol (Formula LXXXVII:

$Q_6$ is CH₃ 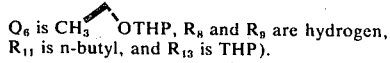 OTHP, $R_8$ and $R_9$ are hydrogen, $R_{11}$ is n-butyl, and $R_{13}$ is THP).

Refer to Chart E. A solution of the formula-LXVIII oxo compound wherein $R_8$ and $R_9$ are hydrogen, $R_{11}$ is n-butyl, and $R_{12}$ is benzoyl (Preparation 3, 0.2 g.) in 15 ml. of tetrahydrofuran is treated, with stirring at −78° C., with 3M methyl magnesium bromide in ether, added dropwise. After 2 hr. there is added dropwise to the mixture at −78° C. 10 ml. of saturated aqueous ammonium chloride. The mixture is warmed to 25° C. and diluted with diethyl ether and water. The organic phase is washed with brine, dried and concentrated to the mixed 15R and 15S formula-LXXXIV compounds, an oil, 0.21 g., having $R_f$ 0.2 (TLC on silica gel plate in 50% ethyl acetate-Skellysolve B).

Thereafter, following the procedures of Preparation 3 steps c-e and employing the alpha-hydroxy compound, there are obtained the formula-LXXXV and LXXXVI compounds and finally the formula-LXXXVII title compound.

Preparation 9  2β-[(3S)-3-[(Tetrahydropyran-2-yl)oxy]-trans-1-octenyl]-5α-hydroxy-1α-cyclopentaneacetaldehyde, γ-Lactol (Formula CVI: $Q_3$ is 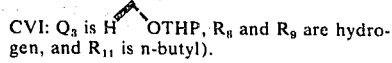 $R_8$ and $R_9$ are hydrogen, and $R_{11}$ is n-butyl).

a. Refer to Chart I. The formula-CII starting material, 3,3aβ, 4α, 5, 6, 5aβ-hexahydro-2-oxo-2H-cyclopenta[b]furan-4-carboxaldehyde is first prepared in optically active form. A solution of the racemic compound (E. J. Corey et al., Tetrahedron Lett. No. 49, 4753 (1971) 15.4 g.) and 1-ephedrine (16.5 g.) in 150 ml. of benzene is concentrated under reduced pressure to a residue. The residue is triturated with diethyl ether and then dissolved in isopropyl ether. The solution is chilled to yield crystals of one of the diastereomeric oxazolidines. The oxazolidine is hydrolyzed to the oxo compound and ephedrine by contact with water, preferably with an acid catalyst, as is known in the art (see Elderfeld Heterocyclic Compounds, Vol. 5, page 394, Wiley, N.Y. 1957). Thus, the above oxazolidine (1.3 g.) is stirred in a solution of tetrahydrofuran-water-acetic acid (25 ml.: 25 ml.: 5 ml.) for 4 hr. at about 25° C. under nitrogen. The solvents are removed under reduced pressure and the residue is mixed with 25 ml. of water. The mixture is extracted several times with benzene, and the combined benzene layers are washed with water, dried over sodium sulfate, and concentrated under reduced pressure to yield an optically active isomer of the formula-CII compound; called "the isomer of Preparation 9a" herein. Following the procedure of part a above, but replacing 1-ephedrine with d-ephedrine, there is obtained another diastereomeric oxazolidine which yields on hydrolysis an enantiomer of the isomer above; called "the isomer of Preparation 9a'" herein.

b. The formula-CIII compound is next prepared from dimethyl 2-oxoheptylphosphonate, following the procedure of Preparation 3a above, but replacing the formula-LXVII aldehyde of that preparation with the formula-CII isomer of negative rotation of Preparation 9a above.

c. The formula-CIV compound is obtained by reduction of the product of step b using zinc borohydride and following the procedure of Preparation 3b. The α and β isomers so obtained are separated and treated below.

d. The formula-CV tetrahydropyranyl ether is obtained from the α-isomer of part c following the procedure of Preparation 3d.

e. The title formula-CVI γ-lactol is finally obtained by reduction of the product of step d following the procedure of Preparation 3e.

Following the procedures of Preparation 9 steps d and e, but employing the β isomer of part c above, there are obtained the corresponding formula-CV and -CVI compound wherein $Q_4$ is

Following the procedures of Preparation 9, steps b-e but replacing the dimethyl 2-oxoheptylphosphonate of that preparation with the various-phosphonates within the scope of

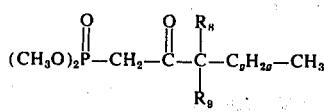

wherein $C_gH_{2g}$, $R_8$, and $R_9$ are as defined above, including the specific examples listed following Preparation 3 and in Preparations 4 and 5, there are obtained the corresponding formula-CIII, CIV, and CVI compounds wherein $Q_2$ and $Q_3$ are in either the α or β configuration. For example, there are obtained the following formula-CVI compounds:

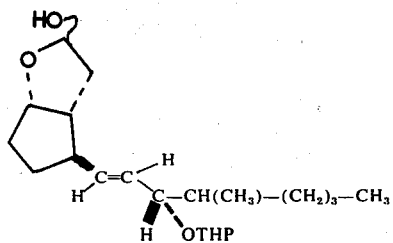

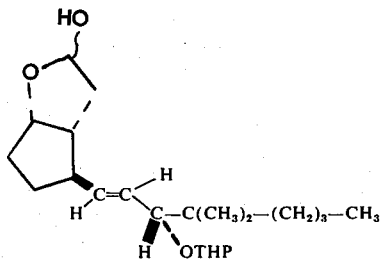

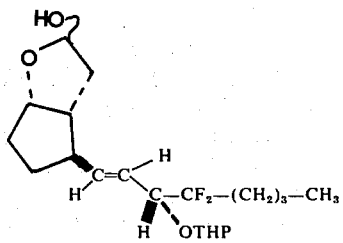

Likewise following the procedures of Preparation 9 steps b-e but replacing the optically active formula-CII aldehyde of that preparation with the corresponding racemic compound and employing the various phosphonates within the scope of

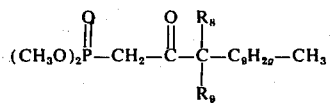

including the specific examples in and following Preparations 3, 4, and 5, there are obtained the racemic compounds corresponding to the formula-CIII, CIV, CV, and CVI compounds.

Preparation 10. 2β-[3(S)-3[(Tetrahydropyran-2-yl)oxy]-trans-1-cis-5-octadienyl]-5α-hydroxy-1α-cyclopentaneacetaldehyde, γ-Lactol
(Formula CVII of Chart J; $Q_3$ is
and $R_{14}$ is

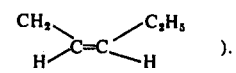

).

Following the procedure of Preparation 6 but replacing the 2β-carboxaldehyde of that preparation with the formula-CII 3,3aβ, 4α, 5, 6, 6aβ-hexahydro-2-oxo-2H-cyclopenta [b]-furan-4-carboxaldehyde (step a of Preparation 9, isomer of negative rotation) there is obtained the title compound.

---

Preparation 11   2β-[(3S)-5-Phenyl-3-[(tetrahydropyran-2-yl)oxy]-trans-1-pentenyl]-5α-hydroxy-3α-[(tetrahydropyran-2-yl)oxy]-1α-cyclopentaneacetaldehyde, γ-Lactol (Formula LXXII:

Q₃ is H͡ OTHP, R₈ and R₉ are hydrogen, R₁₁ is -CH₂-⟨‾⟩ and R₁₃ is THP).

--- a. Refer to Chart A. The phosphonate anion (ylid) is first prepared as follows. Dimethyl 2-oxo-4-phenyl-butylphosphonate (prepared by methods known in the art from dimethyl methylphosphonate and ethyl 3-phenylpropionate in the presence of butyllithium) (14.28 g.) is added to a suspension of sodium hydride (2.7 g.) in 250 ml. of tetrahydrofuran and stirring continued for 2 hr.

To the above suspension at 0° C. is added the formula-LXVII aldehyde, obtained without isolation from the formula-LXVI hydroxymethyl compound (Preparation 2, 6.0 g.) in benzene. The mixture is stirred for 2 hr., acetic acid (1.5 ml.) is added, and the mixture is concentrated under reduced pressure. The residue is taken up in ethyl acetate, washed with brine, dried and concentrated. Silica gel chromatography yields the formula-LXVIII compound, wherein R₈, R₉, R₁₁, and R₁₂ are defined in the heading above, 2.73 g., m.p. 118°–119–5° C., and having λ_{max}EtOH 229 mμ (26,700), 264 mμ (1200), 268 mμ (1150), 274 mμ, (1100), and 281 mμ (886).

b. To a mixture of zinc borohydride prepared from zinc chloride (anhydrous, 13.6 g.) and sodium borohydride (3.0 g.) in 120 ml. of 1,2-dimethoxyethane under nitrogen stirred for 2 hr. and then cooled to −10° C., is added the formula-LXVIII ketone above (8.1 g.) in 45 ml. of 1,2-dimethoxyethane. The mixture is stirred at 0° C. for 2 hr. and at about 25° C. for 1 hr. The mixture is cooled to 0°–5° C. and 19.5 ml. of water is added cautiously. After hydrolysis is complete, the mixture is shaken with 200 ml. of ethyl acetate and filtered. The filtrate is washed with brine, dried and concentrated under reduced pressure. The alpha and beta isomers are separated by silica gel chromatography, eluting with ethyl acetate-Skellysolve B (2:1). Fractions containing the α or β isomers as shown by TLC, are combined and concentrated to yield, respectively, 3.4 g. of formula-LXIX product where Q₂ is

H͡ OH and 2.75 g. of formula-LXIX product wherein Q₂ is

H͡ OH.

The LXIX-α product has m.p. 88°–90° C.

c. To a solution of the formula-LXIX benzoyloxy α-hydroxy compound above (3.3 g.) in 38 ml. of methanol is added potassium carbonate (1.11 g.) and the mixture is stirred for 1.3 hr. About 40 ml. of chloroform is added and the mixture is filtered. The filtrate is concentrated under reduced pressure. The residue is taken up in dichloromethane, washed with brine, dried, and concentrated. The residue is triturated with Skellysolve B and concentrated to yield the formula-LXX product (2.02 g.). The product crystallizes slowly on standing; m.p. 65°–67° C. (from ethyl acetate-Skellysolve B).

d. There is next prepared the formula-LXXI bis(tetrahydropyranyl ether) wherein Q₃ is

H͡ OTHP,

R₈ and R₉ are hydrogen,

R₁₁ is -CH₂-⟨‾⟩, and R₁₃ is THP. The formula-LXX compound above (1.985 g.) is treated with 5.95 ml. of dihydropyran in 45 ml. of dichloromethane in the presence of p-toluene-sulfonic acid (0.033 g.). After about 25 min. the mixture is washed with potassium bicarbonate solution, dried, and concentrated to give the formula-LXXI compound (4.4 g.) free of starting material by TLC.

e. To a solution of the above lactone in 45 ml. of toluene at −78° C. is added dropwise, while stirring, diisobutylaluminum hydride (3.9 ml.). Stirring is continued at −78° C. for 0.5 hr., whereupon a solution of 9 ml. of water in 17 ml. of tetrahydrofuran is added. After the mixture is stirred for an additional hour at about 25° C. it is filtered. The filtrate is washed with brine, dried, and concentrated to yield the formula-LXXII title compound, 4.39 g., on oil.

Following the procedures of steps c, d, and e above, but employing the formula-LXIX β-hydroxy compound from step b, there are obtained the formula-LXX, LXXI, and LXXII compounds wherein Q₂ is H͡ OH and Q₃ is H͡ OTHP.

Following the procedures of Preparation 11, but replacing the formula-LXVII aldehyde with the racemic compound corresponding to formula LXVII obtained following Procedure 2, there are obtained the racemic compounds corresponding to formula-LXXII.

Likewise, following the procedures of Preparation 11, but replacing the dimethyl 2-oxo-4-phenylbutyl-phosphonate of that preparation with the various phosphonates within the scope of

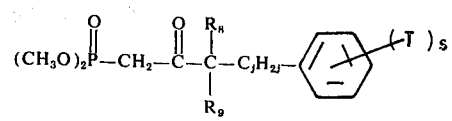

wherein $C_jH_{2j}$ is a valence bond or alkylene of one to 9 carbon atoms, inclusive, substituted with zero, one, or 2 fluoro, with one to 6 carbon atoms, inclusive, between $-CR_8R_9-$ and the ring; wherein T is alkyl of one to 4 carbon atoms, inclusive, fluoro, chloro, trifluoromethyl, or $-OR_{10}$, wherein $R_{10}$ is hydrogen or alkyl of one to 4 carbon atoms, inclusive, and $s$ is zero, one, 2, or 3, with the proviso that not more than two T's are other than alkyl and when s is 2 or 3 the T's are either the same or different, wherein $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro, there are obtained the corresponding formula-LXXII optically active γ-lactols and their racemic compounds wherein $Q_8$ is either

Those phosphonates are prepared by methods described herein or known in the art, utilizing for example the following aliphatic acid esters within the scope of

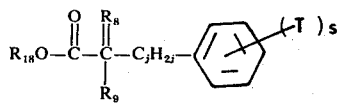

wherein $C_jH_{2j}$, $R_8$, $R_9$, s, and T are as defined above, and $R_{18}$ is methyl or ethyl, for example:
  methyl 2-phenylacetate
  ethyl 2-(p-chlorophenyl)acetate
  methyl 2-(o, p-dichlorophenyl)propionate
  methyl 2-fluoro-2-(p-tolyl)acetate
  ethyl 2-phenylhexanoate
  methyl 3-(p-chlorophenyl)propionate
  ethyl 3-(α,α,α-trifluoro-p-tolyl)propionate
  methyl 2-(m-methoxybenzyl)butyrate
  methyl 2,2-difluoro-3-phenylpropionate
  ethyl 4-phenylbutyrate
  ethyl 4-(p-chlorophenyl)butyrate
  methyl 4-(p-tolyl)butyrate
  methyl 4-(2-chloro-4-tolyl)butyrate
  methyl 2-methyl-4-(2,4-xylyl)butyrate
  methyl 5-phenylpentanoate
  ethyl 2,2-dimethyl-5-phenylpentanoate
  ethyl 3-(phenethyl)nonanoate
  methyl 6-phenylhexanoate
  methyl 7-phenylheptanoate
  methyl 3-phenyl-3-(n-propyl)octanoate
For example, methyl 2-phenylacetate yields dimethyl 2-oxo-3-phenylpropylphosphonate and, thence, the formula-LXXII 2β-[(3S)-4-phenyl-3-[(tetrahydropyran-2-yl)oxy]-trans-1-butenyl]-5α-hydroxy-3α-[(tetrahydropyran-2-yl)oxy]-1α-cyclopentaneacetaldehyde, γ-lactol. Likewise, ethyl 4-(p-chlorophenyl)butyrate yields dimethyl 2-oxo-5-(p-chlorophenyl)pentylphosphonate and, thence, the formula-LXXII 2β-[(3S)-6-phenyl-3-[(tetrahydropyran-2-yl)oxy]-trans-1-hexenyl]-5α-hydroxy-3α-[(tetrahydropyran-2-yl)oxy]-1α-cyclopentaneacetaldehyde, γ-lactol.

When the phosphonate contains an asymmetric carbon atom, e.g. when the methylene between the carbonyl and $C_jH_{2j}$ is substituted with only one methyl or ethyl group, the phosphonate exists in either of two optically active forms (+ or −) or their racemic (dl) mixture. An optically active phosphonate is obtained by starting with an appropriate optically active isomer of the aliphatic acid. Methods of resolving these acids are known in the art, for example by forming salts with an optically active base such as brucine, separating the resulting diastereomers, and recovering the acids.

Following the procedure of Preparation 11, employing the optically active aldehyde LXVII of that example, each optically active phosphonate obtained from the list of aliphatic acid esters above in the third paragraph following Preparation 11 yields a corresponding optically active formula-LXXII γ-lactol.

Likewise following the procedure of Preparation 11, employing the optically active aldehyde LXVII of that example, each racemic phosphonate obtained from the abovementioned list of aliphatic acid esters yields a pair of diastereomers, differing in their stereochemistry at the fourth carbon of the phenoxy-terminated side-chain. These diastereomers are separated by conventional methods, e.g. by silica gel chromatography.

Again following the procedure of Preparation 11, employing the optically active aldehyde LXVII of that example, each of the optically inactive phosphonates obtained from the list of aliphatic acid esters above wherein there is no asymmetric carbon atom, i.e. $R_8$ and $R_9$ are the same, yields a corresponding optically active formula-LXXII γ-lactol.

Replacing the optically active aldehyde LXVII with the racemic aldehyde obtained after Preparation 2, and following the procedure of Preparation 11 using each of the optically active phosphonates described above, there is obtained in each case a pair of diastereomers which are separated by chromatography.

Likewise following the procedure of Preparation 11, employing the racemic aldehyde with each of the racemic phosphonates described above, there are obtained in each case two pairs of 3-oxo-racemates which are separated into pairs of racemic compounds by methods known in the art, e.g. silica gel chromatography.

Again following the procedure of Preparation 11, employing the racemic aldehyde with each of the optically inactive phosphonates described above, there are obtained in each case a racemic product corresponding to formula-LXXII.

Preparation 12  2β-[(3S)-4-Phenoxy-3-8(tetrahydropyran-2-yl)-oxy]-trans-1-butenyl]-5α-hydroxy-3α-[(tetrahydropyran-2-yl)oxy]-1α-cyclopentaneacetaldehyde, γ-Lactol (Formula LXXII: $Q_3$ is H̸ OTHP, $R_8$ and $R_9$ are hydrogen, $R_{11}$ is —O—⟨phenyl⟩, and $R_{13}$ is THP).

Refer to Chart A. a. There is first prepared dimethyl 3-phenoxyacetonylphosphonate. A solution of dimethyl methylphosphonate (75 g.) in 700 ml. of tetrahydrofuran is cooled to −75° C. under nitrogen and n-butyllithium (400 ml. of 1.6 molar solution of hexane) is added, keeping the temperature below −55° C.

The mixture is stirred for 10 min. and to it is slowly added phenoxyacetyl chloride (44 g.), again keeping the temperature below −55° C. The reaction mixture is stirred at −75° C. for 2 hr., then at about 25° C. for 16 hr. The mixture is acidified with acetic acid and concentrated under reduced pressure. The residue is partitioned between diethyl ether and water, and the organic phase is dried and concentrated to the above-named intermediate, 82 g. Further treatment by silica gel chromatography yields an analytical sample having NMR peaks at 7.4–6.7 (multiplet), 4.78 (singlet), 4.8 and 4.6 (two singlets), and 3.4–3.04 (doublet)δ.

b. The phosphonate anion (ylid) is then prepared as follows. Dimethyl 3-phenoxyacetonylphosphonate (step a, 9.3 g.) is added in portions to a cold (5° C.) mixture of sodium hydride (1.75 g., 50%); in 250 ml. of tetrahydrofuran, and the resulting mixture is stirred for 1.5 hr. at about 25° C.

c. To the mixture of step b is added the cold solution of the formula-LXVII 2β-carboxaldehyde of Preparation 2, and the resulting mixture is stirred about 1.6 hr. Then 3 ml. of acetic acid is added and the mixture is concentrated under reduced pressure. A solution is prepared from the residue in 500 ml. of ethyl acetate, washed with several portions of water and brine, and concentrated under reduced pressure. The residue is subjected to silica gel chromatography, eluting with ethyl acetate-Skellysolve B (isomeric hexanes) (3:1). Those fractions shown by TLC to be free of starting material and impurities are combined and concentrated to yield the formula-LXVIII compound, 1.7 g.; NMR peaks at 5.0–8.2 and 4.7 (singlet)δ.

d. Sodium borohydride (1.05 g.) is added in portions to a cold (0° C.) mixture of zinc chloride (4.4 g.) and 35 ml. of 1,2-dimethoxyethane under nitrogen. Stirring is continued at about 25° C. for 20 hr. Then the mixture is cooled to −20° C. and the formula-LXVIII 3-oxo compound (step c, 2.6 g. in 10 ml. of 1,2-dimethoxyethane) is added. The mixture is stirred at −20° C. for 6 hr., and at 25° C. for 30 min. The mixture is again cooled to −20° C. and 5 ml. of water is added dropwise. The mixture is shaken with 100 ml. of brine and ethyl acetate and the organic layer is dried and concentrated under reduced pressure. The residue is chromatographed on silica gel, eluting with ethyl acetate-Skellysolve B (isomeric hexanes) (3:1). Those fractions shown by TLC to be free of starting material and impurities are combined and concentrated to yield the 3α-hydroxy formula-LXIX compound, 1.1 g.; NMR peaks at 6.6–8.0, 5.52–5.87, and 3.83 δ. Other fractions yield the more polar 3β-hydroxy formula-LXIX compound, 0.8 g.; NMR at 6.6–8.0, 5.52–5.87, and 3.83 δ.

e. The formula-LXIX 3α-hydroxy compound (step d, 1.35 g.) in 22 ml. of anhydrous methanol is stirred with potassium carbonate (0.48 g.) for 1 hr. at about 25° C. Then 15 ml. of chloroform is added and the solvent removed under reduced pressure. A solution of the residue in 70 ml. of chloroform is shaken with 10 ml. of water containing potassium hydrogen sulfate (0.5 g.), then with brine, and concentrate. The residue is washed with several portions of Skellysolve B (isomeric hexanes) and dried to yield the formula-LXX benzoyloxy-free compound, i.e. 3α,5α-dihydroxy-2β-(3α-hydroxy-4-phenoxy-trans-1-butenyl)-1α-cyclopentaneacetic acid, γ-lactone, 0.4 g.

f. The formula-LXX compound from part e above is converted to the formula-LXXI bis(tetrahydropyranyl ether) by reaction with 0.8 ml. of dihydropyran in 10 ml. of dichloromethane in the presence of pyridine hydrochloride (about 0.03 g.). In about 2.5 hr. the mixture is filtered and concentrated to the formula-LXXI product, 0.6 g.; having no infrared absorption at 3300 cm⁻¹.

g. The formula-LXXII title compound is prepared as follows. Diisobutylaluminum hydride (4.8 ml. of a 10% solution in toluene) is added dropwise to a stirred solution of the formula-LXXI bis(tetrahydropyranyl ether) from step f above in 8 ml. of toluene cooled to −78° C. Stirring is continued at −78° C. for 0.5 hr., whereupon a solution of 3 ml. of tetrahydrofuran and 1 ml. of water is added cautiously. After the mixture warms to 25° C. it is filtered and the filtrate washed with brine, dried, and concentrated to the mixed alpha and beta hydroxy isomers of the formula-LXXII title compounds, 0.33 g., having infrared absorption at 3300 cm⁻¹.

Following the procedures of Preparation 12 steps e-g, but using the formula-LXIX 3β-hydroxy-4-phenoxy isomer of step d, there is obtained the corresponding 3β-hydroxy formula-LXXII compound, i.e. wherein $Q_3$ is

Following the procedure of Preparation 12, but replacing the optically active formula-LXVII aldehyde with the racemic aldehyde obtained after Preparation 2, there is obtained the racemic 3-hydroxy-4-phenoxy-1-butenyl compound corresponding to formula LXXII.

Following the procedure of Preparation 12, but replacing phenoxyacetyl chloride in step a with each of the aliphatic acid esters or acid chlorides within the scope of

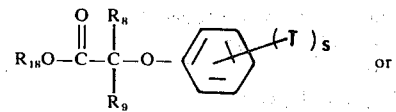   or

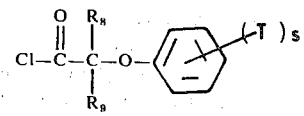

wherein $R_8$ and $R_9$ are hydrogen or alkyl of one to 4 carbon atoms, being the same or different, wherein $R_{18}$ is methyl or ethyl and wherein T is alkyl of one to 4 carbon atoms, inclusive, fluoro, chloro, trifluoromethyl, or —$OR_{10}$, wherein $R_{10}$ is hydrogen or alkyl of one to 4 carbon atoms, inclusive, and $s$ is zero, one, 2, or 3, with the proviso that not more than two T's are other than alkyl and when $s$ is 2 or 3 the T's are either the same or different, for example:
    methyl p-fluorophenoxyacetate
    methyl 2-phenoxypropionate
    methyl 2-methyl-2-phenoxypropionate
    ethyl 2-phenoxybutyrate
    methyl 2-ethyl-2-phenoxybutyrate
    ethyl 2-methyl-2-phenoxybutyrate
    methyl 2-(p-tolyloxy)acetate
    methyl 2-(p-fluorophenoxy)propionate ethyl 2-(o,p-dichlorophenoxy)-2-methyl-propionate
ethyl 2-(α,α,α-trifluoro-p-tolyloxy)butyrate
methyl 2-(m-methoxyphenoxy)-2-methyl-butyrate and
methyl 2-phenoxyhexanoate, there are obtained the corresponding phosphonate and, thence, the formula-LXXII γ-lactol.

For example, methyl 2-phenoxypropionate yields dimethyl 2-oxo-3-phenoxybutylphosphonate and, thence, the formula-LXXII 3α-benzoyloxy-5α-hydroxy-2β-(3-hydroxy-4-phenoxy-trans-1-pentenyl)-1α-cyclopentaneacetic acid γ-lactone. Likewise, ethyl 2-(o,p-dichlorophenoxy)-2-methyl-propionate yields dimethyl 2-oxo-3-(o,p-dichlorophenoxy)-3-methyl-butylphosphonate and, thence, the formula-LXXII γ-lactone.

| Preparation 13 | 2β-[(3S)-5-Phenyl-3-[(tetrahydropyran-2-yl)oxy]-trans-1-pentenyl-5α-hydroxy-1α-cyclopentaneacetaldehyde, γ-Lactol  (Formula CVI: Q₄ is H  OTHP, R₈ and R₉ are hydrogen, and R₁₁ is  $-CH_2-$). |
|---|---|

Refer to Chart I. Following the procedures of preparation 11 but replacing the formula-LXVII aldehyde of that preparation with the formula-CII 3,3aβ,4α,5,6,6aβ-hexahydro-2-oxo-2H-cyclopenta[b] furan-4-carboxaldehyde (step a of Preparation 9, isomer of negative rotation), there is obtained the title compound.

| Preparation 14 | 2β-[(3S)-4-Phenoxy-3-[(tetrahydropyran-2-yl)-oxy]-trans-1-butenyl]-5α-hydroxy-1α-cyclopentaneacetaldehyde, γ-Lactol (Formula CVI:  Q₃ is H  OTHP, R₈ and R₉ are hydrogen, and R₁₁ is $-O-$, |
|---|---|

Refer to Chart I. Following the procedures of Preparation 12 but replacing the formula-LXVII aldehyde of that preparation with the formula-CII 3,3a-, 4α,5,5-,5aβ-hexahydro-2-oxo-2H-cyclopenta[b] furan-4-carboxaldehyde (step a of Preparation 9, isomer of negative rotation), there is obtained the title compound.

EXAMPLE 1

2{2β-[(3S)-3-[Tetrahydropyran-2-yl)oxy]-trans-1-octenyl]-5α-hydroxy-3α-[(tetrahydropyran-2yl)-oxy]-1α-cyclopentyl ethanol.}(Formula LXXIV: Q₃ is

H  OTHP wherein THP is tetrahydropyranyl, R₁₃ is THP, and R₁₄ is n-pentyl).

Refer to Chart B. A mixture of the formula-LXXIII 2β-[(3S)-3-[(tetrahydropyran-2-yl)oxy]-trans-1-octenyl]-5α-hydroxy-3α-[(tetrahydropyran-2-yl]-1α-acetaldehyde, γ-lactol (Preparation 3, 6.3 g.) and 50 ml. of 95% ethanol is treated at 0° C., while stirring, with a solution of sodium borohydride (0.6 g.) in 10 ml. of water added over a 1-minute period. The mixture is stirred at 0° C. for 10 min. and is then shaken with 20 ml. of water, 250 ml. of ethyl acetate, and 150 ml. of brine. The organic phase is washed with brine, dried, and concentrated under reduced pressure to the title compound, 6.3 g., having R_f 0.2 (TLC on silica gel plate in 1:1 ethyl acetate-Skellysolve B).

EXAMPLE 2

5-Oxa-PGF$_{1α}$, Methyl Ester, 11,15-Bis(tetrahydropyranyl ether) (Formula LXXV: Q₃ is

H  OTHP;

R₂, R₃, R₄, and R₅ are hydrogen; R₁₃ is THP; and R₁₄ is n-pentyl).

Refer to Chart B. A solution of potassium t-butoxide (1.77 g.) in 30 ml. of tetrahydrofuran is mixed at 0° C., while stirring, with a solution of the formula-LXXIV 2-{2β-[(3S)-3-[(tetrahydropyran-2-yl)oxy]-trans-1-octenyl]-5α-hydroxy-3α-[(tetrahydropyran-2-yl)oxy]-1α-cyclopentyl}-ethanol (Example 1, 5.8 g.) in 30 ml. of tetrahydrofuran. The mixture is stirred at 0° C. for 5 min. and then 5 ml. of trimethyl ortho-4-bromobutyrate (Preparation 1) is added. Stirring is continued at 0° C. for 2 hr. and at about 25° C. for 16 hr. To the mixture is added 30 ml. of dimethylformamide and 0.5 g. of potassium t-butoxide and the mixture is stirred 20 hr. Some of the solvent is removed under reduced pressure and the residue is shaken with water and diethyl ether-dichloromethane (3:1). The organic phase is washed with water and brine, dried, and concentrated. The residue, containing the ortho ester, is dissolved in 60 ml. of methanol at 0° C., and treated with 15 ml. of cold water containing 2 drops of concentrated hydrochloric acid. The mixture is stirred at 0° C. for 5 min. and shaken with 200 ml. of diethyl ether, 50 ml. of dichloromethane, and 200 ml. of brine. The organic phase is washed with brine, dried and concentrated under reduced pressure. The residue is subjected to silica gel chromatography, eluting with ethyl acetate-SKellysolve B mixtures, to yield the title compound, 1.35 g., having NMR peaks at 5.3–5.62, 4.68, and 3.63 δ.

EXAMPLE 3

5-Oxa-PGF$_{1α}$, Methyl Ester (Formula XXVII: C$_g$H$_{2g}$ is trimethylene; Q₁ is

H  OH;

R₁ is methyl; R₂, R₃, R₄, R₅, R₈, and R₉ are hydrogen; and ~ is alpha).

Refer to Chart B. A mixture of the formula-LXXV 5-oxa-PGF$_{1α}$, methyl ester, 11,15-bis(tetrahydropyranyl ether) (Example 2, 1.55 g.) in 40 ml. of acetic acid, 20 ml. of water, and 6 ml. of tetrahydrofuran is stirred at 40° C. for 4 hr. The mixture is diluted with ethyl acetate and the organic phase is washed with cold dilute sodium hydroxide solution, water, and brine, dried and concentrated under reduced pressure. The residue is subjected to silica gel chromatography, eluting with ethanol (5–10%)-dichloromethane mixtures, to obtain the title compound, 0.33 g., having NMR peaks at 5.39–5.55, 3.69, and 3.38–3.6 δ; and mass spectral peaks (for the trimethylsilyl derivative) at 588.3738, 573, 577, 498, 483, 471, 427, 408, and 337.

EXAMPLE 4

5-Oxa-16-methyl-PGF$_{1\alpha}$, Methyl Ester (Formula XXVII: C$_g$H$_{2g}$ is trimethylene; Q$_1$ is

R$_1$ and R$_8$ are methyl; R$_2$, R$_3$, R$_4$, R$_5$, and R$_9$ are hydrogen; and ~ is alpha).

Following the procedures of Examples 1–3 but replacing the formula-LXXIII γ-lactol starting material of Example 1 with the formula-LXXII title compound of Preparation 4, there are obtained the corresponding title compounds.

EXAMPLE 5

5-Oxa PGF$_{1\alpha}$ -type Compounds within the scope of Formula XXVII.

Following the procedures of Examples 1, 2, and 3, but replacing the Preparation-3 -γ-lactol of Example 1 with each of the appropriate formula-LXXII γ-lactols identified in and following Preparation 3, there are obtained the corresponding 5-oxa PGF$_{1\alpha}$ -type compounds, both optically active and racemic, wherein Q$_1$ is either

including their methyl esters, for example:
5-oxa-19,20-dinor-PGF$_{1\alpha}$
5-oxa-16-methyl-19,20-dinor-PGF$_{1\alpha}$
5-oxa-20-nor-PGF$_{1\alpha}$
5-oxa-16-ethyl-20-nor-PGF$_{1\alpha}$
5-oxa-17-methyl-PGF$_{1\alpha}$
5-oxa-16,17-diethyl-PGF$_1$
5-oxa-18-ethyl-PGF$_{1\alpha}$
5-oxa-20-methyl-PGF$_{1\alpha}$
5-oxa-17,20-dimethyl-PGF$_{1\alpha}$
5-oxa-20,20-dimethyl-PGF$_{1\alpha}$
5-oxa-20-ethyl-PGF$_{1\alpha}$
5-oxa-20-(n-propyl)-PGF$_{1\alpha}$
5-oxa-17,20-bis(n-propyl)-PGF$_{1\alpha}$
5-oxa-16-fluoro-19,20-dinor-PGF$_{1\alpha}$
5-oxa-16,16-difluoro-19,20-dinor-PGF$_{1\alpha}$
5-oxa-16-fluoro-17-methyl-19,20-dinor-PGF$_{1\alpha}$
5-oxa-16-fluoro-20-nor-PGF$_{1\alpha}$
5-oxa-16,16-difluoro-PGF$_{1\alpha}$
5-oxa-16-fluoro-17-methyl-PGF$_{1\alpha}$
5-oxa-16-fluoro-18-ethyl-PGF$_{1\alpha}$
5-oxa-16-fluoro-20-methyl-PGF$_{1\alpha}$
5-oxa-16-fluoro-20,20-dimethyl-PGF$_{1\alpha}$
5-oxa-16,16-difluoro-17,20-dimethyl-PGF$_{1\alpha}$
5-oxa-16-fluoro-20-ethyl-PGF$_{1\alpha}$
5-oxa-16,16-difluoro-20-(n-propyl)-PGF$_{1\alpha}$ and
5-oxa-16-fluoro-17,20-bis(n-propyl)-PGF$_{1\alpha}$.

EXAMPLE 6

5-Oxa-PGE$_1$, Methyl Ester (Formula XXI: C$_g$H$_{2g}$ is trimethylene; Q$_1$ is

R$_1$ is methyl; and R$_2$, R$_3$, R$_4$, R$_5$, R$_8$, and R$_9$ are hydrogen).

Refer to Chart C. There is first prepared 5-oxa-PGE$_1$, methyl ester, 11,15-bis(tetrahydropyranyl ether). A solution of the formula-LXXV 5-oxa-PGF$_{1\alpha}$, methyl ester, 11,15-bis(tetrahydropyranyl ether) Example 2, 1.35 g.) in 30 ml. of acetone is treated at −20° C., while stirring, with 2.0 ml. of Jones reagent. The mixture is stirred at −20° C. for 20 min. and then diluted with 350 ml. of ethyl acetate. The mixture is washed with water and brine, dried, and concentrated under reduced pressure. The residue is subjected to silica gel chromatography, eluting with 50% ethyl acetate in Skellysolve B, to yield the intermediate 5-oxa-PGE$_1$, methyl ester, 11,15-bis(tetrahydropyranyl ether), 1.05 g.

The above intermediate is treated with 25 ml. of acetic acid, 12.5 ml. of water, and 2 ml. of tetrahydrofuran at 40° C. for 4 hr. The mixture is diluted with 300 ml. of ice cold (0° C.) ethyl acetate and washed with a slight deficiency ice-cold dilute sodium hydroxide solution, cold dilute sodium bicarbonate solution, and brine, then dried and concentrated under reduced pressure. The residue is subjected to silica gel chromatography, eluting with 1–7% methanol in ethyl acetate, to yield the title compound, 0.50 g., having NMR peaks at 5.58–5.7, 3.69, and 3.33–3.62 δ; and mass spectral peaks at 352.2228, 339, 334, 321, and 299.

EXAMPLE 7

5-Oxa-PGF$_{1\alpha}$, Methyl Ester (Formula XXVII: C$_g$H$_{2g}$ is trimethylene; Q$_1$ is

R$_1$ is methyl; R$_2$, R$_3$, R$_4$, R$_5$, R$_8$, and R$_9$ are hydrogen; and ~ is alpha); and 5-Oxa-PGF$_{1\beta}$, Methyl Ester (Formula XXVII: ~ is beta).

Refer to Chart C. The formula-LXXVII 5-oxa-PGE$_1$, methyl ester (Example 6, 0.2 g.) is treated in 6 ml. of methanol at 0° C., while stirring, with a solution of 50 mg. of sodium borohydride in 0.5 ml. of water. The mixture is stirred at 0° C. for 10 min. and then diluted with 100 ml. of ethyl acetate. The organic phase is washed with brine, dried, and concentrated under reduced pressure. The residue is subjected to silica gel chromatography eluting with 5–20% ethanol in chloroform. The first 200 ml. of eluant are discarded and then 10 ml. fractions are collected. Fractions 22–28 yield 5-oxa-PGF$_{1\alpha}$, methyl ester, 0.05 g., having identical properties with those of the product of Example 3. Fractions 29–47 yield 5-oxa-PGF$_{1\beta}$, methyl ester, 0.1 g., m.p. 80°–81° C. (recrystallized from diethyl ether-Skellysolve B), having NMR peaks at 5.43–5.58, 3.68, and 3.40–3.61 δ, and mass spectral peaks identical with those of the corresponding PGF$_{1\alpha}$ -type compound.

EXAMPLE 7A

5-Oxa-PGF$_{1\alpha}$ (Formula XXVII: C$_g$H$_{2g}$ is trimethylene; Q$_1$ is

$R_1$, $R_2$, $R_3$, $R_4$, $R_5$, $R_8$, and $R_9$ are hydrogen; and ~ is alpha).

A mixture of 5-oxa-PGF$_{1\alpha}$, methyl ester (Example 7, 0.38 g.), potassium carbonate (0.2 g.) 10 ml. of methanol, and 1 ml. of water is stirred at about 25° C. for 16 hr. and then concentrated under reduced pressure. The residue is shaken with ethyl acetate and dilute hydrochloric acid, and the organic phase is washed with brine, dried and concentrated. The residue is subjected to silica gel chromatography, eluting with 5–15% methanol in ethyl acetate, to yield the title compound, 0.115 g., having $R_f$ 0.46 (TLC on silica gel in methanol-acetic acid- chloroform (1:1:8)), and mass spectral peaks at 575, 556, 485, 466, and 395.

EXAMPLE 8

5-Oxa-PGA$_1$, Methyl Ester (Formula XXXIII: $C_gH_{2g}$ is trimethylene; $Q_1$ is

$R_1$ is methyl; and $R_2$, $R_3$, $R_4$, $R_5$, $R_8$, and $R_9$ are hydrogen).

Refer to Chart H. A solution of 5-oxa-PGE$_1$, methyl ester (Example 6, 0.2 g.) in a mixture of glacial acetic acid (9 ml.) and water (1 mk) is heated under nitrogen at 60° C. for 18 hr. Then, the acetic acid and water are evaporated under reduced pressure, and the residue is subjected to silica gel chromatography to yield the title compound.

EXAMPLE 9

5-Oxa-PGB$_1$ (Formula XXXVI: $C_gH_{2g}$ is trimethylene; $Q_1$ is

and $R_1$, $R_2$, $R_3$, $R_4$, $R_5$, $R_8$, and $R_9$ are hydrogen).

Refer to Chart H. A solution of 5-oxa-PGE$_1$, methyl ester (Example 6, 0.2 g.) in 100 ml. of 50% aqueous ethanol containing 10 grams of potassium hydroxide is kept at 25° C. for 10 hr. under nitrogen. Then, the solution is cooled to 10° C. and neutralized by addition of 3N. hydrochloric acid at 10° C. The resulting solution is extracted repeatedly with ethyl acetate, and combined ethyl acetate extracts are washed with water and then with brine, dried, and concentrated to give the title compound.

EXAMPLE 10

2{2β-[(3S)-4,4-Dimethyl-3-[(tetrahydropyran-2-yl)oxy]-trans-1-octenyl]-5α-hydroxy-3α-[(tetrahydropyran-2-yl)oxy]-1α-cyclopentyl -ethanol (Formula LXXIV: $Q_3$ is

$R_{13}$ is THP, and $R_{14}$ is

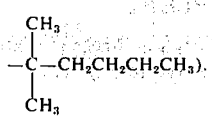

Refer to Chart B. A mixture of the formula-LXXIII 2β-[(3S)-4,4-dimethyl-3-[(tetrahydropyan-2-yl)oxy]-trans-1-octenyl]-5α-hydroxy-3α-[(tetrahydropyran-2-yl)oxy]-1α-acetaldehyde, γ-lactol (Preparation 5, 6.1 g.) and 60 ml. of 95% ethanol is treated at 0° C., while stirring, with a solution of sodium borohydride (0.7 g.) in 10 ml. of water. The mixture is stirred at 0° C. for 10 min. and is then shaken with 30 ml. of water, 300 ml. of ethyl acetate, and 150 ml. of brine. The organic layer is washed with brine, dried, and concentrated under reduced pressure to the title compound, 6.1 g., having $R_f$ 0.39 (TLC on silica gel plate in ethyl acetate), and NMR peaks at 5.34–5.66, 4.70, and 0.81–0.92 δ.

EXAMPLE 11

16,16-Dimethyl-5-oxa-PGF$_{1\alpha}$, Methyl Ester, 11,15-Bis(tetrahydropyranyl ether) (Formula-LXXV: $Q_3$ is

$R_2$, $R_3$, $R_4$, and $R_5$ are hydrogen; $R_{13}$ is THP; and $R_{14}$ is

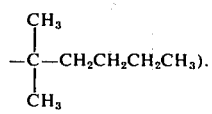

Refer to Chart B. A solution of the formula-LXXIV 2-{2β-[(3S)-4,4-dimethyl-3-[(tetrahydropyran-2-yl)oxy]-trans-1-octenyl]-5α-hydroxy-3α-[(tetrahydropyran-2-yl)oxy]-1α-cyclopentyl}ethanol (Example 10, 6.1 g.) in 25 ml. of tetrahydrofuran is treated at −15° C., while stirring, with 8.76 ml. of 1.6 M n-butyllithium over a 3-min. period. The mixture is stirred at 0° C. for 5 min. and then treated with 25 ml. of hexamethylphosphoramide and 5 ml. of trimethyl ortho-4-bromobutyrate (Preparation 1). The mixture is stirred at about 25° C. for 16 hr. and is then shaken with diethyl ether and water. The organic phase is washed with brine, dried, and concentrated under reduced pressure.

The residue, containing the ortho ester, is dissolved in 100 ml. of methanol, previously cooled to 0° C., and treated with 25 ml. of cold water containing 5 drops of concentrated hydrochloric acid. The mixture is stirred at 0° C. for 5 min. and shaken with 300 ml. of diethyl ether, 100 ml. of dichloromethane, and 200 ml. of brine. The organic phase is washed with brine, dried and concentrated under reduced pressure. The residue is subjected to silica gel chromatography, eluting with 30–50% ethyl acetate in Skellysolve B, to yield the title compound, 2.41 g., having $R_f$ 0.50 (TLC on silica gel plate in 50% ethyl acetate in Skellysolve B), and having NMR peaks at 5.32–5.62, 4.70, 3.68, 3.37–3.57, and 0.82–0.91 δ.

EXAMPLE 12

16,16-Dimethyl-5-oxa-PGF$_{1\alpha}$, Methyl Ester (Formula XXVII: C$_g$H$_{2g}$ is trimethylene; Q$_1$ is

R$_1$, R$_8$, and R$_9$ are methyl; R$_2$, R$_3$, R$_4$, and R$_5$ are hydrogen; and ~ is alpha).

Refer to Chart B. A solution of the formula-LXXV 16,16-dimethyl-5-oxa-PGF$_{1\alpha}$, methyl ester, 11-15-bis(tetrahydropyranyl ether) (Example 11, 2.4 g.), 50 ml. of acetic acid, 25 ml. of water, and 10 ml. of tetrahydrofuran is stirred at 40° C. for 1 hr. The mixture is diluted with 300 ml. of cold ethyl acetate and shaken with a mixture of 50 ml. of 50% aqueous sodium hydroxide solution in 300 ml. of ice and water. The organic phase is washed with brine, dried and concentrated under reduced pressure. The residue is subjected to silica gel chromatography, eluting with 0-3% ethanol in ethyl acetate, to obtain the title compound, 0.59 g., having R$_f$ 0.42 (TLC on silica gel plate in 5% ethanol in ethyl acetate), NMR peaks at 5.40-5.62, 3.69, 3.37-3.57, and 0.83-0.89 δ; and mass spectral peaks at 616, 601.3797, 526, 517, 499, 427 and 337.

EXAMPLE 13

16,16-Dimethyl-5-oxa-PGE$_1$, Methyl Ester (Formula XXI: C$_g$H$_{2g}$ is trimethylene; Q$_1$ is

R$_1$, R$_8$, and R$_9$ are methyl; and R$_2$, R$_3$, R$_4$, and R$_5$ are hydrogen).

Refer to Chart C. There is first prepared 16,16-dimethyl-5-oxa-PGE$_1$, methyl ester, 11,15-bis(tetrahydropyranyl ether). A solution of the formula-LXXV 16,16-dimethyl-5-oxa-PGF$_{1\alpha}$, methyl ester, 11,15-bis(tetrahydropyranyl ether) (Example 11, 1.6 g.) in 40 ml. of acetone is treated at −20° C., while stirring, with 2.5 ml. of Jones reagent. The mixture is stirred at −21° C. for 20 min. and then shaken with 300 ml. of ethyl acetate and 200 ml. of cold water. The organic phase is washed with water and brine, dried, and concentrated under reduced pressure. The residue is subjected to silica gel chromatography, eluting with 40% ethyl acetate in hexane, to yield the intermediate 16,16-dimethyl-5-oxa-PGE$_1$, methyl ester, 11,15-bis(-tetrahydropyranyl ether), 1.10 g., having R$_f$ 0.70 (TLC on silica gel plate in 50% ethyl acetate in Skellysolve B), and NMR peaks at 5.48-5.74, 4.68, 3.63, 3.28-3.50, and 0.83-0.92 δ.

The above intermediate is treated with 25 ml. of acetic acid, 12.5 ml. of water, and 4 ml. of tetrahydrofuran at 40° C. for 4 hr. The mixture is diluted with 250 ml. of ice cold (0° C.) ethyl acetate and shaken with about 200 ml. of crushed ice and water containing 20 ml. of 50% aqueous sodium hydroxide solution. The organic phase is washed with cold dilute sodium bicarbonate solution and brine, dried, and concentrated under reduced pressure. The residue is subjected to silica gel chromatography, eluting with ethyl acetate, to yield the title compound, 0.35 g., having R$_f$ 0.43 (TLC on silica gel plate in ethyl acetate), NMR peaks at 5.58-5.80, 3.68, 3.29-3.50, and 0.84-0.90 δ; and mass spectral peaks at 542, 527.3211, 443, 425 and 353.

EXAMPLE 14

5-Oxa-17,18-dehydro-PGF$_{1\alpha}$, Methyl Ester (Formula XXVIII: Q$_1$ is

R$_1$ is methyl; R$_2$, R$_3$, R$_4$, and R$_5$ are hydrogen; and ~ is alpha).

Refer to Chart B. Following the procedures of Examples 1, 2, and 3, but replacing the formula-LXXIII γ-lactol starting material of Example 1 with the formula-LXXIII title compound of Preparation 6, there is obtained the formula-XXVIII title compound.

EXAMPLE 15

5-Oxa-PGF$_{1\alpha}$, 15-Methyl Ether, Methyl Ester (Formula XXVII: C$_g$H$_{2g}$ is trimethylene; Q$_1$ is

R$_1$ is methyl; R$_2$, R$_3$, R$_4$, R$_5$, R$_8$, and R$_9$ are hydrogen; and ~ is alpha).

Refer to Chart B. Following the procedures of Examples 1, 2, and 3, but replacing the formula-LXXIII γ-lactol starting material of Example 1 with the formula-LXXXII title compound of Preparation 7, there is obtained the formula-XXVII title compound.

EXAMPLE 16

(15S)-15-Methyl-5-oxa-PGF$_{1\alpha}$, Methyl Ester (Formula XXVII: C$_g$H$_{2g}$ is trimethylene; Q$_1$ is

R$_1$ is methyl; R$_2$, R$_3$, R$_4$, R$_5$, R$_8$, and R$_9$ are hydrogen; and ~ is alpha) and (15R)-15-Methyl-5-oxa-PGF$_{1\alpha}$, Methyl Ester (Formula XXVII: Q$_1$ is CH$_3$ OH).

a. Refer to Chart B. Following the procedures of Examples 1, 2, and 3, but replacing the formula-LXXIII γ-lactol starting material of Example 1 with the formula-LXXXVII title compound Preparation 8, there are obtained the formula-XXVII title compounds as a mixture of the 15R and 15S isomers.

b. Alternately, the formula-LXXXVI γ-lactone bis(-tetrahydropyranyl ether) is transformed directly to the corresponding formula-LXXIV compound as follows. The formula-LXXXVI 5α-hydroxy-2β[(3RS)-3-methyl-3-[(tetrahydropyran-2-yl)oxy]-trans-1-octenyl]-3α-[(tetrahydropyran-2-yl)oxy]-cyclopentane-1α-acetic acid, γ-lactone (25.9 g.) in 150 ml. of diethyl ether is added dropwise over a 20 min. period to a stirred slurry of lithium aluminum hydride (3.0 g.) in 500 ml. of ether. The mixture is stirred at about 25° C. for 1.5 hr. and cooled to 0° C. There is then added with caution 4.5 ml. of water in 20 ml. of tetrahydrofuran, then 4.5 ml. of 15% aqueous sodium hydroxide, and finally 5.0 ml. of water. The mixture is filtered through magnesium sulfate, and the filtrate concentrated under reduced pressure to the formula-LXXIV compound, 25.7 g., having NMR peaks at 5.40–5.63, 4.70, 1.30, and 1.23 δ, and R$_f$ 0.35 (TLC on silica gel in ethyl acetate).

c. There is next prepared the formula-LXXV (15RS)-15-methyl-5-oxa-PGF$_{1\alpha}$, methyl ester, 11,15-bis(tetrahydropyranyl ether). To a solution of the product of step b (25.7 g.) in 100 ml. of dry tetrahydrofuran at −15° C. is added, with stirring, 29.6 ml. of 1.6 M. n-butyllithium in hexane. The mixture is stirred for 5 min. and there is added 100 ml. of hexamethylphosphoramide followed by 15 ml. of trimethyl ortho-4-bromobutyrate. The mixture is stirred at about 25° C. for 20 hr. and shaken with a mixture of 600 ml. of ether and 600 ml. of water. The organic phase is washed with brine, dried, and concentrated under reduced pressure. The residue is taken up in 250 ml. of methanol at 0° C. and treated with 50 ml. of cold water containing 10 drops of concentrated hydrochloric acid. The mixture is stirred at 0° C. for 5 min. and shaken with a mixture of 250 ml. of ether, 250 ml. of dichloromethane, and 600 ml. of brine. The organic phase is washed with brine, dried, and concentrated under reduced pressure. The residue is subjected to silica gel chromatography, to yield the formula-LXXV product, 12.9 g., having NMR peaks at 5.37–5.61, 4.69, 3.67, 3.45, 1.22 and 1.3 δ, and R$_f$ 0.50 (TLC on silica gel in 50% ethyl acetate in Skellysolve B).

d. Finally, the formula-XXVII title compounds are obtained as follows. A mixture of the product of step c (8.0 g.), 100 ml. of acetic acid, and 50 ml. of water is stirred at 40° C. for 4 hr. The mixture is shaken with 400 ml. of cold ethyl acetate and a mixture of 100 ml. of 50% aqueous sodium hydroxide and 400 ml. of ice and water. The organic layer is washed with brine, dried, and concentrated under reduced pressure. The residue is subjected to silica gel chromatography to separate the 15R and 15S isomers, using 600 g. of silica gel, and eluting with 5 l. of acetone-dichloromethane (1:1) and then with one l. of acetone. The first liter of eluant is discarded, and fractions 100 ml. in size are then collected. Fractions 5–7 yield the 15R isomer, 0.5 g. having NMR peaks at 5.43–5.64, 3.68, 3.48, and 1.27 δ; R$_f$ 0.42 (TLC on silica gel in acetone-dichloromethane (1:1); and mass spectral peaks at 602.3880, 587, 531, 512, 497, 459, 422, 332, 217 and 213. Fractions 28–40 yield the 15S isomer, 0.3 g., having NMR peaks at 5.41-5.57, 3.68, 3.48, and 1.27 δ; R$_f$ 0.34 (TLC on silica gel in acetone-dichloromethane (1:1)); and mass spectral peaks at 602.3885, 587, 531, 512, 497, 459 and 441.

EXAMPLE 17

(15S)-15-Methyl-5-oxa-PGE$_1$, Methyl Ester (Formula XXI: C$_g$H$_{2g}$ is trimethylene; Q$_1$ is

R$_1$ is methyl; and R$_2$, R$_3$, R$_4$, R$_5$, R$_8$, and R$_9$ are hydrogen) and (15R)-15-Methyl-5-oxa-PGE$_1$, Methyl Ester (Formula XXI: Q$_1$ is

a. There is first prepared (15S)-15-methyl-5-oxa-PGF$_{1\alpha}$, methyl ester, 11-trimethylsilyl ether. The formula-XXVII 15S isomer of Example 16 (0.4 g.) in 20 ml. of acetone at −45° C. is treated, with stirring, with 2.0 ml. of N-trimethylsilyldiethylamine. The mixture is stirred at about −43° C. for 2.5 hr. and is then diluted with 150 ml. of ether precooled to −78° C. The solution is washed immediately with aqueous sodium bicarbonate and brine, then dried and concentrated under reduced pressure to yield the 11-trimethylsilyl ether, 0.5 g., having R$_f$ 0.35 (TLC on silica gel in 50% ethyl acetate in hexane).

b. The above 11-trimethylsilyl ether is oxidized with Collins reagent prepared in 30 ml. of dichloromethane from 1.36 ml. of pyridine and 0.835 g. of chromium trioxide previously cooled to about 10° C. The mixture is stirred at 25° C. for 30 min. and filtered. The filtrate is concentrated to give the (15S)-15-methyl-5-oxa-PGE$_1$, methyl ester, 11-trimethylsilyl ether, 0.41 g., having R$_f$ 0.53 (TLC on silica gel in hexane). Hydrolysis of this material in 20 ml. of methanol, 10 ml. of water, and 1 ml. of acetic acid at 0°–25° C., followed by washing with aqueous sodium bicarbonate and brine, drying and concentrating, yields the 15S title product, 0.29 g. After silica gel chromatography there is obtained 0.12 g. of (15S)-15-methyl-5-oxa-PGE$_1$, methyl ester, having NMR peaks at 5.60–5.73, 3.68, 3.40, and 1.31 δ; R$_f$ 0.33 (TLC on silica gel in ethyl acetate); and mass spectral peaks at 528.3285, 513, 457, 438, 384, 367, 348, and 101.

c. Following the procedures of steps a and b above but employing the 15 R isomer of the formula-XXVII compound of Example 16 (0.49 g.), there are obtained the corresponding 11-trimethylsilyl PGE$_{1\alpha}$ and PGE$_1$ compounds and finally (15R)-15-methyl-5-oxa-PGE$_1$, methyl ester, 0.15 g., having NMR peaks at 5.60–5.72, 3.68, 3.40, and 1.30 δ; R$_f$ 0.41 (TLC on silica gel in ethyl acetate)); and mass spectral peaks at 528.3338, 513, 457, 438, 423, 367, 348, 313, 249 and 101.

EXAMPLE 18

5-Oxa-13,14-dihydro-PGF$_{1\alpha}$ Methyl Ester (Formula XXIX: C$_g$H$_{2g}$ is trimethylene; Q$_1$ is

R$_1$ is methyl; R$_2$, R$_3$, R$_4$, R$_5$, R$_8$, and R$_9$ are hydrogen; and ∼ is alpha).

A solution of 5-oxa-PGF$_{1\alpha}$ methyl ester (Example 3, 100 mg.) in 10 ml. of ethyl acetate is shaken with hydrogen at about one atmosphere pressure at 25° C. in the presence of 5% palladium on charcoal (15 mg.). The hydrogenation is stopped when one equivalent of hydrogen is absorbed, and the catalyst is removed by filtration. The filtrate is concentrated, and the residue is subjected to silica gel chromatogaphy to obtain the title compound.

EXAMPLE 19

5-Oxa-11-deoxy-PGF$_{1\alpha}$, Methyl Ester (Formula XXX: C$_g$H$_{2g}$ is trimethylene; Q$_1$ is

$R_1$ is methyl; $R_2$, $R_3$, $R_4$, $R_5$, $R_8$, and $R_9$ are hydrogen; and ~ is alpha).

Following the procedures of Examples 1, 2, and 3, but replacing the formula-LXXIII γ-lactol starting material of Example 1 with the formula-CVI title compound of Preparation 9, there is obtained the formula-XXX title compound.

EXAMPLE 20

5-Oxa-11-deoxy-17,18-dehydro-PGF$_{1\alpha}$, Methyl Ester (Formula XXXI: $Q_1$ is

$R_1$ is methyl; $R_2$, $R_3$, $R_4$, and $R_5$ are hydrogen; and ~ is alpha).

Following the procedures of Examples 1, 2, and 3, but replacing the formula-LXXIII γ-lactol starting material of Example 1 with the formula-CVII title compound of Preparation 10, there is obtained the formula-XXX title compound.

EXAMPLE 21

5-Oxa PGE$_1$-type Compounds

Following the procedure of Example 6, but replacing the 5-oxa-PGF$_{1\alpha}$, methyl ester, 11,15-bis(tetrahydropyranyl ether) of that example with the appropriate 5-oxa PGF$_{1\alpha}$-type compound available from the examples herein, there are obtained, for example, the following compounds:

- 5-oxa-17,18-dehydro-PGE$_1$, methyl ester (Formula XXIV)
- 5-oxa-11-deoxy-PGE$_1$, methyl ester (Formula XXIV)
- 5-oxa-11-deoxy-17,18-dehydro-PGE$_1$, methyl ester (Formula XXV).

EXAMPLE 22

5-Oxa PGF$_{1\beta}$-type Compounds

Following the procedures of Example 7, but replacing the 5-oxa-PGE$_1$, methyl ester of that example with the appropriate 5-oxa-PGE$_1$-type compound available from the examples herein, there are obtained, for example, the following compounds:

- 16,16-dimethyl-5-oxa-PGF$_{1\beta}$, methyl ester (Formula XXVII)
- 5-oxa-17,18-dehydro-PFG$_{1\beta}$, methyl ester (Formula XXXVIII)
- 5-oxa-PGF$_{1\beta}$, 15-methyl ether, methyl ester (Formula XXVII)
- 5-oxa-11-deoxy-PGF$_{1\beta}$, methyl ester (Formula XXX)
- 5-oxa-11-deoxy-17,18-dehydro-PGF$_{1\beta}$, methyl ester (Formula XXXI).

EXAMPLE 23

5-Oxa PGA$_1$-type Compounds

Following the procedure of Example 8, but replacing the 5-oxa-PGE$_1$, methyl ester of that example with the appropriate 5-oxa PGE$_1$-type compound available from the examples herein, there are obtained, for example, the following compounds:

- 16,16-dimethyl-5-oxa-PGA$_1$, methyl ester (Formula XXXIII)
- 5-oxa-17,18-dehydro-PGA$_1$, methyl ester (Formula XXXIV)
- 15(S)-15-methyl-5-oxa-PGA$_1$, methyl ester (Formula XXXIII)
- 15(R)-15-methyl-5-oxa-PGA$_1$, methyl ester (Formula XXXIII)
- 5-oxa-13,14-dihydro-PGA$_1$, methyl ester (Formula XXXV).

EXAMPLE 24

5-Oxa PGB$_1$-type Compounds

Following the procedure of Example 9, but replacing the 5-oxa-PGE$_1$, methyl ester of that example with the appropriate 5-oxa PGE$_1$-type compound available from the examples herein, there are obtained, for example, the following compounds:

- 16,16-dimethyl-5-oxa-PGB$_1$ (Formula XXXVI)
- 5-oxa-17,18-dehydro-PGB$_1$ (Formula XXXVII)
- 15(S)-15-methyl-5-oxa-PGB$_1$ (Formula XXXVI)
- 15(R)-15-methyl-5-oxa-PGB$_1$ (Formula XXXVI)
- 5-oxa-13,14-dihydro-PGB$_1$ (Formula XXXVIII).

EXAMPLE 25

5-Oxa-13,14-dihydro PG$_1$-type Compounds

Following the procedure of Example 18, the various 5-oxa PG$_1$-type compounds available from the examples herein, in either their acid or ester forms, are reduced to the corresponding 5-oxa-13,14-dihydro PG$_1$-type compounds. Thus, from the following 5-oxa PG$_1$-type compounds and their methyl esters:

- 5-oxa-PGE$_1$
- 5-oxa-PGF$_{1\beta}$
- 5-oxa-PGB$_1$
- 16,16-dimethyl-5-oxa-PGF$_{1\alpha}$
- 15(S)-15-methyl-5-oxa-PGF$_{1\alpha}$
- 15(R)-15-methyl-5-oxa-PGF$_{1\alpha}$
- 15(S)-15-methyl-5-oxa-PGE$_1$
- 5-oxa-11-deoxy-PGF$_{1\alpha}$
- 5-oxa-11-deoxy-PGE$_1$
- 5-oxa-11-deoxy-PGF$_{1\beta}$
- 5-oxa-11-deoxy-PGB$_1$ there are obtained the following corresponding 5-oxa-13,14-dihydro PG$_1$-type compounds and their methyl esters:

- 5-oxa-13,14-dihydro-PGE$_1$
- 5-oxa-13,14-dihydro-PGF$_{1\beta}$
- 5-oxa-13,14-dihydro-PGB$_1$
- 16,16-dimethyl-5-oxa-13,14-dihydro-PGF$_{1\alpha}$
- 15(S)-15-methyl-5-oxa-13,14-dihydro-PGF$_{1\alpha}$
- 15(R)-15-methyl-5-oxa-13,14-dihydro-PGF$_{1\alpha}$
- 15(S)-15-methyl-5-oxa-13,14-dihydro-PGE$_1$
- 5-oxa-11-deoxy-13,14-dihydro-PGF$_{1\alpha}$
- 5-oxa-11-deoxy-13,14-dihydro-PGE$_1$
- 5-oxa-11-deoxy-13,14-dihydro-PGF$_{1\beta}$
- 5-oxa-11-deoxy-13,14-dihydro-PGB$_1$.

EXAMPLE 25A

5-Oxa-13,14-dihydro-PGA$_1$, Methyl Ester (Formula XXXV: $Q_1$ is

$C_gH_{2g}$ is trimethylene; $R_1$ is methyl; and $R_2$, $R_3$, $R_4$, $R_5$, $R_8$, and $R_9$ are hydrogen).

For the reduction of PGA$_1$ compounds to 13,14-dihydro-PGA$_1$ compounds diimide is used. See van Tamelen et al., J. Am. Chem. Soc. 83, 3726 (1961) and Fieser et al., "Topics in Organic Chemistry", Reinhold Publishing Corp., New York, pp. 432–434 (1963). A suspension of disodium azodiformate (50 mg.) in 5 ml. of absolute ethanol is added to a stirred solution of 5-oxa-PGA$_1$, methyl ester (Example 8, 50 mg.) in 10 ml. of absolute ethanol under nitrogen at 25° C. The mixture is made acid with glacial acetic acid, and then is stirred under nitrogen at 25° C. for 8 hr. The resulting mixture is concentrated under reduced pressure, and the residue is mixed with a mixture of diethyl ether and water (1:1). The diethyl ether layer is separated, dried, and concentrated to give the title compound.

EXAMPLE 26

5-Oxa-PGB$_1$ Methyl Ester (Formula XXXVI: C$_g$H$_{2g}$ is trimethylene; Q$_1$ is

R$_1$ is methyl; and R$_2$, R$_3$, R$_4$, R$_5$, R$_8$, and R$_9$ are hydrogen).

A solution of diazomethane (about 50% excess) in diethyl ether (25 ml.) is added to a solution of 5-oxa-PGB$_1$ (Example 9, 50 mg.) in 25 ml. of a mixture of methanol and diethyl ether(1:1). The mixture is allowed to stand at 25° C. for 5 min. Then the mixture is concentrated to give the title compound.

Following the procedure of Example 26, each of the other specific 5-oxa PGB-type, PGA-type, PGE-type, and PGF-type free acids identified herein is converted to the corresponding methyl ester.

Also following the procedure of Example 26, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 5-oxa-PGB$_1$. In the same manner, each of the other specific 5-oxa PGB-type, PGA-type, PGE-type, and PGF-type free acids identified herein is converted to the corresponding ethyl, butyl, 2-ethylhexyl, and cyclohexyl esters.

EXAMPLE 27

5-Oxa-PGE$_1$ Methyl Ester Diacetate

Acetic anhydride (5 ml.) and pyridine (5 ml.) are mixed with 5-oxa-PGE$_1$ methyl ester (Example 6, 20 mg.), and the mixture is allowed to stand at 0°–25° C. for 5–15 hr. The mixture is then cooled to 0° C., diluted with 50 ml. of water, and acidified with 5% hydrochloric acid to pH 1. That mixture is extracted with ethyl acetate and the extract is washed successively with 5% hydrochloric acid, 5% aqueous sodium bicarbonate solution, water, and brine, dried and concentrated to give the title compound.

Following the procedure of Example 27 but replacing the acetic anhydride with propionic anhydride, isobutyric anhydride, and hexanoic acid anhydride, there are obtained the corresponding dipropionate, diisobutyrate and dihexanoate derivatives of 5-oxa-PGE$_1$ methyl ester.

Also following the procedure of Example 27, but replacing the 5-oxa-PGE$_1$ compound with 5-oxa-PGF$_{1\alpha}$ and -PGF$_{1\beta}$, there are obtained the corresponding triacetate derivatives of the 5-oxa-PGF compounds.

Also following the procedure of Example 27, each of the 5-oxa PGE-type, PGF-type, PGA-type, and PGB-type esters and free acids defined above is transformed to the corresponding acetates, propionates, isobutyrates, and hexanoates, the PGE-type and the 11-deoxy-PGF-type derivatives being dialkanoates, the PGF-type derivatives being trialkanoates, and the PGA-type, the PGB-type, and the 11-deoxy-PGE-type derivatives being monoalkanoates.

EXAMPLE 28

5-Oxa-PGE$_1$ from 5-Oxa-PGE$_1$, Methyl Ester.

There is first prepared an esterase composition from Plexaura homomalla, for which see W. P. Schneider et al., J. Am. Chem. Soc. 94, 2122 (1972). Freshly harvested colony pieces of Plexaura homomalla (Esper), 1792, forma S (10 kg.), are chopped into pieces less than 3 mm. in their longest dimension, and then covered with about three volumes (20 l.) of acetone. The mixture is stirred at about 25° C. for about one hour. The solids are separated by filtration, washed with 1–2 liters of acetone, air dried, and finally stored at about −20° C. as a coarse enzymatic powder.

A suspension of the above powder (2.5 g.) in 25 ml. of water is combined with a solution of 5-oxa-PGE$_1$, methyl ester (Example 6, 0.5 g.) in about 0.8 ml. of ethanol previously acidified to pH 6 with phosphoric acid. The mixture is stirred at about 25° C. for 24 hr. Then, 50 ml. of acetone is added, the mixture is stirred briefly and filtered, and the filtrate is concentrated under reduced pressure. The aqueous residue is acidified to pH 3.5 with citric acid and extracted with dichloromethane. The combined extracts are concentrated under reduced pressure to the title compound.

Following the procedure of Example 28, but replacing the methyl ester of that example with the methyl esters of the 5-oxa PG compounds identified herein there are obtained the corresponding free acids, for example 5-oxa-PGF$_{1\alpha}$
5-oxa-PGF$_{1\beta}$
5-oxa-PGA$_1$
5-oxa-16,16-dimethyl-PGF$_{1\alpha}$
5-oxa-16,16-dimethyl-PGE$_1$
5-oxa-17,18-dehydro-PGF$_{1\alpha}$
5-oxa-PGF$_{1\alpha}$, 15-methyl ether
(15S)-15-methyl-5-oxa-PGF$_{1\alpha}$
5-oxa-13,14-dihydro-PGF$_{1\alpha}$
5-oxa-11-deoxy-PGF$_{1\alpha}$ and
5-oxa-11-deoxy-17,18-dehydro-PGF$_{1\alpha}$.

EXAMPLE 29

5-Oxa-PGE$_1$ Sodium Salt

A solution of 5-oxa-PGE$_1$ (Example 28, 100 mg.) in 50 ml. of a water-ethanol mixture (1:1) is cooled to 5° C. and neutralized with an equivalent amount of 0.1 N. aqueous sodium hydroxide solution. The solution is concentrated to give the title compound.

Following the procedure of Example 29, but using potassium hydroxide, calcium hydroxide, tetramethylammonium hydroxide, and benzyltrimethylammonium hydroxide in place of sodium hydroxide, there are obtained the corresponding salts of 5-oxa-PGE$_1$.

Also following the procedure of Example 29 each of the 5-oxa PGE-type, PGF-type, PGA-type, and PGB-type acids identified herein is transformed to the sodium, potassium, calcium, tetramethylammonium, and benzyltrimethylammonium salts.

EXAMPLE 30

2-{2β-[(3S)-5-Phenyl-3-[(tetrahydropyran-2-yl)-oxy]-trans-1-pentenyl]-5α-hydroxy-3α-[(tetrahydropyran-2-yl)oxy]-1α-cyclopentyl}-ethanol (Formula LXXIV: $Q_3$ is

$R_{13}$ is THP, and $R_{14}$ is

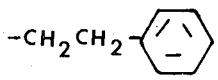  ).

Refer to Chart B. A mixture of the formula-LXXII 2β-[(3S)-5-phenyl-3-[(tetrahydropyran-2-yl)oxy]-trans-1-pentenyl]-5α-hydroxy-3α-[(tetrahydropyran-2-yl)oxy]-1α-cyclopentaneacetaldehyde, γ-lactol (Preparation 11, 7.5 g.) and 60 ml. of 95% ethanol is treated at 0° C., while stirring, with a solution of sodium borohydride (0.75 g.) in 12 ml. of water. The mixture is stirred at 0° C. for 10 min. and is then shaken with 200 ml. of ethyl acetate, 20 ml. of water, and 150 ml. of brine. The organic layer is washed with brine, dried and concentrated under reduced pressure. The residue is subjected to silica gel chromatography, eluting with 75–100% ethyl acetate in Skellysolve B, to yield the title compound, 4.8 g., having $R_f$ 0.40 (TLC on silica gel plate in ethyl acetate) and NMR peaks at 7.21, 5.38–5.68, and 4.69 δ.

EXAMPLE 31

5-Oxa-17-phenyl-18,19,20-trinor-PGF$_{1\alpha}$, Methyl Ester, 11,15-Bis(tetrahydropyranyl ether) (Formula LXXV: $Q_3$ is

$R_2$, $R_3$, $R_4$, and $R_5$ are hydrogen; $R_{13}$ is THP; and $R_{14}$ is

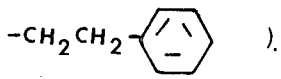 ).

Refer to Chart B. A solution of the formula-LXXIV 2-{2β-[(3S)-5-phenyl-3-[(tetrahydropyran-2-yl)oxy]-trans-1-pentenyl]-5α-hydroxy-3α-[(tetrahydropyran-2-yl)oxy]-1α-cyclopentyl}ethanol (Example 30, 4.4 g.) in 20 ml. of tetrahydrofuran is treated at −15° C., while stirring, with 5.8 ml. of 1.6 M n-butyllithium over a 2-min. period. The mixture is stirred at 0° C. for 5 min. and then treated with 20 ml. of hexamethylphosphoramide and 4 ml. of trimethyl ortho-4-bromobutyrate (Preparation 1). The mixture is stirred at about 25° C. for 6 hr. and is then shaken with diethyl ether and water. The organic phase is washed with brine, dried, and concentrated under reduced pressure.

The residue, containing the ortho ester, is dissolved in 60 ml. of methanol at 0° C., and treated with 15 ml. of cold water containing 2 drops of concentrated hydrochloric acid. The mixture is stirred at 0° C. for 5 min. and shaken with 200 ml. of diethyl ether, 50 ml. of dichloromethane, and 200 ml. of brine. The organic phase is washed with brine, dried and concentrated under reduced pressure. The residue is subjected to silica gel chromatography, eluting with 50–75% ethyl acetate in Skellysolve B, to yield the title compound, 2.25 g., having $R_f$ 0.56 (TLC on silica gel plate in 75% ethyl acetate in Skellysolve B), and NMR peaks at 7.2, 5.37–5.69, 4.70, and 3.61 δ.

EXAMPLE 32

5-Oxa-17-phenyl-18,19,20-trinor-PGF$_{1\alpha}$, Methyl Ester (Formula XLVII: $C_jH_{2j}$ is methylene; $Q_1$ is

$R_1$ is methyl; $R_2$, $R_3$, $R_4$, $R_5$, $R_8$, and $R_9$ are hydrogen; s is zero; and ~ is alpha).

Refer to Chart B. A mixture of the formula-LXXV 5-oxa-17-phenyl-18,19,20-trinor-PGF$_{1\alpha}$, methyl ester, 11,15-bis(tetrahydropyranyl ether) (Example 31, 1.2 g.) in 40 ml. of acetic acid, 20 ml. of water, and 6 ml. of tetrahydrofuran is stirred at 40° C. for 4 hr. The mixture is diluted with ethyl acetate and the organic phase is washed with cold dilute sodium hydroxide solution, water, and brine, dried and concentrated under reduced pressure. The residue is subjected to silica gel chromatography to yield the title compound, 0.45 g., having $R_f$ 0.29 (TLC on silica gel plate in 5% ethanol in ethyl acetate) and NMR peaks at 7.21, 5.40-5.68, 3.63, and 3.33-3.52 δ.

EXAMPLE 33

5-Oxa Phenyl-substituted PGF$_{1\alpha}$-type Compounds within the scope of Formula XLVII.

Following the procedures of Examples 30–32, but replacing the Preparation-11 γ-lactol starting material of Example 30 with each of the appropriate formula-LXXII γ-lactols identified in and following Preparation 11, there are obtained the corresponding 5-oxa phenyl-substituted PGF$_{1\alpha}$-type compounds, both optically active and racemic, wherein $Q_1$ is either

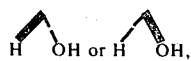

including their methyl esters for example:
5-oxa-16-phenyl-17,18,19,20-tetranor-PGF$_{1\alpha}$
5-oxa-16(p-chlorophenyl)-17,18,19,20-tetranor-PGF$_{1\alpha}$
5-oxa-16-(o,p-dichlorophenyl)-18,19,20-trinor-PGF$_{1\alpha}$
5-oxa-16-fluoro-16-(p-tolyl)-17,18,19,20-tetranor-PGF$_{1\alpha}$
5-oxa-16-butyl-16-phenyl-17,18,19,20-tetranor-PGF$_{1\alpha}$
5-oxa-17-(p-chlorophenyl)-18,19,20-trinor-PGF$_{1\alpha}$
5-oxa-17-(α,α,α-trifluoro-p-tolyl)-18,19,20-trinor-PGF$_{1\alpha}$
5-oxa-16-ethyl-17-(m-methoxyphenyl)-18,19,20-trinor-PGF$_{1\alpha}$
5-oxa-16,16-difluoro-17-phenyl-18,19,20-trinor-PGF$_{1\alpha}$
5-oxa-18-phenyl-19,20-dinor-PGF$_{1\alpha}$
5-oxa-18-(p-chlorophenyl)-19,20-dinor-PGF$_{1\alpha}$
5-oxa-18-(p-tolyl)-19,20-dinor-PGF$_{1\alpha}$ 5-oxa-18-(2-chloro-4-tolyl)-19,20-dinor-PGF$_{1\alpha}$
5-oxa-16-methyl-18-(2,4-xylyl)-19,20-dinor-PGF$_{1\alpha}$
5-oxa-19-phenyl-20-nor-PGF$_{1\alpha}$
5-oxa-16,16-dimethyl-19-phenyl-20-nor-PGF$_{1\alpha}$
5-oxa-16-heptyl-18-phenyl-19,20-dinor-PGF$_{1\alpha}$
5-oxa-20-phenyl-PGF$_{1\alpha}$
5-oxa-20-benzyl-PGF$_{1\alpha}$ and
5-oxa-17-phenyl-17-propyl-20-ethyl-PGF$_{1\alpha}$.

EXAMPLE 34

5-Oxa-17-phenyl-18,19,20-trinor-PGE$_1$, Methyl Ester (Formula XXXIX: $C_jH_{2j}$ is methylene, $Q_1$ is

$R_1$ is methyl; $R_2$, $R_3$, $R_4$, $R_5$, $R_8$, and $R_9$ are hydrogen; and s is zero).

Refer to Chart C. There is first prepared the intermediate 5-oxa-17-phenyl-18,19,20-trinor-PGE$_1$, methyl ester, 11,15-bis(tetrahydropyranyl ether). A solution of the formula-LXXV 5-oxa-17-phenyl-18,19,20-trinor-PGF$_{1\alpha}$, methyl ester, 11,15-bis(tetrahydropyranyl ether) (Example 31, 1.05 g.) is oxidized with the Jones reagent to yield the desired intermediate 0.9 g., having $R_f$ 0.23 (TLC on silica gel plate in 30% ethyl acetate in Skellysolve B).

The above intermediate is then hydrolyzed following the procedure of Example 32 and subjected to silica gel chromatography to obtain the title compound, 0.45 g. having $R_f$ 0.48 (TLC on silica gel plate in 5% ethanol in ethyl acetate) and NMR peaks at 7.22, 5.55–5.70, 3.61, and 3.24–3.48 δ.

EXAMPLE 35

5-Oxa-17-phenyl-18,19,20-trinor-PGF$_{1\alpha}$, Methyl Exter (Formula XLVII: $C_jH_{2j}$ is methylene; $Q_1$ is

$R_1$ is methyl; $R_2$, $R_3$, $R_4$, $R_5$, $R_8$, and $R_9$ are hydrogen, s is zero; and ~ is alpha) and 5-Oxa-17-phenyl-18,19,20-trinor-PGF$_{1\beta}$, Methyl Ester (Formula XLVII: ~ is beta).

Refer to Chart C. The formula-XXXIX 5-oxa-17-phenyl-18,19,20-trinor-PGE$_1$, methyl ester (Example 34, 0.2 g.) is treated in 6 ml. of methanol at 0°C., while stirring, with a solution of 50 mg. of sodium borohydride in 0.5 ml. of water. The mixture is stirred at 0°C. for 10 min. and then diluted with 100 ml. of ethyl acetate. The organic phase is washed with brine, dried, and concentrated under reduced pressure. The residue is subjected to silica gel chromatography to separate the title compounds thus obtained.

EXAMPLE 36

5-Oxa-16-phenoxy-17,18,19,20-tetranor-PGF$_{1\alpha}$ Methyl Ester (Formula LI: $Q_1$ is

$R_1$ is methyl; $R_2$, $R_3$, $R_4$, $R_5$, $R_8$, and $R_9$ are hydrogen; s is zero; and ~ is alpha).

Following the procedures of Examples 30, 31, and 32, but replacing the formula-LXXII γ-lactol starting material of Example 30 with the formula-LXXII title compound of Preparation 12, there is obtained the formula-LI title compound.

EXAMPLE 37

5-Oxa 16-Phenoxy PGF$_{1\alpha}$-type Compounds within the scope of Formula LI

Following the procedures of Examples 30, 31, and 32, but replacing the Preparation-12 γ-lactol starting material of Example 30 with each of the appropriate formula-LXXII γ-lactols identified in and following Preparation 12, there are obtained the corresponding 5-oxa 16-phenoxy PGF$_{1\alpha}$-type compounds, both optically active and racemic, wherein $Q_1$ is either

including their methyl esters, for example:
5-oxa-16-(p-fluorophenoxy)-17,18,19,20-tetranor-PGF$_{1\alpha}$
5-oxa-16-phenoxy-18,19,20-trinor-PGF$_{1\alpha}$
5-oxa-16-methyl-16-phenoxy-18,19,20-trinor-PGF$_{1\alpha}$
5-oxa-16-phenoxy-19,20-dinor-PGF$_{1\alpha}$
5-oxa-16-ethyl-16-phenoxy-19,20-dinor-PGF$_{1\alpha}$
5-oxa-16-methyl-16-phenoxy-19,20-dinor-PGF$_{1\alpha}$
5-oxa-16-(p-tolyloxy)-17,18,19,20-tetranor-PGF$_{1\alpha}$
5-oxa-16-(p-fluorophenoxy)-18,19,20-trinor-PGF$_{1\alpha}$
5-oxa-16-methyl-16-(o,p-dichlorophenoxy)-18,19,20-trinor-PGF$_{1\alpha}$
5-oxa-16-(α,α,α-trifluoro-p-tolyloxy)-19,20-dinor-PGF$_{1\alpha}$
5-oxa-16-methyl-16-(m-methoxyphenoxy)-19,20-dinor-PGF$_{1\alpha}$
and 5-oxa-16-phenoxy-PGF$_{1\alpha}$.

EXAMPLE 38

5-Oxa-11-deoxy-17-phenyl-18,19,20-trinor-PGF$_{1\alpha}$ Methyl Ester (Formula XLIX: $Q_1$ is

$R_1$ is methyl; $R_2$, $R_3$, $R_4$, $R_5$, $R_8$, and $R_9$ are hydrogen; s is zero; and ~ is alpha).

Following the procedures of Examples 30, 31, and 32, but replacing the formula-LXXII γ-lactol starting material of Example 30 with the formula-CVI title compound of Preparation 13, there is obtained the title compound.

EXAMPLE 39

5-Oxa-11-deoxy-16-phenoxy-17,18,19,20-tetranor-PGF$_{1\alpha}$, Methyl Ester (Formula LII: $Q_1$ is

$R_1$ is methyl; $R_2$, $R_3$, $R_4$, $R_5$, $R_8$, and $R_9$ are hydrogen; s is zero; and ~ is alpha).

Following the procedures of Examples 30, 31, and 32, but replacing the formula-LXXII γ-lactol starting material of Example 30 with the formula-CVI title compound of Preparation 14, there is obtained the title compound.

EXAMPLE 40

5-Oxa 17-Phenyl and 16-Phenoxy $PGE_1$-type Compounds

Following the procedures of Example 34 but replacing the 5-oxa-17-phenyl-18,19,20-trinor-$PGF_{1\alpha}$, methyl ester, 11,15-bis(tetrahydropyranyl ether) of that example with the appropriate corresponding compound available from the examples herein, there are obtained, for example, the following compounds:
 5-oxa-16-phenoxy-17,18,19,20-tetranor-$PGE_1$, methyl ester (Formula XLIII)
 5-oxa-11-deoxy-17-phenyl-18,19,20-trinor-$PGE_1$, methyl ester (Formula XLI)
 5-oxa-11-deoxy-16-phenoxy-17,18,19,20-tetranor-$PGE_1$, methyl ester (Formula XLV).

EXAMPLE 41

5-Oxa 17-Phenyl and 16-Phenoxy $PGF_{1\beta}$-type Compounds

Following the procedure of Example 35, but replacing the 5-oxa $PGE_1$-type compound of that example with the appropriate corresponding compound available from the examples herein, there are obtained, for example, the following compounds:
 5-oxa-16-phenoxy-17,18,19,20-tetranor-$PGE_{1\beta}$ (Formula LI)
 5-oxa-11-deoxy-17-phenyl-18,19,20-trinor-$PGF_{1\beta}$ (Formula XLIX)
 5-oxa-11-deoxy-16-phenoxy-17,18,19,20-tetranor-$PGF_{1\beta}$ (Formula LIII).

EXAMPLE 42

5-Oxa-13,14-dihydro-17-phenyl-18,19,20-trinor-$PGF_{1\alpha}$, Methyl Ester (Formula XLVIII: $C_jH_{2j}$ is trimethylene, $Q_1$ is

$R_1$ is methyl, $R_2$, $R_3$, $R_4$, $R_5$, $R_8$, and $R_9$ are hydrogen; s is zero; and ~ is alpha).

A solution of 5-oxa-17-phenyl-18,19,20-trinor-$PGF_{1\alpha}$, methyl ester, (Example 32, 100 mg.) in 10 ml. of ethyl acetate is shaken with hydrogen at about one atmosphere pressure at 25° C. in the presence of 5% palladium on charcoal (15 mg.). The hydrogenation is stopped when one equivalent of hydrogen is absorbed and the catalyst is removed by filtration. The filtrate is concentrated, and the residue is subjected to silica gel chromatography to obtain the title compound.

EXAMPLE 43

5-Oxa-13,14-dihydro 17-Phenyl and 16-Phenoxy $PG_1$-type Compounds

Following the procedure of Example 42, the various 5-oxa 17-phenyl or 16-phenoxy $PG_1$-type compounds available from the examples herein, in either their acid or ester forms, are reduced to the corresponding 5-oxa-13,14-dihydro $PG_1$-type compounds. Thus, from the following compounds and their methyl esters:
 5-oxa-17-phenyl-18,19,20-trinor-$PGE_1$
 5-oxa-17-phenyl-18,19,20-trinor-$PGF_{1\beta}$
 5-oxa-17-phenyl-18,19,20-trinor-$PGB_1$
 5-oxa-16-phenoxy-17,18,19,20-tetranor-$PGF_{1\alpha}$
 5-oxa-16-phenoxy-17,18,19,20-tetranor-$PGE_1$
 5-oxa-16-phenoxy-17,18,19,20-tetranor-$PGF_{1\beta}$
 5-oxa-16-phenoxy-17,18,19,20-tetranor-$PGB_1$
 5-oxa-11-deoxy-17-phenyl-18,19,20-trinor-$PGF_{1\alpha}$
 5-oxa-11-deoxy-17-phenyl-18,19,20-trinor-$PGE_1$
 5-oxa-11-deoxy-17-phenyl-18,19,20-trinor-$PGF_{1\beta}$
 5-oxa-11-deoxy-17-phenyl-18,19,20-trinor-$PGB_1$
 5-oxa-11-deoxy-16-phenoxy-17,18,19,20-tetranor-$PGF_{1\alpha}$
 5-oxa-11-deoxy-16-phenoxy-17,18,19,20-tetranor-$PGE_1$
 5-oxa-11-deoxy-16-phenoxy-17,18,19,20-tetranor-$PGF_{1\beta}$
 5-oxa-11-deoxy-16-phenoxy-17,18,19,20-tetranor-$PGB_1$
there are obtained the following corresponding 5-oxa-13,14-dihydro $PG_1$-type compounds and their methyl esters:
 5-oxa-13,14-dihydro-17-phenyl-18,19,20-trinor-$PGE_1$
 5-oxa-13,14-dihydro-17-phenyl-18,19,20-trinor-$PGF_{1\beta}$
 5-oxa-13,14-dihydro-17-phenyl-18,19,20-trinor-$PGB_1$
 5-oxa-13,14-dihydro-16-phenoxy-17,18,19,20-tetranor-$PGF_{1\alpha}$
 5-oxa-13,14-dihydro-16-phenoxy-17,18,19,20-tetranor-$PGE_1$
 5-oxa-13,14-dihydro-16-phenoxy-17,18,19,20-tetranor-$PGF_{1\beta}$
 5-oxa-13,14-dihydro-16-phenoxy-17,18,19,20-tetranor-$PGB_1$
 5-oxa-11-deoxy-13,14,-dihydro-17-phenyl-18,19,20-trinor-$PGF_{1\alpha}$
 5-oxa-11-deoxy-13,14-dihydro-17-phenyl-18,19,20-trinor-$PGE_1$
 5-oxa-11-deoxy-13,14-dihydro-17-phenyl-18,19,20-trinor-$PGF_{1\beta}$
 5-oxa-11-deoxy-13,14-dihydro-17-phenyl-18,19,20-trinor-$PGB_1$
 5-oxa-11-deoxy-13,14-dihydro-16-phenoxy-17,18,19,20-tetranor-$PGF_{1\alpha}$
 5-oxa-11-deoxy-13,14-dihydro-16-phenoxy-17,18,19,20-tetranor-$PGE_1$
 5-oxa-11-deoxy-13,14-dihydro-16-phenoxy-17,18,19,20-tetranor-$PGF_{1\beta}$
 5-oxa-11-deoxy-13,14-dihydro-16-phenoxy-17,18,19,20-tetranor-$PGB_1$.

EXAMPLE 43A

5-Oxa-13,14-dihydro-17-phenyl-18,19,20-trinor-$PGA_1$ (Formula LVI: $Q_1$ is

$C_jH_{2j}$ is methylene; $R_1$, $R_2$, $R_3$, $R_4$, $R_5$, $R_8$, and $R_9$ are hydrogen; and s is zero).

A suspension of disodium azodiformate (50 mg.) in 5 ml. of absolute ethanol is added to a stirred solution of 5-oxa-17-phenyl-18,19,20-trinor-$PGA_1$ (50 mg.) in 10 ml. of absolute ethanol under nitrogen at 25° C. The mixture is made acid with glacial acetic acid, and then is stirred under nitrogen at 25° C. for 8 hr. The resulting mixture is concentrated under reduced pressure, and the residue is mixed with a mixture of diethyl ether and water (1:1). The diethyl ether layer is separated, dried, and concentrated to give the title compound.

Following the procedure of Example 43A, the various 5-oxa substituted phenyl or 16-phenoxy $PGA_1$-type compounds available from the examples herein are reduced to the corresponding 5-oxa-13,14-dihydro $PGA_1$-type compounds, for example 5-oxa-13,14-dihydro-16-phenoxy-17,18,19,20-tetranor-$PGA_1$.

EXAMPLE 44

5-Oxa-17-phenyl-18,19,20-trinor-$PGA_1$, Methyl Ester (Formula LV: $C_jH_{2j}$ is methylene; $Q_1$

$R_1$ is methyl; $R_2$, $R_3$, $R_4$, $R_5$, $R_8$, and $R_9$ are hydrogen; and s is zero).

Refer to Chart H. A solution of 5-oxa-17-phenyl-18,19,20-trinor-$PGE_1$, methyl ester (Example 34, 0.2 g.) in a mixture of glacial acetic acid (9 ml.) and water (1 ml.) is heated under nitrogen at 60° C. for 18 hr. Then, the acetic acid and water are evaporated under reduced pressure, and the residue is subjected to silica gel chromatography to yield the title compound.

EXAMPLE 45

5-Oxa 17-Phenyl and 16-Phenoxy $PGA_1$-type Compounds

Following the procedure of Example 44 but replacing the 5-oxa $PGE_1$-type compound of that example with the appropriate corresponding compound available from the examples herein, there are obtained, for example, the following compounds:

5-oxa-16-phenoxy-17,18,19,20-tetranor-$PGA_1$, methyl ester (Formula LVII)

5-oxa-13,14-dihydro-17-phenyl-18,19,20-trinor-$PGA_1$, methyl ester (Formula LVI)

5-oxa-13,14-dihydro-16-phenoxy-17,18,19,20-tetranor-$PGA_1$, methyl ester (Formula LVIII).

EXAMPLE 46

5-Oxa-17-phenyl-18,19,20-trinor-$PGB_1$ (Formula LIX: $C_jH_{2j}$ is methylene; $Q_1$ is

$R_1$, $R_2$, $R_3$, $R_4$, $R_5$, $R_8$, and $R_9$ are hydrogen; and s is zero).

Refer to Chart H. A solution of 5-oxa-17-phenyl-18,19,20-trinor $PGE_1$, methyl ester (Example 34, 0.2 g.) in 20 ml. of 50% aqueous ethanol containing 0.5 grams of potassium hydroxide is kept at 25° C. for 10 hr. under nitrogen. Then, the solution is cooled to 10° C. and acidified to pH 1 by addition of 3N. hydrochloric acid at 10° C. The resulting solution is extracted repeatedly with ethyl acetate, and the combined ethyl acetate extracts are washed with water and then with brine, dried, and concentrated to give the title compound.

EXAMPLE 47

5-Oxa- 17-Phenyl and 16-Phenoxy $PGB_1$-type Compounds

Following the procedure of Example 46 but replacing the 5-oxa $PGE_1$-type compound of that example with the appropriate corresponding compound available from the examples herein, there are obtained, for example, the following compounds:

5-oxa-16-phenoxy-17,18,19,20-tetranor-$PGB_1$ (Formula LXI)

5-oxa-13,14-dihydro-17-phenyl-18,19,20-trinor-$PGB_1$ (Formula LX)

5-oxa-13,14-dihydro-16-phenoxy-17,18,19,20-tetranor-$PGB_1$ (Formula LXII).

EXAMPLE 48 5-Oxa-17-phenyl-18,19,20-trinor-$PGB_1$ Methyl Ester (Formula LIX: $C_jH_{2j}$ is methylene; $Q_1$ is

$R_1$ is methyl; and $R_2$, $R_3$, $R_4$, $R_5$, $R_8$, and $R_9$ are hydrogen).

A solution of diazomethane (about 50%) in diethyl ether (25 ml.) is added to a solution of 5-oxa-17-phenyl-18,19,20-trinor-$PGB_1$ (Example 47. 50 mg.) in 25 ml. of a mixture of methanol and diethyl ether (1:1). The mixture is allowed to stand at 25° C. for 5 min. Then the mixture is concentrated to give the title compound.

Following the procedure of Example 48, each of the other specific 5-oxa phenyl- or phenoxy-substituted PGB-type, PGA-type, PGE-type, and PGF-type free acids identified herein is converted to the corresponding methyl ester.

Also following the procedure of Example 48, but using in place of the diazomethane, diazoethane, diazobutane, 1-diazo-2-ethylhexane, and diazocyclohexane, there are obtained the corresponding ethyl, butyl, 2-ethylhexyl, and cyclohexyl esters of 5-oxa-17-phenyl-18,19,20-trinor-$PGB_1$. In the same manner, each of the other specific 5-oxa phenyl- or phenoxy-substituted PGB-type, PGA-type, PGE-type, and PGF-type free acids identified herein is converted to the corresponding ethyl, butyl, 2-ethylhexyl, and cyclohexyl esters.

EXAMPLE 49

5-Oxa-17-phenyl-18,19,20-trinor-$PGE_1$ Methyl Ester Diacetate

Acetic anhydride (5ml.) and pyridine (5 ml.) are mixed with 5-oxa-17-phenyl-18,19,20-trinor-$PGE_1$ methyl ester (Example 34, 20 mg.), and the mixture is allowed to stand at 25° C. for 5–18 hr. The mixture is then cooled to 0° C., diluted with 50 ml. of water, and acidified with 5% hydrochloric acid to pH 1. That mixture is extracted with ethyl acetate and the extract is washed successively with 5% hydrochloric acid, 5% aqueous sodium bicarbonate solution, water, and brine, dried and concentrated to give the title compound.

Following the procedure of Example 34 but replacing the acetic anhydride with propionic anhydride, isobutyric anhydride, and hexanoic acid anhydride, there are obtained the corresponding dipropionate, diisobutyrate and dihexanoate derivatives of 5-oxa-17-phenyl-18,19,20-trinor-$PGE_1$ methyl ester.

Also following the procedure of Example 34, but replacing the PGE₁-type compound with the PGF₁α -type and PGF₁β -type compounds defined herein, there are obtained the corresponding triacetate derivatives of the 5-oxa-17-phenyl-18,19,20-trinor-PGF compounds.

Also following the procedure of Example 34, each of the 5-oxa phenyl- or phenoxy-substituted PGE-type, PGF-type, PGA-type, and PGB-type esters and free acids defined herein is transformed to the corresponding acetates, propionates, isobutyrates, and hexanoates, the PGE-type and the 11-deoxy-PGF-type derivatives being dialkanoates, the PGF-type derivatives being trialkanoates, and the PGA-type, and the PGB-type, and the 11-deoxy-PGE-type derivatives being monoalkanoates.

EXAMPLE 50

5-Oxa-17-phenyl-18,19,20-trinor-PGE₁ from 5-Oxa-17-phenyl-18,19,20-trinor-PGE₁, Methyl Ester There is first prepared an esterase composition from Plexaura homomalla, for which see W. P. Schneider et al., J. Am. Chem. Soc. 94, 2122 (1972). Freshly harvested colony pieces of Plexaura homomalla (Esper), 1792, forma S (10 kg.), are chopped into pieces less than 3 mm. in their longest dimension, and then covered with about three volumes (20 l.) of acetone. The mixture is stirred at about 25° C. for about one hour. The solids are separated by filtration, washed with 1–2 liters of acetone, air dried, and finally stored at about −20° C. as a coarse enzymatic powder.

A suspension of the above powder (2.5 g.) in 25 ml. of water is combined with a solution of 5-oxa-17-phenyl-18,19,20-trinor-PGE₁, methyl ester, (Example 34, 0.5 g.) in about 0.8 ml. of ethanol previously acidified to pH 6 with phosphoric acid. The mixture is stirred at about 25° C. for 24 hr. Then, 50 ml. of acetone is added, the mixture is stirred briefly and filtered, and the filtrate is concentrated under reduced pressure. The aqueous residue is acidified to pH 3.5 with citric acid and extracted with dichloromethane. The combined extracts are concentrated under reduced pressure to the title compound.

Following the procedure of Example 50, but replacing the methyl ester of that example with the methyl esters of the 5-oxa PG compounds identified herein there are obtained the corresponding free acids, for example:

5-oxa-17-phenyl-18,19,20-trinor-PGF₁α
5-oxa-17-phenyl-18,19,20-trinor-PGA₁
5-oxa-11-deoxy-17-phenyl-18,19,20-trinor-PGE₁
5-oxa-13,14-dihydro-17-phenyl-18,19,20-trinor-PGE₁
5-oxa-16-phenoxy-17,18,19,20-tetranor-PGE₁
5-oxa-16-phenoxy-17,18,19,20-tetranor-PGF₁α and
5-oxa-16-phenoxy-17,18,19,20-tetranor-PGA₁.

EXAMPLE 51

5-Oxa-17-phenyl-18,19,20-trinor-PGE₁, Sodium Salt

A solution of 5-oxa-17-phenyl-18,19,20-trinor-PGE₁ (Example 50, 100 mg.) in 50 ml. of a water-ethanol mixture (1:1) is cooled to 5° C. and neutralized with an equivalent amount of 0.1 N. aqueous sodium hydroxide solution. The neutral solution is concentrated to give the title compound.

Following the procedure of Example 51 but using potassium hydroxide, calcium hydroxide, tetramethylammonium hydroxide, and benzyltrimethylammonium hydroxide in place of sodium hydroxide, there are obtained the corresponding salts of 5-oxa-17-phenyl-18,19,20-trinor-PGE₁.

Also following the procedure of Example 52 each of the 5-oxa phenyl- or phenoxy-substituted PGE-type, PGF-type, PGA-type, and PGB-type acids defined herein is transformed to the sodium, potassium, calcium, tetramethylammonium, and benzyltrimethylammonium salts.

I claim:

1. An optically active compound of the formula

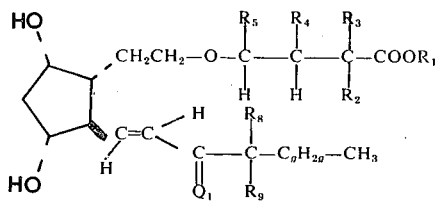

or a racemic compound of that formula and the mirror image thereof, wherein $C_nH_{2n}$ is alkylene of one to 9 carbon atoms inclusive, with one to 5 carbon atoms, inclusive, in the chain between —CR₉R₉—and terminal methyl; wherein Q₁ is

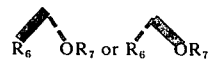

wherein R₆ and R₇ are hydrogen or alkyl of one to 4 carbon atoms, inclusive, being the same or different; wherein R₁ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein R₃, R₈, and R₉ are hydrogen, alkyl of one to 4 carbon atoms, inclusive, or fluoro, being the same or different, with the proviso that R₉ is fluoro only when R₈ is hydrogen or fluoro; wherein R₂ is hydrogen or fluoro, with the proviso that R₂ is fluoro only when R₃ is hydrogen or fluoro; and wherein R₄ and R₅ are hydrogen or alkyl of one to 4 carbon atoms, inclusive, being the same or different, with the proviso that no more than one of R₃, R₄, and R₅ is alkyl; including the lower alkanoates thereof, and the pharmacologically acceptable salts thereof when R₁ is hydrogen.

2. A compound according to claim 1 wherein Q₁ is

wherein R₆ and R₇ are hydrogen or alkyl of one to 4 carbon atoms, inclusive, being the same or different.

3. A compound according to claim 2 wherein the sum of of the carbon atoms in R₆, R₇, R₈, and R₉ taken together is not greater than 7.

4. A compound according to claim 3 wherein R₃, R₄, and R₅ are either hydrogen or methyl, and one of R₃, R₄, and R₅ is methyl.

5. A compound according to claim 3 wherein R₂, R₃, R₄, and R₅ are hydrogen.

6. A compound according to claim 5 wherein R₆, R₇, R₈, and R₉ are either hydrogen or methyl, and at least one of R₆, R₇, R₈, and R₉ is methyl.

7. A compound according to claim 6 wherein $R_6$ is methyl.

8. A compound according to claim 7 wherein $C_gH_{2g}$ is trimethylene.

9. An optically active compound according to claim 8.

10. A compound according to claim 9 wherein $R_1$ is alkyl of one to 12 carbon atoms, inclusive.

11. (15S)-15-Methyl-5-oxa-PGF$_1$ , methyl ester, a compound according to claim 10.

12. A compound according to claim 9 wherein $R_1$ is hydrogen.

13. A racemic compound according to claim 8.

14. A compound according to claim 6 wherein $R_7$ is methyl.

15. A compound according to claim 6 wherein one or both of $R_8$ and $R_9$ are methyl.

16. A compound according to claim 15 wherein $C_gH_{2g}$ is trimethylene.

17. An optically active compound according to claim 16.

18. A compound according to claim 17 wherein $R_1$ is alkyl of one to 12 carbon atoms, inclusive.

19. 16,16-Dimethyl-5-oxa-PGF$_{1\alpha}$ , methyl ester, a compound according to claim 18.

20. A compound according to claim 17 wherein $R_1$ is hydrogen.

21. A racemic compound according to claim 16.

22. A compound according to claim 5 wherein $R_6$, $R_7$, $R_8$, and $R_9$ are hydrogen.

23. A compound according to claim 22 wherein $C_gH_{2g}$ is trimethylene.

24. An optically active compound according to claim 23.

25. A compound according to claim 24 wherein $R_1$ is alkyl of one to 12 carbon atoms.

26. 5-Oxa-PGF$_{1\alpha}$ , methyl ester, a compound according to claim 25.

27. A compound according to claim 24 wherein $R_1$ is hydrogen.

28. 5-Oxa-PGF$_{1\alpha}$ , a compound according to claim 27.

29. A racemic compound according to claim 23.

30. A compound according to claim 1 wherein $Q_1$ is

31. A compound according to claim 30 wherein the sum of the carbon atoms in $R_6$, $R_7$, $R_8$, and $R_9$ taken together is not greater than 7.

32. A compound according to claim 31 wherein $R_3$, $R_4$, and $R_5$ are either hydrogen or methyl, and one of $R_3$, $R_4$, and $R_5$ is methyl.

33. A compound according to claim 31 wherein $R_2$, $R_3$, $R_4$, and $R_5$ are hydrogen.

34. A compound according to claim 33 wherein $R_6$, $R_7$, $R_8$, and $R_9$ are either hydrogen or methyl, and at least one of $R_6$, $R_7$, $R_8$, and $R_9$ is methyl.

35. A compound according to claim 34 wherein $R_6$ is methyl.

36. A compound according to claim 35 wherein $C_gH_{2g}$ is trimethylene.

37. An optically active compound according to claim 36.

38. A compound according to claim 37 wherein $R_1$ is alkyl of one to 12 carbon atoms, inclusive.

39. (15R)-15-Methyl-5-oxa-PGF$_{1\alpha}$ , methyl ester, a compound according to claim 38.

40. A compound according to claim 37 wherein $R_1$ is hydrogen.

41. A racemic compound according to claim 36.

42. A compound according to claim 34 wherein $R_7$ is methyl.

43. A compound according to claim 34 wherein one or both of $R_8$ and $R_9$ are methyl.

44. A compound according to claim 33 wherein $R_6$, $R_7$, $R_8$, and $R_9$ are hydrogen.

* * * * *